(12) United States Patent
Hickman

(10) Patent No.: US 12,130,283 B2
(45) Date of Patent: Oct. 29, 2024

(54) METHODS, SYSTEMS AND COMPOSITIONS FOR FUNCTIONAL IN VITRO CELLULAR MODELS OF MAMMALIAN SYSTEMS

(71) Applicant: University of Central Florida Research Foundation, Inc., Orlando, FL (US)

(72) Inventor: James J. Hickman, Orlando, FL (US)

(73) Assignee: University of Central Florida Research Foundation, Inc., Orlando, FL (US)

( * ) Notice: Subject to any disclaimer, the term of this patent is extended or adjusted under 35 U.S.C. 154(b) by 1121 days.

(21) Appl. No.: 16/985,744

(22) Filed: Aug. 5, 2020

(65) Prior Publication Data

US 2021/0003554 A1   Jan. 7, 2021

Related U.S. Application Data

(63) Continuation of application No. 14/422,082, filed as application No. PCT/US2013/055617 on Aug. 19, 2013, now abandoned.

(60) Provisional application No. 61/789,184, filed on Mar. 15, 2013, provisional application No. 61/684,168, filed on Aug. 17, 2012.

(51) Int. Cl.
*G01N 33/50* (2006.01)
*B01L 3/00* (2006.01)
*C12M 1/36* (2006.01)
*C12M 1/42* (2006.01)
*C12M 3/00* (2006.01)
*G01N 33/483* (2006.01)

(52) U.S. Cl.
CPC ...... *G01N 33/502* (2013.01); *B01L 3/502761* (2013.01); *C12M 21/08* (2013.01); *C12M 35/02* (2013.01); *C12M 41/48* (2013.01); *G01N 33/4836* (2013.01); *G01N 33/5088* (2013.01); *B01L 2200/0684* (2013.01); *B01L 2200/0689* (2013.01); *B01L 2300/0636* (2013.01); *B01L 2300/0645* (2013.01); *B01L 2300/0663* (2013.01); *B01L 2300/0816* (2013.01)

(58) Field of Classification Search
None
See application file for complete search history.

(56) References Cited

U.S. PATENT DOCUMENTS

| | | | |
|---|---|---|---|
| 5,442,510 A | 8/1995 | Schwartz et al. |
| 5,682,899 A | 11/1997 | Nashef et al. |
| 5,948,621 A | 9/1999 | Turner et al. |
| 6,866,383 B2 | 3/2005 | Naik et al. |
| 6,916,541 B2 | 7/2005 | Pantano et al. |
| 6,935,165 B2 | 8/2005 | Bashir et al. |
| 7,384,786 B2 | 6/2008 | Freyman et al. |
| 7,541,146 B2 | 6/2009 | Lewis |
| 7,579,189 B2 | 8/2009 | Freyman et al. |
| 7,691,629 B2 | 4/2010 | Johe et al. |
| 7,860,563 B2 | 12/2010 | Foreman et al. |
| 7,923,015 B2 | 4/2011 | V-Martinez et al. |
| 7,927,671 B2 | 4/2011 | Kato |
| 8,071,319 B2 | 12/2011 | Metzger et al. |
| 8,178,602 B2 | 5/2012 | Mao et al. |
| 8,318,488 B1 | 11/2012 | Bohlen |
| 8,318,489 B2 | 11/2012 | Davidson et al. |
| 8,318,951 B2 | 11/2012 | Olson et al. |
| 8,828,721 B1 | 9/2014 | Hickman et al. |
| 9,404,140 B1 | 8/2016 | Molnar et al. |
| 2003/0054355 A1 | 3/2003 | Warthoe |
| 2003/0065452 A1 | 4/2003 | Hickman |
| 2003/0144823 A1 | 7/2003 | Fox et al. |
| 2003/0211542 A1 | 11/2003 | Lee et al. |
| 2005/0074834 A1 | 4/2005 | Chaplen et al. |
| 2006/0058607 A1 | 3/2006 | Garcia-Webb et al. |
| 2006/0105457 A1 | 5/2006 | Rameshwar |
| 2006/0259992 A1 | 11/2006 | Koren et al. |
| 2007/0015138 A1 | 1/2007 | Barlow et al. |
| 2007/0037225 A1 | 2/2007 | Metzger et al. |
| 2007/0089515 A1 | 4/2007 | Shih et al. |
| 2007/0117217 A1 | 5/2007 | Lal et al. |
| 2007/0122896 A1 | 5/2007 | Shuler et al. |
| 2007/0129447 A1 | 6/2007 | Sra |
| 2007/0212723 A1 | 9/2007 | Dudley et al. |
| 2007/0218534 A1 | 9/2007 | Klenerman et al. |
| 2008/0124789 A1 | 5/2008 | Hickman |
| 2008/0138797 A1 | 6/2008 | Hunt et al. |
| 2008/0166795 A1 | 7/2008 | Shuler et al. |

(Continued)

FOREIGN PATENT DOCUMENTS

| | | |
|---|---|---|
| CA | 2788905 | 8/2011 |
| CA | 2798777 | 10/2011 |

(Continued)

OTHER PUBLICATIONS

Examination Search Report dated Nov. 2, 2021, issued in Canadian Application No. 2,899,445 (3 pages).

(Continued)

*Primary Examiner* — Brian Gangle
*Assistant Examiner* — Lakia J Jackson-Tongue
(74) *Attorney, Agent, or Firm* — Meunier Carlin & Curfman LLC

(57) ABSTRACT

The present invention comprises methods, systems and compositions comprising cell culture analog systems, comprising components which optionally comprise biologically functional cells, and the components and systems function similarly to in vivo conditions.

19 Claims, 21 Drawing Sheets

(56) References Cited

U.S. PATENT DOCUMENTS

| | | |
|---|---|---|
| 2008/0227137 A1 | 9/2008 | Zhang et al. |
| 2009/0029463 A1 | 1/2009 | Collins |
| 2009/0078023 A1 | 3/2009 | Mutharasan et al. |
| 2009/0226768 A1 | 9/2009 | Wang et al. |
| 2009/0227469 A1 | 9/2009 | Conklin et al. |
| 2009/0239940 A1 | 9/2009 | Del Monte et al. |
| 2009/0305319 A1 | 12/2009 | Baudenbacher |
| 2010/0028902 A1 | 2/2010 | Brown et al. |
| 2010/0127280 A1 | 11/2010 | Parker et al. |
| 2012/0135452 A1 | 5/2012 | Shuler et al. |
| 2012/0142556 A1 | 6/2012 | Parker et al. |
| 2014/0274796 A1 | 9/2014 | Hickman |
| 2015/0369791 A1 | 12/2015 | Hickman et al. |
| 2016/0041150 A1 | 2/2016 | Hickman et al. |
| 2016/0305927 A1 | 10/2016 | Molnar et al. |
| 2018/0095073 A1 | 4/2018 | Hickman |

FOREIGN PATENT DOCUMENTS

| | | | |
|---|---|---|---|
| EP | | 2434896 | 4/2012 |
| EP | | 2435585 | 4/2012 |
| EP | | 2531910 | 12/2012 |
| EP | | 2585171 | 5/2013 |
| EP | | 2951281 B1 | 12/2015 |
| WO | | 2001/029206 | 4/2001 |
| WO | | 2005/033264 | 4/2005 |
| WO | | 2005/108598 | 11/2005 |
| WO | | 2009/036573 | 3/2009 |
| WO | | 2010/127280 | 11/2010 |
| WO | | 2010/138679 | 12/2010 |
| WO | | 2010/138782 | 12/2010 |
| WO | | 2011/097574 | 8/2011 |
| WO | WO 2011/102991 | * | 8/2011 |
| WO | | 2011/133985 | 10/2011 |
| WO | | 2012/158923 | 11/2012 |
| WO | | 2013/013206 | 1/2013 |
| WO | | 2013056019 A1 | 4/2013 |
| WO | WO 2013/086512 A2 | * | 6/2013 |
| WO | | 2014120952 A1 | 8/2014 |

OTHER PUBLICATIONS

Non-Final Office Action issued in co-pending U.S. Appl. No. 16/913,528, mailed Mar. 30, 2022.
Abbanat D, et al. (2003) Novel antibacterial agents for the treatment of serious Gram-positive infections. Expert Opin Investig Drugs. 12: 379-399.
Abdi H. (2003) Multivariate Analysis. Encyclopedia of Social Sciences Research Methods. M. Lewis-Beck, A. Bryman and T. Futing. Thousand Oaks (CA), Sage.
Adell A, et al. (2002) Origin and functional role of the extracellular serotonin in the midbrain raphe nuclei. Brain Res Brain Res Rev. 39: 154-180.
Agarwal A, et al. (2013) Microfluidic heart on a chip for higher throughput pharmacological studies. Lab Chip. 13: 3599-3608.
Ahern CA, et al. (2003) Ca2+ current and charge movements in skeletal myotubes promoted by the beta-subunit of the dihydropyridine receptor in the absence of ryanodine receptor type 1. Biophys J. 84: 942-959.
Ahmari SE, et al. (2000) Assembly of presynaptic active zones from cytoplasmic transport packets. Nat Neurosci. 3: 445-451.
Ahuja TK, et al. (2007) Hippocampal slice cultures integrated with multi-electrode arrays: A model for study of long-term drug effects on synaptic activity. Drug Development Research. 68: 84-93.
Ainscow EK and Brand MD. (1999) Internal regulation of ATP turnover, glycolysis and oxidative phosphorylation in rat hepatocytes. Eur J Biochem. 266:737-749.
Akaaboune M, et al. (2000) Developmental regulation of amyloid precursor protein at the neuromuscular junction in mouse skeletal muscle. Mol Cell Neurosci. 15: 355-367.

Akanda N, et al. (2008) Effect of malonate, a metabolic pathway inhibitor, on action potential peak shape and the relationship to cellular pathways. 38th Annual Meeting of the Society for Neuroscience. vol 38.
Akanda N, et al. (2009) Analysis of toxin-induced changes in action potential shape for drug development. J Biomol Screen. 14: 1228-1235.
Alabed YZ, et al. (2006) Neuronal responses to myelin are mediated by rho kinase. J Neurochem. 96: 1616-1625.
Albensi BC. (2003) A comparison of drug treatment versus electrical stimulation for suppressing seizure activity. Drug News Perspect. 16: 347-352.
Albert R and Othmer H. (2003) The topology of the regulatory interactions predicts the expression pattern of the segment polarity genes in *Drosophila melanogaster*. J Theor Biol. 223: 1-18.
Albert Y, et al. (2005) Transcriptional regulation of myotube fate specification and intrafusal muscle fiber morphogenesis. J Cell Biol. 169: 257-268.
Alexander SL, et al. (1989) An atomic-resolution atomic-force microscope implemented using an optical lever. J Appl Phys. 65: 164-167.
Al-Shanti N, et al. (2008) Beneficial synergistic interactions of TNF-alpha and IL-6 in C2 skeletal myoblasts—potential cross-talk with IGF system. Growth Factors. 26: 61-73.
Alsina B, et al. (2001) Visualizing synapse formation in arborizing optic axons in vivo: dynamics and modulation by BDNF. Nat Neurosci. 4: 1093-1101.
Alterio J, et al. (1990) Acidic and basic fibroblast growth factor mRNAs are expressed by skeletal muscle satellite cells.Biochem Biophys Res Commun. 166:1205-1212.
Altmann L. (2000) Multielectrode recordings of synaptic plasticity in brain slices: A new method for the assessment of neurotoxic effects. European Journal of Neuroscience. 12: 29-29.
Amarenco P, et al. (2006) High-dose atorvastatin after stroke or transient ischemic attack. N Engl J Med. 355: 549-559.
Amit M. (2007) Feeder-layer free culture system for human embryonic stem cells. Methods Mol Biol. 407: 11-20.
Anderson DJ, et al. (1997) Cell lineage determination and the control of neuronal identity in the neural crest. Cold Spring Harb Symp Quant Biol. 62: 493-504.
Anderson JE, et al. (1991) Distinctive patterns of basic fibroblast growth factor (bFGF) distribution in degenerating and regenerating areas of dystrophic (mdx) striated muscles. Dev Biol. 147: 96-109.
Andersson Hand van den Berg A. (2004) Microfabrication and microfluidics for tissue engineering: state of the art and future opportunities. Lab Chip. 4: 98-103.
Antzelevitch C. (2001) Transmural dispersion of repolarization and the T wave. Cardiovasc Res. 50: 426-431.
Antzelevitch C. (2005) Cardiac repolarization. The long and short of it. Europace. 7: 3-9.
Aracil A, et al. (2004) Proceedings of Neuropeptides 2004, the XIV European Neuropeptides Club meeting. Neuropeptides. 38: 369-371.
Archer JD, et al. (2006) Persistent and improved functional gain in mdx dystrophic mice after treatment with L-arginine and deflazacort. F ASEB J. 20:738-740.
Armstrong DL and Rossie S. (1999) Ion channel regulation. Introduction. Adv Second Messenger Phosphoprotein Res. 33: ix-xx.
Arnold HH and Winter B. (1998) Muscle differentiation: more complexity to the network of myogenic regulators. Curr Opin Genet Dev. 8: 539-544.
Arnone MI and Davidson EH. (1997) The hardwiring of development: organization and function of genomic regulatory systems. Development. 124:1851-1864.
Arsic N, et al. (2004) Vascular endothelial growth factor stimulates skeletal muscle regeneration in vivo. Mol Ther. 10: 844-854.
Askanas V, et al. (1987) De novo neuromuscular junction formation on human muscle fibres cultured in monolayer and innervated by foetal rat spinal cord: ultrastructural and ultrastructural—cytochemical studies. J Neurocytol. 16: 523-537.
Asotra K and Macklin WB. (1993) Protein kinase C activity modulates myelin gene expression in enriched oligodendrocytes. J Neurosci Res. 34: 571-588.

(56) References Cited

OTHER PUBLICATIONS

Azzouz M, et al. (2004) VEGF delivery with retrogradely transported lentivector prolongs survival in a mouse ALS model. Nature. 429: 413-41 7.
Badie N, et al. (2009) A method to replicate the microstructure of heart tissue in vitro using DTMRI-based cell micropatteming. Ann Biomed Eng. 37: 2510-2521.
Badie et al. (2009b) Novel micropatterned cardiac cell cultures with realistic ventricular microstructure. Biophysical Journal 96: 3873-3885.
Bahr M, et al. (1991) In vitro myelination of regenerating adult rat retinal ganglion cell axons by Schwann cells. Glia. 4: 529-533.
Baker DC, et al. (2002) The origin and neuronal function of in vivo nonsynaptic glutamate. J Neurosci. 22: 9134-9141.
Bandi E, et al. (2008) Neural agrin controls maturation of the excitation-contraction coupling mechanism in human myotubes developing in vitro. Am J Physiol Cell Physiol. 294: C66-C73.
Bansal R and Pfeiffer SE. (1992) Novel stage in the oligodendrocyte lineage defined by reactivity of progenitors with R-mAb pnor to QI antigalactocerebroside. J Neurosci Res. 32: 309-316.
Baraban SC, et al. (1997) Osmolarity modulates K+ channel function on rat AI56. hippocampal intemeurons but not CAI pyramidal neurons. J Physiol. 498: 679-689.
Barbulovic-Nad I, et al. (2008) Digital microfluidics for cell-based assays. Lab Chip. 8: 519-526.
Baron W, et al. (2000) PDGF and FGF-2 signaling in oligodendrocyte progenitor cells: regulation of proliferation and differentiation by multiple intracellular signaling pathways. Mol Cell Neurosci. I5: 314-329.
Barone FC, et al. (1998) Ischemic preconditioning and brain tolerance: temporal histological and functional outcomes, protein synthesis requirement, and interleukin-I receptor antagonist and early gene expression. Stroke. 29: 1937-1950.
Behar TN. (2001) Analysis of fractal dimension of 02A glial cells differentiating in vitro. Methods. 24: 331-339.
Belardinelli L, et al. (2003) Assessing predictors of drug-induced torsade de pointes. Trends Pharmacol Sci. 24: 619-625.
Bellamkonda R, et al. (1995) Hydrogel-based three-dimensional matrix for neural cells. J Biomed Mater Res. 29: 663-671.
Bellas E, et al. (2012) In vitro 3D full-thickness skin-equivalent tissue model using silk and collagen biomaterials. Macromol Biosci. 12: 1627-1236.
Benabid AI. (2003) Deep brain stimulation for Parkinson's disease. Curr Opin Neurobiol. 13: 696-706.
Bender A, et al. (2007) Analysis of pharmacology data and the prediction of adverse drug reactions and off-target effects from chemical structure. ChemMedChem. 2: 861-873.
Bentley A and Atkinsona, A. (2001) Whole cell biosensors—electrochemical and optical approaches to ecotoxicity testing. Toxicol In Vitro. 15: 469-475.
Berg MC, et al. (2004) Controlling mammalian cell interactions on patterned polyelectrolyte multilayer surfaces. Langmuir. 20: 1362-1368.
Berger TW, et al. (2001) Brain-implantable biomimetic electronics as the next era in neural prosthetics. Proceedings of the IEEE. 89: 993-1012.
Bernstein M, et al. (1996) Receptor-mediated calcium signalling in glial cells from mouse corpus callosum slices. J Neurosci Res. 46: 152-163.
Bers DM. (2002) Cardiac excitation-contraction coupling. Nature. 415: 198-205.
Bettinger CJ, et al. (2009) Engineering substrate topography at the micro- and nanoscale to control cell function. Angew Chem Int Ed Engl. 48: 5406-5415.
Bhalla US and Iyengar R. (1999) Emergent properties of networks of biological signaling pathways. Science. 283: 381-387.
Bhat NR, et al. (2007) p38 MAP kinase regulation of oligodendrocyte differentiation with CREB as a potential target. Neurochem Res. 32: 293-302.
Bian WN and Tung L. (2006) Structure-related initiation of reentry by rapid pacing in monolayers of cardiac cells. Circ Res. 98: e29-38.
Biesecker G. (1990) The complement SC5b-9 complex mediates cell adhesion through a vitronectin receptor. J Immunol. 145: 209-214.
Bikfalvi A, et al. (1997) Biological roles of fibroblast growth factor-2. Endocr Rev. 18: 26-45.
Bischoff U, et al. (2000) Effects of fluoroquinolones on HERG currents. Eur J Pharmacol. 406: 341-343.
Bloch-Gallego E, et al. (1991) Survival in vitro of motoneurons identified or purified by novel antibody-based methods is selectively enhanced by musclederived factors. Development. 111: 221-232.
Bodine SC, et al. (2001) Identification of ubiquitin ligases required for skeletal muscle atrophy. Science. 294: 1704-1708.
Bogler O, et al. (1990) Cooperation between two growth factors promotes extended self-renewal and inhibits differentiation of oligodendrocyte-type-2 astrocyte (0-2A) progenitor cells. Proc Natl Acad Sci US A. 87: 6368-6372
Boillee S, et al. (2006) ALS: a disease of motor neurons and their nonneuronal neighbors. Neuron. 52: 39-59.
Boldin SA and Futerman AH. (2000) Up-regulation of glucosylceramide synthesis upon stimulation of axonal growth by basic fibroblast growth factor. Evidence for post-translational modification of glucosylceramide synthase. J Biol Chem. 275: 9905-9909.
Bordet T, et al. (2001) Protective effects of cardiotrophin-1 adenoviral gene transfer on neuromuscular degeneration in transgenic ALS mice. Hum Mol Genet. 10: 1925-1933.
Bottenstein JE, et al. (1988a) CNS neuronal cell line-derived factors regulate gliogenesis in neonatal rat brain cultures. J Neurosci Res. 20: 291-303.
Bottenstein JE. (1981) Proliferation of glioma cells in serum-free defined medium. Cancer Treat Rep. 65 Suppl 2: 67-70.
Bottenstein JE. (1988b) Advances in vertebrate cell culture methods. Science. 239: G 42, G 48.
Bourgeois EB, et al. (2009) Change in conduction velocity due to fiber curvature in cultured neonatal rat ventricular myocytes. IEEE Trans Biomed Eng. 56: 855-861.
Bousse L. (1996) Whole cell biosensors. Sens Actuators B: Chem. 34: 270-275.
Bowman WC. (2006) Neuromuscular block. Br J Pharmacol. 147 Suppl 1: S277-S286.
Bracciali A, et al. (2008) Stochastic models for the in silico simulation of synaptic processes. BMC Bioinformatics. 9 Suppl 4: S7.
Brand T, et al. (2000) EMBO Workshop Report: Molecular genetics of muscle development and neuromuscular diseases, Kloster Irsee, Germany, Sep. 26-Oct. 1, 1999. EMBO J. 19: 1935-1941.
Brand-Saberi B and Christ B. (1999) Genetic and epigenetic control of muscle development in vertebrates. Cell Tissue Res. 296: 199-212.
Brand-Saberi B. (2005) Genetic and epigenetic control of skeletal muscle development. Ann Anat. 187: 199-207.
Bregman BS, et al. (1997) Neurotrophic factors increase axonal growth after spinal cord injury and transplantation in the adult rat. Exp Neurol. 148: 475-494.
Bren-Mattison Y and Olwin BB. (2002) Sonic hedgehog inhibits the terminal A195. differentiation of limb myoblasts committed to the slow muscle lineage. Dev Biol. 242: 130-148.
Brewer GJ, et al. (1993) Optimized survival of hippocampal neurons in B27 supplemented Neurobasal, a new serum-free medium combination. J Neurosci Res. 35: 567-576.
Brewer GJ, et al. (2008) NbActiv4 medium improvement to Neurobasal/B27 increases neuron synapse densities and network spike rates on multielectrode arrays. J Neurosci Methods. 170: 181-187.
Brewer GJ. (1997) Isolation and culture of adult rat hippocampal neurons. J Neurosci Methods. 71: 143-155.
Brewer GJ. (1999) Regeneration and proliferation of embryonic and adult rat hippocampal neurons in culture. Exp Neurol. 159: 237-247.
Brito-Martins M, et al. (2008) beta(I)- and beta(2)-adrenoceptor responses in cardiomyocytes derived from human embryonic stem cells: comparison with failing and non-failing adult human heart. Br J Pharmacol. 153: 751-759.

(56) References Cited

OTHER PUBLICATIONS

Brockes JP, et al. (1979) Studies on cultured rat Schwann cells. I. Establishment of purified populations from cultures of peripheral nerve. Brain Res. 165: 105-118.
Brokhman I, et al. (2008) Peripheral sensory neurons differentiate from neural precursors derived from human embryonic stem cells. Differentiation. 76: 145-155.
Brumovsky P, et al. (2007) Expression of the vesicular glutamate transporters- I and -2 in adult mouse dorsal root ganglia and spinal cord and their regulation by nerve injury. Neuroscience. 147: 469-490.
Bult CJ, et al. (1996) Complete genome sequence of the methanogenic archaeon, Methanococcus jannaschii. Science. 273: 1058-1073.
Bunge MB, et al. (1962) Electron microscopic demonstration of connections between glia and myelin sheaths in the developing mammalian central nervous system. J Cell Biol. 12: 448-453.
Bunge RP. (1968) Glial cells and the central myelin sheath. Physiol Rev. 48: 197-251.
Bunge RP. (1993) Expanding roles for the Schwann cell: ensheathment, myelination, trophism and regeneration. Curr Opin Neurobiol. 3: 805-809.
Burdick JA and Vunjak-Novakovic G. (2009) Engineered microenvironments for controlled stem cell differentiation. Tissue Eng Part A. 15: 205-219.
Burgess C, et al. (2008) An endogenous glutamatergic drive onto somatic motoneurons contributes to the stereotypical pattern of muscle tone across the sleep-wake cycle. J Neurosci. 28: 4649-4660.
Butt HJ. (1996) Sensitive Method to Measure Changes in the Surface Stress of Solids. Journal of Colloid and Interface Science. 180: 251-260.
Buzanska L, et al. (2002) Human cord blood-derived cells attain neuronal and glial features in vitro. J Cell Sci. 115: 2131-2138.
Cai J, et al. (2007) Directed differentiation of human embryonic stem cells into functional hepatic cells. Hepatology. 45: 1229-1239.
Caiozzo VJ, at al. (1992) Response of slow and fast muscle to hypothyroidism: maximal shortening velocity and myosin isoforms. Am J Physiol. 263: C86-C94.
Cakir T, et al. (2007) Reconstruction and flux analysis of coupling between metabolic pathways of astrocytes and neurons: application to cerebral hypoxia. Theor Biol Med Model. 4: 48.
Campbell TJ and Williams KM. (2001) Therapeutic drug monitoring: antiarrhythmic drugs. Br J Clin Pharmacol. 52 Suppl 1: 21S-34S.
Camu Wand Henderson CE. (1992) Purification of embryonic rat motoneurons by panning on a monoclonal antibody to the low-affinity NGF receptor. J Neurosci Methods. 44: 59-70.
Camu W and Henderson CE. (1994) Rapid purification of embryonic rat motoneurons: an in vitro model for studying MND/ALS pathogenesis. J Neurol Sci. 124 Suppl: 73-74.
Cannon JG. (1998) Intrinsic and extrinsic factors in muscle aging. Ann NY Acad Sci. 854: 72-77.
Caratsch CG, et al. (1994) Interferon-alpha, beta and tumor necrosis factor-alpha enhance the frequency of miniature end-plate potentials at rat neuromuscular junction. Neurosci Lett. 166: 97-100.
Carlsson L. (2006) In vitro and in vivo models for testing arrhythmogenesis in drugs. J Intern Med. 259: 70-80.
Carpenedo RL, et al. (2007) Rotary suspension culture enhances the efficiency, yield, and homogeneity of embryoid body differentiation. Stem Cells. 25: 2224-2234.
Carr PA, et al. (1989) Parvalbumin is highly colocalized with calbindin D28k and rarely with calcitonin gene-related peptide in dorsal root ganglia neurons of rat. Brain Res. 497: 163-170.
Carrasco DI and English AW. (2003) Neurotrophin 4/5 is required for the normal development of the slow muscle fiber phenotype in the rat soleus. J Exp Biol. 206: 2191-2200.
Caspi O, et al. (2009) In vitro electrophysiological drug testing using human embryonic stem cell derived cardiomyocytes. Stem Cells Dev. 18: 161-172.
Catoire H, et al. (2008) Sirtuin inhibition protects from the polyalanine muscular dystrophy protein PABPNI. Hum Mol Genet. 17: 2108-2117.
Cerignoli F, et al. (2012) High throughput measurement of Ca2+ dynamics for drug risk assessment in human stem cell-derived cardiomyocytes by kinetic image cytometry. J Pharmacol Toxicol Methods. 66: 246-256.
Chambers SM, et al. (2009) Highly efficient neural conversion of human ES and iPS cells by dual inhibition of SMAD signaling. Nat Biotechnol. 27: 275-280.
Chandran S, et al. (1998) Regional potential for oligodendrocyte generation in the rodent embryonic spinal cord following exposure to EGF and FGF-2. Glia. 24: 382-389.
Chang JC, et al. (2001) Modulation of neural network activity by patterning. Biosens Bioelectron. 16: 527-533.
Charpentier A, et al. (1993) RRR-alpha-tocopheryl succinate inhibits proliferation and enhances secretion of transforming growth factor-beta (TGFbeta) by human breast cancer cells. Nutr Cancer. 19: 225-239.
Chaudhary KW, et al. (2006) Embryonic stem cells in predictive cardiotoxicity: laser capture microscopy enables assay development. Toxicol Sci. 90: 149-158.
Chaves M, et al. (2005) Robustness and fragility of Boolean models for genetic regulatory networks. J Theor Biol. 235: 431-449.
Chaves M, et al. (2006) Methods of robustness analysis for Boolean models of gene control networks. Syst Biol (Stevenage). 153: 154-167.
Chen CS, et al. (1997) Geometric control of cell life and death. Science. 276: 1425-1428.
Chen EW, et al. (1995) Target regulation of a motor neuron-specific epitope. J Neurosci. 15: 1555-1566.
Chen J and von Bartheld CS. (2004) Role of exogenous and endogenous trophic factors m the regulation of extraocular muscle strength during development.Invest Ophthalmol Vis Sci. 45: 3538-3545.
Chen QS, et al. (2000) Impairment of hippocampal long-term potentiation by Alzheimer amyloid beta-peptides. J Neurosci Res. 60: 65-72.
Chen X, et al. (2005) Dedifferentiation of adult human myoblasts induced by ciliary neurotrophic factor in vitro. Moll Biol Cell. 16: 3140-3151.
Chen XF, et al. (2008) Dynamic simulation of the effect of calcium-release activated calcium channel on cytoplasmic Ca2+ oscillation. Biophys Chem. 136: 87-95.
Chen XP, (2003) Exogenous rhCNTF inhibits myoblast differentiation of skeletal muscle of adult human in vitro. Sheng Li Xue Bao. 55: 464-468.
Chiu A Y, et al. (1993) A motor neuron-specific epitope and the low-affinity nerve growth factor receptor display reciprocal patterns of expression during development, axotomy, and regeneration. J Comp Neurol. 328: 351-363.
Choi-Lundberg DL and Bohn MC. (1995) Ontogeny and distribution of glial cell line-derived neurotrophic factor (GDNF) mRNA in rat. Brain Res Dev Brain Res. 85: 80-88.
Choudhury A, et al. (2007) A piezoresistive microcantilever array for surface stress measurement: curvature model and fabrication. J Micromech Microeng. 17: 2065-2076.
Chow I and Poo MM. (1985) Release of acetylcholine from embryonic neurons upon contact with muscle cell. J Neurosci. 5: 1076-1082.
Christ B and Brand-Seberi B. (2002) Limb muscle development. Int J Dev Biol. 46: 905-914.
Cizkova D, et al. (2007) Functional recovery in rats with ischemic paraplegia after spinal grafting of human spinal stem cells. Neuroscience. 147: 546-560.
Clegg CH, et al. (1987) Growth factor control of skeletal muscle differentiation: commitment to terminal differentiation occurs in G1 phase and is repressed by fibroblast growth factor. J Cell Biol. 105: 949-956.
Clements JD, et al. (1992) The time course of glutamate in the synaptic cleft. Science. 258: 1498-1501.
Coggan JS, et al. (2005) Evidence for ectopic neurotransmission at a neuronal synapse. Science. 309: 446-451.

(56) References Cited

OTHER PUBLICATIONS

Cohen RI and Almazan G. (1993) Norepinephrine-stimulated PI hydrolysis in oligodendrocytes is mediated by alpha IA-adrenoceptors. Neuroreport. 4: 1115-1118.
Cohen-Cory S. (2002) The developing synapse: construction and modulation of synaptic structures and circuits. Science. 298: 770-776.
Collins CA and Morgan JE. (2003) Duchenne's muscular dystrophy: animal models used to investigate pathogenesis and develop therapeutic strategies. Int J Exp Pathol. 84: 165-172.
Colomar A and Robitaille R. (2004) Glial modulation of synaptic transmission at the neuromuscular junction. Glia. 4 7: 284-289.
Cooper A, et al. (1976) The growth of mouse neuroblastoma cells in controlled orientations on thin films of silicon monoxide. Exp Cell Res. 103: 435-439.
Corey JM, et al. (1991) Compliance of hippocampal neurons to patterned substrate networks. J Neurosci Res. 30: 300-307.
Corey JM, et al. ( 1996) Micrometer resolution silane-based patterning of hippocampal neurons: critical variables in photoresist and laser ablation processes for substrate fabrication. IEEE Trans Biomed Eng. 43: 944-955.
Corey JM, et al. (1997) Differentiated B 104 neuroblastoma cells are a highresolution assay for micropatterned substrates. J Neurosci Methods. 75: 91-97.
Cortassa S, et al. (2003) An integrated model of cardiac mitochondrial energy metabolism and calcium dynamics. Biophys J. 84: 2734-2755.
Cossu G, et al. (1996) How is myogenesis initiated in the embryo? Trends Genet. 12: 218-223.
Courdier-Fruh I, et al. (2002) Glucocorticoid-mediated regulation of utrophin levels in human muscle fibers. Neuromuscul Disord. 12(Suppl 1): S95-S104.
Cross-Doersen D and Isfort RJ. (2003) A novel cell-based system for evaluating skeletal muscle cell hypertrophy-inducing agents. In Vitro Cell Dev Biol Animal. 39: 407-412.
Cukierman E, et al. (2002) Cell interactions with three-dimensional matrices. Curr Opin Cell Biol. 14: 633-639.
Cunningham JJ and Roussel MF. (2001) Cyclin-dependent kinase inhibitors in the development of the central nervous system. Cell Growth Differ. 12: 387-396.
Cuppini R, et al. (2001) Alpha-tocopherol controls cell proliferation in the adult rat dentate 12:vrus. Neurosci Lett. 303: 198-200.
Currie PD and Ingham PW. (1996) Induction of a specific muscle cell type by a hedgehog-like protein in zebrafish. Nature. 382: 452-455.
Curtis R, et al. (1988) Development of macroglial cells in rat cerebellum. I. Use of antibodies to follow early m VIVO development and migration of oligodendrocytes. J Neurocytol. 17: 43-54.
Cysyk J and Tung L. (2008) Electric field perturbations of spiral waves attached to millimeter-size obstacles. Biophys J. 94: 1533-1541.
Dakhel Y and Jamali F. (2006) Erythromycin potentiates PR interval prolonging effect of verapamil in the rat: a pharmacodynamic drug interaction. Toxicol Appl Pharmacol. 214: 24-29.
Daniels MP, et al. (2000) Rodent nerve-muscle cell culture system for studies of neuromuscular junction development: refinements and applications. Microsc Res Tech. 49: 26-37.
Daniels MP. (1990) Localization of actin, beta-spectrin, 43x10(3) Mr and 58x10(3) Mr proteins to receptor-enriched domains of newly formed acetylcholine receptor aggregates in isolated myotube membranes. J Cell Sci. 97(Pt 4): 615-626.
Daniels MP. (1997) Intercellular communication that mediates formation of the neuromusculariunction. Mol Neurobiol. 14: 143-170.
Das M, et al. (2003) Electrophysiological and morphological characterization of rat embryonic motoneurons in a defined system. Biotechnol Prog. 19: 1756-1761.
Das M, et al. (2004) Long-term culture of embryonic rat cardiomyocytes on an organosilane surface in a serum-free medium. Biomaterials. 25: 5643-5647.

Das M, et al. (2005) Adult rat spinal cord culture on an organosilane surface in a novel serum-free medium. In Vitro Cell Dev Biol Anim. 41: 343-348.
Das M, et al. (2006) A defined system to allow skeletal muscle differentiation and subsequent integration with silicon microstructures. Biomaterials. 27: 4374-4380.
Das M, et al. (2007a) Auto-catalytic ceria nanoparticles offer neuroprotection to adult rat spinal cord neurons. Biomaterials. 28: 1918-1925.
Das M, et al. (2007b) Differentiation of skeletal muscle and integration of myotubes with silicon microstructures using serum-free medium and a synthetic silane substrate. Nat Protoc. 2: 1795-1801.
Das M, et al. (2007c) Embryonic motoneuron-skeletal muscle co-culture in a defined system. Neuroscience. 146: 481-488.
Das M, et al. (2008) Temporal neurotransmitter conditioning restores the functional activity of adult spinal cord neurons in long-term culture. Exp Neurol. 209: 171-180.
Das M, et al. (2009a) Developing a novel serum-free cell culture model of skeletal muscle differentiation by systematically studying the role of different growth factors in myotube formation. In Vitro Cell Dev Biol Anim. 45: 378-387.
Das M, et al. (2009b) Skeletal Muscle Tissue Engineering: An Improved Model Promoting Long Term Survival of Myotubes, Structural Development of E-C Coupling Apparatus and Neonatal Myosin Heavy Chain (MHC) Expression. Biomaterials. 30: 5392-5402.
Das M, et al. (2010) A defined long-term in vitro tissue engineered model of neuromuscular junctions. Biomaterials. 31: 4880-4888.
Datar R, et al. (2009) Cantilever Sensors: Nanomechanical Tools for Diagnostics. MRS Bulletin. 34: 449-454.
David JA and Pitman RM. (1982) The effects of axotomy upon the extrasynaptic acetylcholine sensitivity of an identified motoneurone m the cockroach Periplaneta americana. J Exp Biol. 98: 329-341.
Davis H, et al. (2012) Rat Cortical Oligodendrocyte-Embryonic Motoneuron Co-Culture: An In Vitro Axon-Oligodendrocyte Interaction Model. J Biomater Tissue Eng. 2: 206-214.
De Clerck F, et al. (2002) In vivo measurement of QT prolongation, dispersion and arrhythmogenesis: application to the preclinical cardiovascular safety pharmacology of a new chemical entity. Fundam Clin Pharmacol. 16: 125-140.
De Felice FG, et al. (2001) Inhibition of Alzheimer's disease beta-amyloid aggregation, neurotoxicity, and in vivo deposition by nitrophenols: implications for Alzheimer's therapy. FASEB J. 15: 1297-1299.
De Lange P, et al. (2006) Sequential changes in the signal transduction responses of skeletal muscle following food deprivation. FASEB J. 20: 2579-2581.
De Wilde J, et al. (2008) Short-term high fat-feeding results in morphological and metabolic adaptations m the skeletal muscle of C57BL/6J mice. Physiol Genomics. 32: 360-369.
Dell'Era P, et al. (2003) Fibroblast growth factor receptor-I is essential for in vitro cardiomyocyte development. Circ Res. 93: 414-420.
Denning C and Anderson D. (2008) Cardiomyocytes from human embryonic A291. stem cells as predictors of cardiotoxicity. Drug Discovery Today: Therapeutic Strategies. 5: 223-232.
Dennis RG and Kosnik IPE. (2000) Excitability and isometric contractile A292. properties of mammalian skeletal muscle constructs engineered in vitro. In Vitro Cell Dev Biol Anim. 36: 327-335.
Dennis RG, et al. (2001) Excitability and contractility of skeletal muscle A293. engineered from primary cultures and cell lines. Am J Physiol Cell Physiol. 280: C288-C295.
Denyer MCT, et al. (1998) Preliminary study on the suitability of a A294. pharmacological bio-assay based on cardiac myocytes cultured over microfabricated microelectrode arrays. Med Biol Eng Comput. 36: 638-644.
Descarries L, et al. (1997) Diffuse transmission by acetylcholine in the CNS. Prog Neurobiol. 53: 603-625.
Dhvan Rand Tsai L. (2001) A decade of CDK5. Nat Rev Mol Cell Biol. 2: 749-759.
Dhir, V. (2003) Application of polyelectrolyte multilayers for photolithographic patterning of diverse mammalian cell types in serum

(56) References Cited

OTHER PUBLICATIONS free medium. Masters Thesis in the Department of Mechanical, Materials and Aerospace Engineering in the College of Engineering and Computer Science. University of Central Florida. Orlando, Florida, Fall Term 2008.

Dhir V, et al. (2009) Patterning of diverse mammalian cell types in serum free medium with photoablation. Biotechnol Prog. 25: 594-603.

Di Giovanni S, et al. (2005) Cell cycle inhibition provides neuroprotection and reduces glial proliferation and scar formation after traumatic brain injury. Proc Natl Acad Sci U Sa. 102: 8333-8338.

Dimitrova DS and Gilbert DM. (2000) Temporally coordinated assembly and disassembly of replication factories in the absence of DNA synthesis. Nat Cell Biol. 2: 686-694.

Djouhri L and Lawson SN. (1999) Changes in somatic action potential shape in guinea-pig nociceptive primary afferent neurones during inflammation in vivo. J Physiol. 520 Pt 2: 565-576.

Dolcet X, et al. (2001) Cytokines promote motoneuron survival through the Janus kinase-dependent activation of the phosphatidylinositol 3-kinase pathway. Mol Cell Neurosci. 18: 619-631.

Du Y, et al. (2006) Distinct effects of p75 in mediating actions of neurotrophins on basal forebrain oligodendrocytes. Mol Cell Neurosci. 31: 366-375.

Dulcey CS, et al. (1991) Deep UV photochemistry of chemisorbed monolayers: patterned coplanar molecular assemblies. Science. 252: 551-554.

Dumont RJ, et al. (2001) Acute spinal cord injury, part I: pathophysiologic mechanisms. Clin Neuropharmacolo12:v. 24: 254-264.

Duport S, et al. (1999) A metallic multisite recording system designed for continuous long- term monitoring of electrophysiological activity in slice cultures. Biosens Bioelectron. 14: 369-376.

Dusterhoft S and Pette D. (1999) Evidence that acidic fibroblast growth factor promotes maturation of rat satellite-cell-derived myotubes m vitro. Differentiation. 65: 161-169.

Dutton EK, et al. (1995) Acetylcholine receptor aggregation at nerve-muscle contacts in mammalian cultures: induction by ventral spinal cord neurons is specific to axons. J Neurosci. 15: 7401-7416.

Edwards D, et al. (2010) Addition of glutamate to serum-free culture promotes recovery of electrical activity in adult hippocampal neurons in vitro. J Neurosci Methods. 190: 155-163.

Egert U, et al. (1998) A novel organotypic long-term culture of the rat hippocampus on substrate-integrated multielectrode arrays. Brain Res Brain Res Protoc. 2: 229-242.

Egert U, et al. (2006) Analysis of cardiac myocyte activity dynamics with microeletrode arrays. In: Taketani M BM, editor. Advances m netwrok electrophysiology using multi electrode arrays: Springer 2006. p. 274-290.

Eisen A and Swash M. (2001) Clinical neurophysiology of ALS. Clin Neurophysiol. 112: 2190-2201.

Eisenberg T, et al. (2009) Induction of autophagy by spermidine promotes longevity. Nat Cell Biol. 11: 1305-1314.

Eldridge CF, et al. (1989) Differentiation of axon-related Schwann cells in vitro: II. Control of myelin formation by basal lamina. J Neurosci. 9: 625-638.

Elia D, et al. (2007) Sonic hedgehog promotes proliferation and differentiation of adult muscle cells: Involvement of MAPK/ERK and PI3K/ Akt pathways. Biochim Biophys Acta. 1773: 1438-1446.

Emery AEH. (2002) The muscular dystrophies. Lancet. 359: 687-695.

Engler AJ, et al. (2006) Matrix elasticity directs stem cell lineage specification. Cell. 126: 677-689.

English AW. (2003) Cytokines, growth factors and sprouting at the neuromuscular junction. J Neurocytol. 32: 943-960.

Entcheva EK, et al. (2004) Fluorescence imaging of electrical activity in cardiac cells using an all-solid-state system. IEEE Trans Biomed Eng. 51: 331-341.

Ericson J, et al. (1992) Early stages of motor neuron differentiation revealed by expression ofhomeobox gene Islet-I. Science. 256: 1555-1560.

Esch MB, et al. (2011) The role of body-on-a-chip devices in drug and toxicity studies. Annu Rev Biomed Eng. 13: 55-72.

Esch MB, et al. (2012) On chip porous polymer membranes for integration of gastrointestinal tract epithelium with microfluidic 'body-on-a-chip' devices. Biomed Microdevices. 14: 895-906.

Eschenhagen T and Zimmermann WH. (2005) Engineering myocardial tissue. Circ Res. 97: 1220-1231.

Evans MS, et al. (1998) Electrophysiology of embryonic, adult and aged rat hippocampal neurons in serum-free culture. J Neurosci Methods. 79: 37-46.

Fan CM and Tessier-Lavigne M. (1994) Patterning of mammalian somites by surface ectoderm and notochord: evidence for sclerotome induction by a hedgehog homolog. Cell. 79: 1175-1186.

Faraut B, et al. (2004) Thrombin reduces MuSK and acetylcholine receptor expression along with neuromuscular contact size in vitro. Eur J Neurosci. 19: 2099-2108.

FDA (2004) Innovation or Stagnation: Challenge and Opportunity on the Critical Path to New Medical Products.

Fernandez-Valle C, et al. (1993) Expression of the protein zero myelin gene in axon-related Schwann cells is linked to basal lamina formation. Development. 119: 867-880.

Fernandez-Valle C, et al. (1995) Schwann cells degrade myelin and proliferate in the absence of macrophages: evidence from in vitro studies of Wallerian degeneration. J Neurocytol. 24: 667-679.

Fields GB, et al. (1998) Protein-like molecular architecture: biomaterial applications for inducing cellular receptor binding and signal transduction. Biopolymers. 47: 143-151.

Fields GB. (1999) Induction of protein-like molecular architecture by selfassembly processes. Bioorg Med Chem. 7: 75-81.

Figenschou A, et al. (1996) Cholinergic modulation of the action potential in rat hippocampal neurons. Eur J Neurosci. 8: 211-219.

Fink CC, et al. (1999) Determination of time-dependent inositol-1,4,5-trisphosphate concentrations during calcium release in a smooth muscle cell. Biophys J. 77: 617-628.

Fischbach GD and Cohen SA. (1973) The distribution of acetylcholine sensitivity over uninnervated and innervated muscle fibers grown in cell culture. Dev Biol. 31: 147-162.

Fischbach GD. (1972) Synapse formation between dissociated nerve and muscle cells in low density cell cultures. Dev Biol. 28: 407-429.

Fisher OZ, et al. (2010) Bioinspired materials for controlling stem cell fate. Ace Chem Res. 43: 419-428.

Fishman RA. (2002) The cerebrospinal fluid production rate is reduced in dementia of the Alzheimer's type. Neurology. 58: 1866; author reply 1866.

Flucher BE, et al. (1990) Localization of the alpha 1 and alpha 2 subunits of the dihydropyridine receptor and ankyrin in skeletal muscle triads. Neuron. 5:339-351.

Flucher BE, et al. (1991) Biogenesis of transverse tubules in skeletal muscle in vitro. Dev Biol. 145: 77-90.

Flucher BE, et al. (1992) Coordinated development of myofibrils, sarcoplasmic reticulum and transverse tubules in normal and dysgenic mouse skeletal muscle, in vivo and in vitro. Dev Biol. 150: 266-280.

Flucher BE, et al. (1994) Molecular organization of transverse tubule/sarcoplasmic reticulum junctions during development of excitationcontraction coupling in skeletal muscle. Mol Biol Cell. 5: 1105-1118.

Forry SP, et al. (2006) Facilitating the culture of mammalian nerve cells with polyelectrolyte multilayers. Langmuir. 22: 5770-5775.

Foster RF, et al. (1987) A laminin substrate promotes myogenesis in rat skeletal muscle cultures: analysis of replication and development using antidesmin and anti-BrdUrd monoclonal antibodies. Dev Biol. 122: 11-20.

Fowler VM, et al. (1993) Tropomodulin is associated with the free (pointed) ends of the thin filaments in rat skeletal muscle. J Cell Biol. 120: 411-420.

Fox MA, et al. (2007) Distinct target-derived signals orgamze formation, maturation, and maintenance of motor nerve terminals. Cell. 129: 179-193.

Francis PT. (2008) Glutamatergic approaches to the treatment of cognitive and behavioural symptoms of Alzheimer's disease. Neurodegener Dis. 5: 241-243.

(56) References Cited

OTHER PUBLICATIONS

Frank E and Fischbach GD. (1979) Early events in neuromuscular junction formation in vitro: induction of acetylcholine receptor clusters in the postsynaptic membrane and morphology of newly formed synapses. J Cell Biol. 83: 143-158.
Franzini-Armstrong C and Protasi F. (1997) Ryanodine receptors of striated muscles: a complex channel capable of multiple interactions. Physiol Rev. 77: 699-729.
Friedman B, et al. (1995) BDNF and NT-4/5 exert neurotrophic influences on injured adult spinal motor neurons. J Neurosci. 15: 1044-1056.
Fu X, et al. (1995) Acidic fibroblast growth factor reduces rat skeletal muscle damage caused by ischemia and reperfusion. Chin Med J (Engl). 108: 209-214.
Fuentes-Medel Y, et al. (2012) Integration of a retrograde signal during synapse formation by glia-secreted TGF-B ligand. Curr Biol. 22: 1831-1838.
Funakoshi H, et al. (1995) Muscle-derived neurotrophin-4 as an activitydependent trophic signal for adult motor neurons. Science. 268: 1495-1499.
Gajsek N, et al. (2006) Expression of MuSK in in vitro-innervated human muscle. J Mol Neurosci. 30: 27-28.
Gajsek N, et al. (2008) Synaptogenetic mechanisms controlling postsynaptic differentiation of the neuromuscular junction are nerve-dependent in human and nerve-independent in mouse C2C12 muscle cultures. Chem Biol Interact. 175:50-57.
Galizia CG and Menzel R. (2000) Probing the olfactory code. Nat Neurosci. 3: 853-854.
Gao BX and Ziskind-Conhaim L. (1995) Development of glycine- and GABAgated currents in rat spinal motoneurons. J Neurophysiol. 74: 113-121.
Gao Bx and Ziskind-Conhaim L. (1998) Development of ionic currents underlying changes in action potential waveforms in rat spinal motoneurons. J Neurophysiol. 80: 3047-3061.
Gao J, et al. (2005) Human neural stem cell-derived cholinergic neurons innervate muscle in motoneuron deficient adult rats. Neuroscience. 131: 257-262.
Garcez RC, et al. (2009) Epidermal growth factor (EGF) promotes the in vitro differentiation of neural crest cells to neurons and melanocytes. Cell Mol Neurobiol. 29: 1087-1091.
Garell PC, et al. (1998) Introductory overview of research instruments for recording the electrical activity of neurons in the human brain. Rev Sci Instrum. 69:4027-4037.
Gaud A, et al. (2004) Prednisone reduces muscle degeneration in dystrophindeficient Caenorhabditis elegans. Neuromuscul Disord. 14: 365-370.
Gaztañaga, L., Marchlinski, F. E., & Betensky, B. P. (2012). Mechanisms of cardiac arrhythmias. Revista Española de Cardiología (English Edition), 65(2), 174-185.
Georger JH, et al. (1992) Coplanar patterns of self-assembled monolayers for selective cell adhesion and outgrowth. Thin Solid Films. 210: 716-719.
Germani A, et al. (2003) Vascular endothelial growth factor modulates skeletal myoblast function. Am J Pathol. 163: 1417-1428.
Gerrard L, et al. (2005) Differentiation of human embryonic stem cells to neural lineages in adherent culture by blocking bone morphogenetic protein signaling. Stem Cells. 23: 1234-1241.
Ghiani CA, et al. (1999) Neurotransmitter receptor activation triggers p27(Kipl) and p21(CIP 1) accumulation and G 1 cell cycle arrest in oligodendrocyte progenitors. Development. 126: 1077-1090.
Ginsberg SD. (2005) Glutamatergic neurotransmission expression profiling in the mouse hippocampus after perforant-path transection. Am J Geriatr Psychiatry. 13: 1052-1061.
Glass Land Kauffman SA. (1973) The logical analysis of continuous, non-linear biochemical control networks. J Theor Biol. 39: 103-129.
Glass L. ( 197 5) Classification of biological networks by their qualitative dynamics. J Theor Biol. 54: 85-107.
Glass, D. J. (2003). Signalling pathways that mediate skeletal muscle hypertrophy and atrophy. Nat Cell Biol. 5: 87-90.
Golan H, et al. (2000) GABA withdrawal modifies network activity in cultured hippocampal neurons. Neural Plast. 7: 31-42.
Gold MR. (1982) The effects of vasoactive intestinal peptide on neuromuscular transmission in the frog. J Physiol. 327: 325-335.
Golden JP, et al. (1999) Expression of neurturin, GDNF, and GDNF family-receptor mRNA in the developing and mature mouse. Exp Neurol. 158: 504-528.
Gonzalez AM, et al. (1990) Distribution of basic fibroblast growth factor in the 18-day rat fetus: localization in the basement membranes of diverse tissues. J Cell Biol. 110: 753- 765.
Goodyear S and Sharma MC. (2007) Roscovitine regulates invasive breast cancer cell (MDA-MB231) proliferation and survival through cell cycle regulatory protein cdk5. Exp Mol Pathol. 82: 25-32.
Goodyear S. (2005) Roscovitine induced cell death is mediated through specific inhibition of cell cycle regulatory protein cdk5. AACR Meeting Abstracts. 1045-d-1046.
Gordon AM, et al. (2000) Regulation of Contraction in Striated Muscle. Physiol Rev. 80: 853-924.
Goritz C, et al. (2005) Multiple mechanisms mediate cholesterol-induced synaptogenesis in a CNS neuron. Mol Cell Neurosci. 29: 190-201.
Gozes I, et al. (2004) NAP mechanisms of neuroprotection. J Mol Neurosci. 24: 67-72.
Graham SC, et al. (1992) Enzyme and size profiles in chronically inactive cat soleus muscle fibers. Muscle Nerve 15: 27-36.
Gramowski A, et al. (2006) Functional screening of traditional antidepressants with primary cortical neuronal networks grown on multielectrode neurochips. Eur J Neurosci. 24: 455-465.
Granchelli JA, et al. (2000) Pre-clinical screening of drugs using the mdx mouse. Neuromuscul Disord. 10: 235-239.
Greaves P, et al. (2004) First dose of potential new medicines to humans: how animals help. Nat Rev Drug Discov. 3: 226-236.
Greenstein JL and Winslow RL. (2002) An integrative model of the cardiac ventricular myocyte incorporating local control of Ca2+ release. Biophys J. 83:2918-2945.
Greenwood AL, et al. (1999) Identification of dividing, determined sensory neuron precursors in the mammalian neural crest. Development. 126: 3545-3559.
Gross GW, et al. (1993) Stimulation of monolayer networks in culture through thin-film indium-tin oxide recording electrodes. J Neurosci Methods. 50: 131-143.
Gross GW, et al. (1995) The Use of Neuronal Networks on Multielectrode Arrays as Biosensors. Biosens Bioelectron. 10: 553-567.
Gross GW, et al. (1997) Odor, drug and toxin analysis with neuronal networks in vitro: extracellular array recording of network responses. Biosens Bioelectron. 12: 373-393.
Groves MJ and Scaravelli F. (2005) Chapter 31—Pathology of Peripheral Neuron Cell Bodies. In: Dyck, PJ and Thomas, PK, (eds.) Peripheral neuropathy. 683-732. Elsevier Saunders: Philadelphia.
Grubic Z, et al. (1995) Myoblast fusion and innervation with rat motor nerve alter distribution of acetylcholinesterase and its mRNA in cultures of human muscle. Neuron. 14: 317-327.
Guenou H, et al. (2009) Human embryonic stem-cell derivatives for full reconstruction of the pluristratified epidermis: a preclinical study. Lancet. 374:1745-175.
Guettier-Sigrist S, et al. (1998) Muscle could be the therapeutic target in SMA treatment. J Neurosci Res. 53: 663-669.
Guettier-Sigrist S, et al. (2000) Cell types required to efficiently innervate human muscle cells in vitro. Exp Cell Res. 259: 204-212.
Gullberg D, et al. (1995) Analysis of fibronectin and vitronectin receptors on human fetal skeletal muscle cells upon differentiation. Exp Cell Res. 220: 112-123.
Guo JZ, et al. (2005) Synaptically released and exogenous ACh activates different nicotinic receptors to enhance evoked glutamatergic transmission in the lateral geniculate nucleus. J Neurophysiol. 94: 2549-2560.
Guo X, et al. (2011) Neuromuscular junction formation between human stem cell-derived motoneurons and human skeletal muscle in a defined system. Biomaterials. 32: 9602-9611.

(56) References Cited

OTHER PUBLICATIONS

Guo X, et al. (2012) Tissue engineering the monosynaptic circuit of the stretch reflex arc with co-culture of embryonic motoneurons and proprioceptive sensory neurons. Biomaterials. 33: 5723-5731.
Guo X, et al. (2013) Derivation of sensory neurons and neural crest stem cells from human neural progenitor hNP1. Biomaterials. 34: 4418-4427.
Guo XF, et al. (2010a) Characterization of a human fetal spinal cord stem cell line, NSI-566RSC, and its induction to functional motoneurons. J Tissue Eng Regen Med. 4: 181-193.
Guo XF, et al. (2010b) Neuromuscular junction formation between human stem-cell-derived motoneurons and rat skeletal muscle in a defined system. Tissue Eng Part C Methods. 16: 1347-1355.
Gupta S, et al. (2007) Boolean network analysis of a neurotransmitter signaling pathway. J Theor Biol. 244: 463-469.
Gureviciene I, et al. (2004) Normal induction but accelerated decay of LTP in APP+ PSI transgenic mice. Neurobiol Dis. 15: 188-195.
Haas HL and Selbach 0. (2000) Functions of neuronal adenosine receptors. Naunyn Schmiedebergs Arch Pharmacol. 362: 375-381.
Halbach M, et al. (2003) Estimation of action potential changes from field potential recordings in multicellular mouse cardiac myocyte cultures. Cell Physiol Biochem. 13: 271-284.
Hall BK and Miyake T. (2000) All for one and one for all: condensations and the initiation of skeletal development. Bioessays. 22: 138-147.
Hamaguchi T, et al. (2006) Anti-amyloidogenic therapies: strategies for prevention and treatment of Alzheimer's disease. Cell Mol Life Sci. 63: 1538-1552.
Hammarback JA, et al. (1985) Guidance of neurite outgrowth by pathways of substratum-adsorbed laminin. J Neurosci Res. 13: 213-220.
Han DK and Hubbell JA. (1997) Synthesis of Polymer Network Scaffolds from 1-Lactide and Poly( ethylene glycol) and Their Interaction with Cells. Macromolecules. 30: 607-6083.
Hantai D, et al. (1991) Developmental appearance of thrombospondin in neonatal mouse skeletal muscle. Eur J Cell Biol. 55: 286-294.
Harding SE, et al. (2007) The human embryonic stem cell-derived cardiomyocyte as a pharmacological model. Pharmacol Ther. 113: 341-353.
Hardy J and Selkoe DJ. (2002) The amyloid hypothesis of Alzheimer's disease: progress and problems on the road to therapeutics. Science. 297: 353-356.
Hari L, et al. (2002) Lineage-specific requirements of beta-catenin in neural crest development. J Cell Biol. 159: 867-880.
Harms H, et al. (2006) Whole-cell living biosensors—are they ready for environmental application? Appl Microbiol Biotechnol. 70: 273-280.
Harper JM, et al. (2004) Axonal growth of embryonic stem cell-derived motoneurons in vitro and in motoneuron-injured adult rats. Proc Natl Acad Sci U s A. 101: 7123-7128.
Harsch A, et al. (1997) Strychnine analysis with neuronal networks in vitro: extracellular array recording of network responses. Biosens Bioelectron. 12: 827-835.
Heiduschka P and Thanos S. (1998) Implantable bioelectric interfaces for lost nerve functions. Prog Neurobiol. 55: 433-461.
Heinrich G. (2003) A novel BDNF gene promoter directs expression to skeletal muscle. BMC Neurosci. 4: 11.
Henderson CE, et al. (1993) Neurotrophins promote motor neuron survival and are present in embryonic limb bud. Nature. 363: 266-270.
Henderson CE, et al. (1994) GDNF: a potent survival factor for motoneurons present in peripheral nerve and muscle. Science. 266: 1062-1064.
Hennessey JV, et al. (1997) Increase in percutaneous muscle biopsy yield with a suction- enhancement technique. J Appl Physiol. 82: 1739-1742.
Hennessey N, et al. (2001) Growth hormone administration and exercise effects on muscle fiber type and diameter in moderately frail older people. J Am Geriatr Soc. 49: 852-858.
Hermann M, et al. (2006) Exposure of atorvastatin is unchanged but lactone and acid metabolites are increased several-fold in patients withatorvastatin-induced myopathy. Clin Pharmacol Ther. 79: 532-539.
Herrup K and Yang Y. (2007) Cell cycle regulation in the postmitotic neuron: oxymoron or new biology? Nat Rev Neurosci. 8: 368-378.
Hickman J, et al. ( 1993) The use of monlayers as templates for biocompatibility studies. Abstracts of Papers of the American Chemical Society. 205: 146-Coll.
Hickman J. (2005) Building Minimalistic Hybrid Neuroelectric Devices in Toward Replacement Parts for the Brain: Implantable Biomimetic Electronics as Neural Prosthetic (T.W. Berger and D.L. Glanzman Eds.), 1st edition. Cambridge, MA: MIT Press.
Hickman JJ, et al. (1994) Rational Pattern Design for in-Vitro Cellular Networks Using Surface Photochemistry. J Vac Science Technol A. 12: 607-616.
Hirano A. ( 1968) A confirmation of the oligodendroglial origin of myelin in the adult rat. J Cell Biol. 38: 637-640.
Hjerling-Leffler J, et al. (2005) The boundary cap: a source of neural crest stem cells that generate multiple sensory neuron subtypes. Development. 132: 2623-2632.
Hoffman EP and Escolar D. (2006) Translating mighty mice into neuromuscular therapeutics: is bigger muscle better? Am J Pathol. 168: 177 5-1778.
Hoffmann F and Bading H. (2006) Long term recordings with microelectrode arrays: studies of transcription-dependent neuronal plasticity and axonal regeneration. J Physiol Paris. 99: 125-132.
Holleran AL, et al. (1995) Glutamine metabolism in AS-30D hepatoma cells. Evidence for its conversion into lipids via reductive carboxylation. Mol Cell Biochem. 152: 95-101.
Hondeghem LM and Hoffinan P. (2003b) Blinded test in isolated female rabbit heart reliably identifies action potential duration prolongation and proarrhythmic drugs: importance of triangulation, reverse use dependence, and instability. J Cardiovasc Pharmacol. 41: 14-24.
Hondeghem LM, et al. (2001) Instability and triangulation of the action potential predict serious proarrhythmia, but action potential duration prolongation is antiarrhythmic. Circulation. 103: 2004-2013.
Hondeghem LM, et al. (2003a) Detection of proarrhythmia in the female rabbit heart: blinded validation. J Cardiovasc Electrophysiol. 14: 287-29.
Hondeghem LM. (2006) Thorough QT/QTc not so thorough: removes torsadogenic predictors from the T-wave, incriminates safe drugs, and misses profibrillatory drugs. J Cardiovasc Electrophysiol. 17: 337-340.
Hondeghem LM. (2007) Relative contributions of TRiaD and QT to proarrhythmia. J Cardiovasc Electrophysiol. 18: 655-657.
Hsiao CF, et al. (2005) Voltage-dependent calcium currents in trigeminal motoneurons of early postnatal rats: modulation by 5-HT receptors. J Neurophysiol. 94: 2063-2072.
Hu BY, et al. (2009) Human oligodendrocytes from embryonic stem cells: conserved SHH signaling networks and divergent FGF effects. Development. 136: 1443-1452.
Hua JY and Smth SJ. (2004) Neural activity and the dynamics of central nervous system development. Nat Neurosci. 7: 327-332.
Huang Y, et al. (2007) An alphalA-adrenergic-extracellular signal-regulated kinase survival signaling pathway in cardiac myocytes. Circulation. 115: 763-772.
Huang YC, et al. (2005) Rapid formation of functional muscle in vitro using fibrin gels. J Appl Physiol. 98: 706-713.
Hucka M, et al. (2003) The systems biology markup language (SBML): a medium for representation and exchange of biochemical network models. Bioinformatics. 19: 524-531.
Hughes B. (2008) 2007 FDA drug approvals: a year of flux. Nat Rev Drug Discov. 7: 107-109.
Huh D, et al. (2010) Reconstituting organ-level lung functions on a chip. Science. 328: 1662-1668.
Huh D, et al. (2012) Microengineered physiological biomimicry: organs-onchips. Lab Chip. 12: 2156-2164.
Hui EE and Bhatia SN. (2007) Microscale control of cell contact and spacing via three-component surface patterning. Langmuir. 23: 4103-4107.

(56) References Cited

OTHER PUBLICATIONS

Hung SC, et al. (2002) In vitro differentiation of size-sieved stem cells into electrically active neural cells. Stem Cells. 20: 522-529.
Husmann I, et al. (1996) Growth factors in skeletal muscle regeneration. Cytokine Growth Factor Rev. 7: 249-258.
Huxley, A. F. (1975). The origin of force in skeletal muscle. Ciba Found Symp. 31: 271-290.
Ichikawa H, et al. (2004) Effect of Bm-3a deficiency on parvalbumin-immunoreactive primary sensory neurons in the dorsal root ganglion. Brain Res Dev Brain Res. 150: 41-45.
Inoue N, et al. (2004) Rapid electrical stimulation of contraction modulates gap junction protein m neonatal rat cultured cardiomyocytes: involvement of mitogen-activated protein kinases and effects of angiotensin II-receptor antagonist. J Am Coll Cardiol. 44: 914-922.
Iravanian S, et al. (2003) Functional reentry in cultured monolayers of neonatal rat cardiac cells. Am J Physiol Heart Circ Physiol. 285: H449-H456.
Ito Y. (1999) Surface micropatterning to regulate cell functions. Biomaterials. 20:2333-2342.
Izrael M, et al. (2007) Human oligodendrocytes derived from embryonic stem cells: Effect of noggin on phenotypic differentiation in vitro and on myelination in vivo. Mol Cell Neurosci. 34: 310-323.
Izumiya Y, et al. (2008) Fast/glycolytic muscle fiber growth reduces fat mass and improves metabolic parameters in obese mice. Cell Metabolism. 7: 159-172.
Jackson JH 4th, et al. (2004) Assessment of drug therapy management and the prevalence of heart failure in a managed care population with hypertension. J Manag Care Pharm. 10: 513-520.
Jaworska-Wilczynska M, et al. (2002) Three lipoprotein receptors and cholesterol in inclusion-body myositis muscle. Neurology. 58: 438-445.
Jensen J, et al. (2009) Human embryonic stem cell technologies and drug discovery. J Cell Physiol. 219: 513-519.
Jessen KR and Mirsky R. (2005) The origin and development of glial cells in peripheral nerves. Nat Rev Neurosci. 6: 671-682.
Jevsek M, et al. (2004) Origin of acetylcholinesterase in the neuromuscular junction formed in the in vitro innervated human muscle. Eur J Neurosci. 20:2865-2871.
Jhamandas JH, et al. (2001) Cellular mechanisms for amyloid beta-protein activation of rat cholinergic basal forebrain neurons. J Neurophysiol. 86: 1312-1320.
Jiang XH, et al. (2009) Isolation and characterization of neural crest stem cells derived from in vitro-differentiated human embryonic stem cells. Stem Cells Dev. 18: 1059-1070.
Jiang Z and Clemens PR. (2006) Cellular caspase-8-like inhibitory protein (cFLIP) prevents inhibition of muscle cell differentiation induced by cancer cells. Faseb J. 20: 2570-2572.
Jiang ZG, et al. (1990) Excitatory and inhibitory transmission from dorsal root afferents to neonate rat motoneurons in vitro. Brain Res. 535: 110-118.
Jin P, et al. (1991) Recombinant platelet-derived growth factor-BB stimulates growth and inhibits differentiation of rat L6 myoblasts. J Biol Chem. 266: 1245-1249.
Johnson TE, et al. (2005) Statins and PP ARalpha agonists induce myotoxicity in differentiated rat skeletal muscle cultures but do not exhibit synergy with cotreatment. Toxicol Appl Pharmacol. 208: 210-221.
Julius D and Basbaum AL. (2001) Molecular mechanisms of nociception. Nature. 413: 203-210.
Jung DR, et al. (1998) Cell-Based Sensor Microelectrode Array Characterized by Imaging X-ray Photoelectron Spectroscopy, Scanning Electron Microscopy, Impedance Measurements, and Extracellular Recordings. Journal of Vacuum Science & Technology A (Vacuum, Surfaces, and Films). 16: 1183-1188.
Jung DR, et al. (2001) Topographical and physicochemical modification of material surface to enable patterning of living cells. Crit Rev Biotechnol. 21: 111-154.
Jurdana M, et al. (2009) Neural agrin changes the electrical properties of developing human skeletal muscle cells. Cell Mol Neurobiol. 29: 123-131.
Kaeberlein M. (2009) Spermidine surprise for a long life. Nat Cell Biol. 11:1277-1278.
Kaji H, et al. (2003) Pharmacological characterization of micropatterned cardiac myocytes. Biomaterials. 24: 4239-4244.
Kamp TJ. (2009) Human pluripotent stem cell-derived cardiomyocytes for safety pharmacology applications. Journal of Pharmacological and Toxicological Methods. 60: 259.
Kane RS, et al. (1999) Patterning proteins and cells using soft lithography. Biomaterials. 20: 2363-2376.
Kang JH, et al. (2009) In vitro 3D model for human vascularized adipose tissue. Tissue Eng Part A. 15: 2227-2236.
Kato AC and Lindsay RM. (1994) Overlapping and additive effects of neurotrophins and CNTF on cultured human spinal cord neurons. Exp Neurol. 130: 196-20.
Katsuki H, et al. (2000) Distinct signaling pathways involved in multiple effects of basic fibroblast growth factor on cultured rat hippocampal neurons. Brain Res. 885: 240-250.
Katz LC and Shatz CJ. (1996) Synaptic activity and the construction of cortical circuits. 274: 1133-1138.
Kauffman S, et al. (2003) Random Boolean network models and the yeast transcriptional network. Proc Natl Acad Sci US A. 100: 14796-14799.
Kauffman S. (1971) Gene regulation networks: a theory for their global structure and behaviors. Curr Top Dev Biol. 6: 145-182.
Kaufmann P, et al. (2006) Toxicity of statins on rat skeletal muscle mitochondria. Cell Mol Life Sci. 63: 2415-2425.
Keefer EW, et al. (2001a) Acute toxicity screening of novel AChE inhibitors using neuronal networks on microelectrode arrays. Neurotoxicology. 22: 3-1.
Keefer EW, et al. (2001b) Characterization of acute neurotoxic effects of trimethylolpropane phosphate via neuronal network biosensors. Biosens Bioelectron. 16: 513-525.
Kessaris N, et al. (2008) Specification of CNS glia from neural stem cells in the embryonic neuroepithelium. Philos Trans R Soc Lond B Biol Sci. 363: 71-85.
Khademhosseini A, et al. (2006a) Interplay of biomaterials and micro-scale technologies for advancing biomedical applications. J Biomater Sci Polym Ed. 17: 1221-1240.
Khademhosseini A, et al. (2006b) Microscale technologies for tissue engineering and biology. Proc Natl Acad Sci USA. 103: 2480-2487.
Khorchid A, et al. (1999) Characterization of the signal transduction pathways mediating noradrenaline-stimulated MAPK activation and c-fos expression in oligodendrocyte progenitors. JNeurosci Res. 58: 765-778.
Khorchid A, et al. (2002) Developmental regulation of alpha IA-adrenoceptor function in rat brain oligodendrocyte cultures. Neuropharmacology. 42: 685-696.
Kidambi S, et al. (2004) Controlling primary hepatocyte adhesion and spreading on protein-free polyelectrolyte multilayer films. J Am Chem Soc. 126: 16286-16287.
Kidambi S, et al. (2007a) Patterned co-culture of primary hepatocytes and fibroblasts using polyelectrolyte multilayer templates. Macromol Biosci. 7: 344-353.
Kidambi S, et al. (2007b) Cell adhesion on polyelectrolyte multilayer coated polydimethylsiloxane surfaces with varying topographies. Tissue Eng. 13: 2105-2117.
Kidd, J. (2006). Life after statin patent expiries. Nat Rev Drug Discov. 5: 813-814.
Kim C, et al. (2010) Non-cardiomyocytes influence the electrophysiological maturation of human embryonic stem cell-derived cardiomyocytes during differentiation. Stem Cells Dev. 19: 783-795.
Kim D-H, et al. (2005) Modulation of adhesion and growth of cardiac myocytes by surface nanotopography. Proceedings of the 2005 IEEE. Engineering in Medicine and Biology 27th Annual Conference. Shanghai, China, Sep. 1-4, 2005.
Kim J, et al. (2002) Dopamine neurons derived from embryonic stem cells function in an animal model of Parkinson's disease. Nature. 418: 50-56.
Kim K, et al. (2011) Calibrated micropost arrays for biomechanical characterization of cardiomyocytes. Micro and Nano Letters. 6: 317-322.

(56) References Cited

OTHER PUBLICATIONS

Kim SU, et al. (2002) Production of immortalized human neural crest stem cells. Methods Mol Biol. 198: 55-65.
Kim, Jinseok, et al. "Biohybrid microsystems actuated by cardiomyocytes: microcantilever, microrobot, and micropump." Robotics and Automation, 2008. ICRA 2008. IEEE International Conference on. IEEE, 2008.
Kim, IEEE poster. Micropatterning of Cardiomyocytes Using Adhesion-Resistant Polymeric Microstructures, The 13th International Conference on Solid-State Sensors, Actuators and Microsystems, Seoul, Korea, Jun. 5-9, 2005.
King T, et al. (2000) Piezoactuators for 'real-world' applications—Can they deliver sufficient displacement? Power Engineering. 14: 105-110.
Kingshott P and Griesser HJ. (1999) Surfaces that resist bioadhesion. Current Opinion in Solid State and Materials Science. 4: 403-412.
Kirazov E, et al. (2008) Amyloid beta peptides exhibit functional neurotoxicity to cortical network cultures. Compt Rend Acad Bulg Sci. 61: 905-910.
Kita-Matsuo H, et al. (2009) Lentiviral vectors and protocols for creation of stable hESC lines for fluorescent tracking and drug resistance selection of cardiomyocytes. PLoS One. 4: e5046.
Kleber AG and Rudy Y. (2004) Basic mechanisms of cardiac impulse propagation and associated arrhythmias. Physiol Rev. 84: 431-488.
Klein C, et al. (2002) Zinc inhibition of cAMP signaling. J Biol Chem. 277: 11859-11865.
Klein WL. (2002) Abeta toxicity in Alzheimer's disease: globular oligomers (ADDLs) as new vaccine and drug targets. Neurochem Int. 41: 345-352.
Kleinfeld D, et al. (1988) Controlled outgrowth of dissociated neurons on patterned substrates. J Neurosci. 8: 4098-4120.
Knobloch M and Mansuy IM. (2008) Dendritic spine loss and synaptic alterations in Alzheimer's disease. Mol Neurobiol. 37: 73-82.
Kobayashi T, et al. (1985) Acetylcholine receptors and acetylcholinesterase accumulate at the nerve-muscle contacts of de novo grown human monolayer muscle cocultured with fetal rat spinal cord. Exp Neurol. 88: 327-335.
Kobayashi T, et al. (1987) Human muscle cultured in monolayer and cocultured with fetal rat spinal cord: importance of dorsal root ganglia for achieving successful functional innervation. JNeurosci. 7: 3131-3141.
Koike T, et al. (2008) Axon & dendrite degeneration: its mechanisms and protective experimental paradigms. Neurochem Int. 52: 751-760.
Koirala S, et al. (2003) Roles of glial cells in the formation, function, and maintenance of the neuromuscular junction. J Neurocytol. 32: 987-1002.
Koleva M, et al. (2005) Pleiotropic effects of sonic hedgehog on muscle satellite cells. Cell Mol Life Sci. 62: 1863-1870.
Koliatsos VE, et al. (2008) Human stem cell grafts as therapies for motor neuron disease. Expert Opin Biol Ther. 8: 137-141.
Kontrogianni-Konstantopoulos A, et al. (2009) Muscle giants: molecular scaffolds in sarcomerogenesis. Physiol Rev. 89: 1217-1267.
Kornblum HI, et al. (1999) Multiple trophic actions of heparin-binding epidermal A511. growth factor (HB-EGF) in the central nervous system. Eur J Neurosci. 11: 3236-3246.
Kucera J and Dorovini-Zis K. (1979). Types of human intrafusal muscle fibers. Muscle Nerve. 2: 437-451.
Kucera J and Walro J. (1992) Axotomy induces fusimotor-free muscle spindles in neonatal rats. Neurosci Lett. 136: 216-218.
Kucera J, et al. (1989) Role of nerve and muscle factors in the development of rat muscle spindles. Am J Anat. 186: 144-160.
Kucera J. (1982a) One-bag-fiber muscle spindles in tenuissimus muscles of the cat. Histochemistry and Cell Biology. 76: 315-328.
Kucera, J. (1982b). The topography of long nuclear chain intrafusal fibers in the cat muscle spindle. Histochemistry. 74: 183-197.
Kucera, J. (1983). Multiple-bag-fiber muscle spindles in tenuissimus muscles of the cat. Histochemistry. 79: 457-476.
Kudla AJ, et al. (1995) A requirement for fibroblast growth factor in regulation of A518. skeletal muscle growth and differentiation cannot be replaced by activation of platelet-derived growth factor signaling pathways. Mol Cell Biol. 15: 3238-3246.
Kuhl U, et al. (1982) Synthesis of type IV collagen and laminin in cultures of skeletal muscle cells and their assembly on the surface of myotubes. Dev Biol. 93: 344-354.
Kuhl U, et al. (1986) Role of laminin and fibronectin in selecting myogenic versus fibrogenic cells from skeletal muscle cells in vitro. Dev Biol. 117: 628-635.
Kumar S, et al. (1998) NT-3-mediated TrkC receptor activation promotes proliferation and cell survival of rodent progenitor oligodendrocyte cells in vitro and in vivo. J Neurosci Res. 54: 754-765.
Kurek JB, et al. (1996) Leukemia inhibitory factor and interleukin-6 are produced by diseased and regenerating skeletal muscle. Muscle Nerve. 19: 1291-1301.
Lacor PN, et al. (2007a) Abeta oligomer-induced aberrations m synapse composition, shape, and density provide a molecular basis for loss of connectivity in Alzheimer's disease. J Neurosci. 27: 796-807.
Lacor PN. (2007b) Advances on the understanding of the origins of synaptic pathology in AD. Curr Genomics. 8: 486-508.
Laflamme MA, et al. (2007) Cardiomyocytes derived from human embryonic stem cells in pro-survival factors enhance function of infarcted rat hearts. Nat Biotechnol. 25: 1015-1024.
Lamb TM, et al. (1993) Neural induction by the secreted polypeptide noggin. Science. 262: 713-718.
Lambert MP, et al. (1998) Diffusible, nonfibrillar ligands derived from Abeta1-42 are potent central nervous system neurotoxins. Proc Natl Acad Sci US A. 95:6448-6453.
Lambeth MJ and Kushmerick MJ. (2002) A computational model for glycogenolvsis in skeletal muscle. Ann Biomed Eng. 30: 808-827.
Lambrechts D, et al. (2003) VEGF is a modifier of amyotrophic lateral sclerosis in mice and humans and protects motoneurons against ischemic death. Nat Genet. 34: 383-394.
Langen RC, et al. (2003) Enhanced myogenic differentiation by extracellular matrix is regulated at the early stages of myogenesis. In Vitro Cell Dev Biol Anim. 39: 163-169.
Langer Rand Vacanti JP. (1993) Tissue engineering. Science. 260: 920-926.
Larkin LM, et al. (2006) Functional evaluation of nerve-skeletal muscle constructs engineered in vitro. In Vitro Cell Dev Biol Anim. 42: 75-82.
Larsson L and Ansved T. (1995) Effects of ageing on the motor unit. Prog Neurobiol. 45: 397-415.
Lasser KE, et al. (2002) Timing of new black box warnings and withdrawals for prescription medications. JAMA. 287: 2215-2220.
Lawrence CL, et al. (2005) Nonclinical proarrhythmia models: predicting Torsades de Pointes. J Pharmacol Toxicol Methods. 52: 46-59.
Lawrence CL, et al. (2006) A rabbit Langendorff heart proar-rhythmia model: predictive value for clinical identification of Torsades de Pointes. Br J Pharmacol. 149: 845-860.
Le Douarin NM and Dupin E. (2003) Multipotentiality of the neural crest. Curr Opin Genet Dev. 13: 529-536.
Lee A. (2005) Isolation of neural stem cells from the postnatal cerebellum. Nat Neurosci. 8: 723-729.
Lee EW, et al. (2003) Neuropeptide Y induces ischemic angiogenesis and restores function of ischemic skeletal muscles. J Clin Invest. 111: 1853-1862.
Lee G, et al. (2007) Isolation and directed differentiation of neural crest stem cells derived from human embryonic stem cells. Nat Biotechnol. 25: 1468-1475.
Lee G, et al. (2010) Derivation of neural crest cells from human pluripotent stem cells. Nat Protoc. 5: 688-701.
Lee HY, et al. (2004) Instructive role of Wnt/beta-catenin in sensory fate specification in neural crest stem cells. Science. 303: 1020-1023.

(56) References Cited

OTHER PUBLICATIONS

Lee MJ, et al. (2003) Hereditary sensory neuropathy is caused by a mutation in the delta subunit of the cytosolic chaperonin-containing t-complex peptide-I (Cct4) gene. Hum Mol Genet. 12: 1917-1925.
Lesbordes JC, et al. (2002) In vivo electrotransfer of the cardiotrophin-1 gene into skeletal muscle slows down progression of motor neuron degeneration in pmn mice. Hum Mol Genet. 11: 1615-1625.
Lescaudron L, et al. (1999) Blood borne macrophages are essential for the triggering of muscle regeneration following muscle transplant. Neuromuscul Disord. 9: 72-80.
Levenberg S, et al. (2003) Differentiation of human embryonic stem cells on three-dimensional polymer scaffolds. Proc Natl Acad Sci U S A. 100: 12741-12746.
LeVine SM and Goldman JE. (1988) Embryonic divergence of oligodendrocyte and astrocyte lineages in developing rat cerebrum. J Neurosci. 8: 3992-4006.
Li B-S, et al. (2001) Regulation ofNMDA receptors by cyclin-dependent kinase-5 Proc Natl Acad Sci US A. 98: 12742-12747.
Li L and Olson EN. (1992) Regulation of muscle cell growth and differentiation by the MyoD family of helix-loop-helix proteins. Adv Cancer Res. 58: 95-119.
Li M, et al. (2005) Comparison of selective attachment and growth of smooth muscle cells on gelatin- and fibronectin-coated micropatterns. J Nanosci Nanotechnol. 5: 1809-1815.
Li MX, et al. (2001) Opposing actions of protein kinase A and C mediate Hebbian synaptic plasticity. Nat Neurosci. 4: 871-872.
Li S, et al. (2006) Predicting essential components of signal transduction networks: a dynamic model of guard cell abscisic acid signaling. PLoS Biol. 4:e312.
Li XJ, et al. (2005) Specification of motoneurons from human embryonic stem cells. Nat Boltechnol. 23: 215-221.
Lim GP, et al. (2001) The curry spice curcumin reduces oxidative damage and amyloid pathology in an Alzheimer transgenic mouse. J Neurosci. 21: 8370-8377.
Lim UM, et a. (2006) Derivation of Motor Neurons from three Clonal Human Embryonic Stem Cell Lines. CurrNeurovasc Res. 3: 281-288.
Lin JW, et al. (2008) Region of slowed conduction acts as core for spiral wave reentry in cardiac cell monolayers. Am J Physiol Heart Circ Physiol. 294: H58-H65.
Lin LF, et al. (1993) GDNF: a glial cell line-derived neurotrophic factor for midbrain dopaminergic neurons. Science. 260: 1130-1132.
Lipsett MA, et al. (2007) Acinar plasticity: development of a novel in vitro model to study human acinar-to-duct-to-islet differentiation. Pancreas. 34: 452-457.
Lipton SA. (2006) Paradigm shift in neuroprotection by NMDA receptor blockade: Memantine and beyond. Nat Rev Drug Discov. 5: 160-170.
Lisak RP, et al. (1997) The role of cytokines in Schwann cell damage, protection, and repair. J Infect Dis. 176 Suppl 2: S173-S179.
Liu CN, et al. (2000) Spinal nerve injury enhances subthreshold membrane potential oscillations m DRG neurons: relation to neuropathic pam. J Neurophysiol. 84: 205-215.
Liu J, et al. (2008) Electrophysiological and Immunocytochemical Characterization of DRG Neurons on an Organosilane Surface in Serum Free Medium. In Vitro Cell Dev Biol Anim. 44: 162-168.
Liu S, et al. (2000) Embryonic stem cells differentiate into oligodendrocytes and myelinate in culture and after spinal cord transplantation. Proc Natl Acad Sci USA. 97: 6126-6131.
Liu TX, et al. (2006) Blinded validation of the isolated arterially perfused rabbit ventricular wedge in preclinical assessment of drug-induced proarrhythmias. Heart Rhythm. 3: 948- 956.
Liu WP, et al. (2005) Enantioselectivity in environmental safety of current chiral insecticides. Proc Natl Acad Sci US A. 102: 701-706.
Lochter AJ, et al. (1995) Control of neuronal morphology in vitro: interplay between adhesive substrate forces and molecular instruction. J Neurosci Res. 42:145-158.

Long C, et al. (2012) Design optimization of liquid-phase flow patterns for microfabricated lung on a chip. Ann Biomed Eng. 40: 1255-1267.
Lou XJ. (2009) Polarization fatigue in ferroelectric thin films and related materials. Journal of Applied Physics. 105: 024101-024124.
Lou XJ. (2009b) Statistical switching kinetics of ferroelectrics. J Phys Condens Matter. 21(1):012207.
Love S. (2003) Neuronal expression of cell cycle-related proteins after brain ischaemia in man. Neurosci Lett. 353: 29-32.
Lu B, et al. (1996) Expression of synapsin I correlates with maturation of the neuromuscular synapse. Neuroscience. 74: 1087-1097.
Lu HR, et al. (2006) In-vitro experimental models for the risk assessment of antibiotic-induced QT prolongation. Eur J Pharmacol. 553: 229-239.
Ludwig T and A Thomson J. (2007) Defined, feeder-independent medium for human embryonic stem cell culture. Curr Protoc Stem Cell Biol. Chapter 1: Unit IC.2.
Lund AE and Narahashi T. (1982) Dose-dependent interaction of the pyrethroid isomers with sodium channels of squid axon membranes. Neurotoxicology. 3: 11-24.
Luo Y, et al. (2006) Effects of growth factors on extracellular matrix production by vocal fold fibroblasts in 3-dimensional culture. Tissue Eng. 12: 3365-3374.
Lyles JM, et al. (1992) Matrigel enhances myotube development in a serum-free defined medium. Intl Dev Neurosci. 10: 59-73.
Ma W, et al. (1998) Neuronal and glial epitopes and transmitter-synthesizing enzymes appear in parallel with membrane excitability during neuroblastoma x glioma hybrid differentiation. Brain Res Dev Brain Res. 106: 155-163.
Machida S, et al. (2004) Primary rat muscle progenitor cells have decreased proliferation and myotube formation during passages. Cell Prolif. 37: 267-277.
Maduell F. (2005) Hemodiafiltration. Hemodial Int. 9: 47-55.
Mahler GJ, et al. (2009a) Characterization of a gastrointestinal tract microscale cell culture analog used to predict drug toxicity. Biotechnol Bioeng. 104: 193-205.
Mahler GJ, et al. (2009b) Characterization of Caco-2 and HT29-MTX cocultures in an in vitro digestion/cell culture model used to predict iron bioavailability. J Nutr Biochem. 20: 494-50.
Malerba A, et al. (2009) Selection of multipotent cells and enhanced muscle reconstruction by myogenic macrophage-secreted factors. Exp Cell Res. 315:915-927.
Malm C, et al. (2004) Leukocytes, cytokines, growth factors and hormones in human skeletal muscle and blood after uphill or downhill running. J Physiol. 556:983-1000.
Malo N, et al. (2006) Statistical practice in high-throughput screening data analysis. Nat Biotechnol. 24: 167-175.
Marhl M, et al. (2000) Complex calcium oscillations and the role of mitochondria and cytosolic proteins. Biosystems. 57: 75-86.
Marona HRN, et al. (1999) Determination of sparfloxacin and its degradation products by HPLC-PDA. J Antimicrob Chemother. 44: 301-302.
Marques MJ and Neto HS. (1997) Ciliary neurotrophic factor stimulates in vivo myotube formation in mice. Neurosci Lett. 234: 43-46.
Mars T, et al. (2001) Differentiation of glial cells and motor neurons during the formation of neuromuscular junctions in cocultures of rat spinal cord explant and human muscle. J Comp Neurol. 438: 239-251.
Mars T, et al. (2003) Functional innervation of cultured human skeletal muscle proceeds by two modes with regard to agrin effects. Neuroscience. 118: 87-97.
Martin-Caraballo M and Greer JJ. (2000) Development of potassium conductances in perinatal rat phrenic motoneurons. J Neurophysiol. 83: 3497-3508.
Martinou JC, et al. (1992) Cholinergic differentiation factor (CDF/LIF) promotes survival of isolated rat embryonic motoneurons in vitro. Neuron. 8: 737-744.
Masu Y, et al. (1993) Disruption of the CNTF gene results in motor neuron degeneration. Nature. 365: 27-32.

(56) References Cited

OTHER PUBLICATIONS

Matsakas A and Patel K. (2009) Skeletal muscle fibre plasticity in response to selected environmental and physiological stimuli. Histol Histopathol. 24: 611-629.
Matsuda T, et al. (1992) Two-dimensional cell manipulation technology. An artificial neural circuit based on surface microphotoprocessing. Asaio J. 38:M243-M247.
Matthews PB. (1964) Muscle spindles and their motor control. Physiol Rev. 44:219-288.
Mattson MP, et al. (1992) Beta-Amyloid Peptides Destabilize Calcium Homeostasis and Render Human Cortical-Neurons Vulnerable to Excitotoxicity. J Neurosci. 12: 376-389.
Matzno S, et al. (2003) Evaluation of the synergistic adverse effects of concomitant therapy with statins and fibrates on rhabdomyolysis. J Pharm Pharmacol. 55: 795-802.
Maves L, et al. (2007) Pbx homeodomain proteins direct Myod activity to promote fast-muscle differentiation. Development. 134: 3371-3382.
Maynard EM. (2001) Visual prostheses. Annu Rev Biomed Eng. 3: 145-168.
Mcauliffe GJ, et al. (2008) Development of a gastrointestinal tract microscale cell culture analog to predict drug transport. Mol Cell Biomech. 5: 119-132.
McBeath R, et al. (2004) Cell shape, cytoskeletal tension, and RhoA regulate stem cell lineage commitment. Dev Cell. 6: 483-495.
McDevitt TC, et al. (2002) In vitro generation of differentiated cardiac myofibers on micropatterned laminin surfaces. J Biomed Mater Res. 60: 472-479.
McMahon JA, et al. (1998) Noggin-mediated antagonism of BMP signaling is required for growth and patterning of the neural tube and somite. Genes Dev. 12:1438-1452.
Megeney LA, et al. (1996) bFGF and LIF signaling activates STAT3 in proliferating myoblasts. Dev Genet. 19: 139-145.
Mehra S, et al. (2004) A boolean algorithm for reconstructing the structure of regulatory networks. Metab Eng. 6: 326-339.
Meijer L and Raymond E. (2003) Roscovitine and other purines as kinase inhibitors. From starfish oocytes to clinical trials. Ace Chem Res. 36: 417-425.
Melendez-Vasquez CV, et al. (2001) Nodes of Ranvier form in association with ezrin-radixin-moesin (ERM)-positive Schwann cell processes. Proc Natl Acad Sci US A. 98: 1235-1240.
Mendelsohn JD, et al. (2003) Rational design of cytophilic and cytophobic polyelectrolyte multilayer thin films. Biomacromolecules. 2003 4: 96-106.
Menendez L, et al. (2011) Wnt signaling and a Smad pathway blockade direct the differentiation of human pluripotent stem cells to multipotent neural crest cells. Proc Natl Acad Sci US A. 108: 19240-19245.
Menn B, et al. (2010) Delayed treatment with systemic (S)-roscovitine provides neuroprotection and inhibits in vivo CDK5 activity increase in animal stroke models. PLoS One. 5: e1211.
Metzger SW, et al. (1999) Development and characterization of surface chemistries for microfabricated biosensors. J of Vacuum Sci & Tech a-Vacuum Surfaces and Films. 17: 2623-2628.
Meyer G and Nabil MA. (1988) Novel optical approach to atomic force microscopy. Applied Physics Letters. 53: 1045-1047.
Meyer T, et al. (2004a) Micro-electrode arrays in cardiac safety pharmacology—A novel tool to study QT interval prolongation. Drug Saf. 27: 763-772.
Meyer T, et al. (2004b) QT-screen: high-throughput cardiac safety pharmacology by extracellular electrophysiology on primary cardiac myocytes. Assay Drug Dev Technol. 2: 507-514.
Miles GB, et al. (2004) Functional properties of motoneurons derived from mouse embryonic stem cells. J Neurosci. 24: 7848-7858.
Miller FD. (2007) Riding the waves: neural and nonneural ongms for mesenchymal stem cells. Cell Stem Cell. 1: 129-130.
Miller SC, et al. (1988) Tumor necrosis factor inhibits human myogenesis in vitro. Mol Cell Biol. 8: 2295-2301.
Mitsumoto H, et al. (2001) Effects of cardiotrophin-1 (CT-1) in a mouse motor neuron disease. Muscle Nerve. 24: 769-777.
Mizuseki K, et al. (2003) Generation of neural crest-derived peripheral neurons and floor plate cells from mouse and primate embryonic stem cells. Proc Natl Acad Sci US A. 100: 5828-5833.
Moe GK. (1962) On the multiple wavelet hypothesis of atrial fibrillation. Arch Int Pharmacodyn Ther. 183-188.
Mohammed JS, et al. (2004) Micropatterning of nanoengineered surfaces to study neuronal cell attachment in vitro. Biomacromolecules. 5: 1745-1755.
Mohan DK, et al. (2006) Toxin detection based on action potential shape analysis using a realistic mathematical model of differentiated NG 108-15 cells. Biosens Bioelectron. 21: 1804-1811.
Mokry J, et al. (2007) Differentiation of neural stem cells into cells of oligodendroglial lineage. Acta Medica (Hradec Kralove). 50: 35-41.
Molnar P, et al. (2007) Photolithographic Patterning of C2C12 Myotubes using Vitronectin as Growth Substrate in Serum-Free Medium. Biotechnol Prog. 23:265-268.
Molnar P, et al. (2007b) Synaptic connectivity in engineered neuronal networks. Methods Mol Biol. 403: 165-173.
Molnar P, et al. (2007c) Modeling of action potential generation in NG 108-15 cells. Methods Mol Biol. 403: 175-184.
Monaco EA 3rd and Vallano ML. (2005) Roscovitine triggers excitotoxicity in cultured granule neurons by enhancing glutamate release. Mol Pharmacol. 68:1331-1342.
Monaco EA 3rd. (2004) Recent evidence regarding a role for Cdk5 dysregulation in Alzheimer's disease. Curr Alzheimer Res. 1: 33-38.
Monyer H, et al. (1994) Developmental and regional expression in the rat brain and functional properties of four NMDA receptors. Neuron. 12: 529-540.
Moore JW, et al. (1991) The mRNAs encoding acidic FGF, basic FGF and FGF receptor are coordinately downregulated during myogemc differentiation. Development. 111: 741-748.
Morefield SI, et al. (2000) Drug evaluations using neuronal networks cultured on microelectrode arrays. Biosens Bioelectron. 15: 383-396.
Morimoto, S., & Masuda, M. (1984). Dependence of conduction velocity on spike interval during voluntary muscular contraction in human motor units. European journal of applied physiology and occupational physiology, 53(3), 191-195.
Morin F, et al. (2006) Constraining the connectivity of neuronal networks cultured on microelectrode arrays with microfluidic techniques: a step towards neuron-based functional chips. Biosens Bioelectron. 21: 1093-1100.
Morrow NG, et al. (1990) Increased expression of fibroblast growth factors in a rabbit skeletal muscle model of exercise conditioning. J Clin Invest. 85: 1816-1820.
Motamed K, et al. (2003) Fibroblast growth factor receptor-I mediates the inhibition of endothelial cell proliferation and the promotion of skeletal myoblast differentiation by SPARC: a role for protein kinase A. J Cell Biochem. 90: 408-423.
Moulard G, et al. (1998) Improvement of the cantilever beam technique for stress measurement during the physical vapor deposition process. J Vac Science Technol A. 16(2): 736-742.
Mousavi K, et al. (2004) BDNF rescues myosin heavy chain IIB muscle fibers after neonatal nerve injury. Am J Physiol Cell Physiol. 287: C22-C29.
Mrksich M. (2000) A surface chemistry approach to studying cell adhesion. Biosensors & Bioelectronics. 29: 267-273.
Mufti NA and Shuler ML. (1998) Different In Vitro Systems Affect CYPIAI Activity in Response to 2,3,7,8-Tetrachlorodibenzo-p-dioxin. Toxicol In Vitro. 12: 259-272.
Mulkey D, et al. (2003) Hyperbaric oxygen and chemical oxidants stimulate $CO_2/H+$-sensitive neurons in rat brain stem slices. J Appl Physiol. 95: 910-92.
Mullen RJ, et al. (1992) NeuN, a neuronal specific nuclear protein in vertebrates. Development. 116: 201-211.
Muller FJ, et al. (2006) Gene therapy: can neural stem cells deliver? Nat Rev Neurosci. 7: 75-84.
Muller P and Saul A. (2004) Elastic effects on surface physics. Surface Science Reports. 54: 157-258.

(56) References Cited

OTHER PUBLICATIONS

Muller T, et al. (1999) A 3-D microelectrode system for handling and caging single cells and particles. Biosens Bioelectron. 14: 247-256.
Munaron L. (2002) Calcium signalling and control of cell proliferation by tyrosine kinase receptors (review). Int J Mol Med. 10: 671-676.
Munsterberg AE, et al. (1995) Combinatorial signaling by Sonic hedgehog and Wnt family members induces myogenic bHLH gene expression in the somite. Genes Dev. 9: 2911-2922.
Muraki K, et al. (1994) Effects of noradrenaline on membrane currents and action potential shape in smooth muscle cells from guinea-pig ureter. J Physiol. 481:617-627.
Murgia M, et al. (2000) Ras is involved in nerve-activity-dependent regulation of muscle genes. Nat Cell Biol. 2: 142-147.
Murphy M, et al. (1994) FGF2 regulates proliferation of neural crest cells, with subsequent neuronal differentiation regulated by LIF or related factors. Development. 120: 3519-3528.
Mutyala MSK, et al. (2009) Mechanical and electronic approaches to improve the sensitivity of microcantilever sensors. Acta Mechanica Sinica. 25: 1-12.
Nagy Z, et al. (1997) Cell cycle markers in the hippocampus in Alzheimer's disease. Acta Neuropathol. 94: 6-15.
Nakamura S, et al. (2010) Analysis of cardiac toxicity caused by cyclophosphamide in the H9c2 cell line and isolated and perfused rat hearts. Gan to Kagaku Ryoho. 37: 677-680. Abstract only in English.
Nakamura Y, et al. (2007) The in vitro metabolism of a pyrethroid insecticide, permethrin, and its hydrolysis products in rats. Toxicology. 235: 176-184.
Nam Y, et al. (2006) Neural recording and stimulation of dissociated hippocampal cultures using microfabricated three-dimensional tip electrode array. J Neurosci Methods. 155: 296-299.
Nash MP, et al. (2006) Evidence for multiple mechanisms in human ventricular fibrillation. Circulation. 114: 536-542.
Nash, M. P., & Panfilov, A. V. (2004). Electromechanical model of excitable tissue to study reentrant cardiac arrhythmias. Progress in biophysics and molecular biology, 85(2), 501-522.
Nat R. (2011) Cortical network from human embryonic stem cells. J Cell Mol Med. 15: 1429-1431.
Natarajan A, et al. (2006) Microelectrode array recordings of cardiac action potentials as a high throughput method to evaluate pesticide toxicity. Toxicol In Vitro. 20: 375-381.
Natarajan A, et al. (2008) Growth and electrophysiological properties of rat embryonic cardiomyocytes on hydroxyl- and carboxyl-modified surfaces. J Biomater Sci Polym Ed. 19: 1319-1331.
Natarajan A, et al. (2011) Patterned cardiomyocytes on microelectrode arrays as a functional, high information content drug screening platform. Biomaterials. 32:4267-4274.
Natarajan A, et al. (2013) Engineered In Vitro Feed-Forward Networks. J Biotechnol Biomater. 3:153.
Natarajan AR, et al. (2004) Intrinsic cardiac catecholamines help maintain beating activity in neonatal rat cardiomyocyte cultures. Pediatr Res. 56: 411-417.
Nazaret C, et al. (2009) Mitochondrial energetic metabolism: a simplified model of TCA cycle with ATP production. J Theor Biol. 258: 455-464.
Nelson CE, et al. (1996) Analysis of Hox gene expression in the chick limb bud. Development. 122: 1449-1466.
Nelson CM and Bisell MJ. (2006) Of extracellular matrix, scaffolds, and signaling: tissue architecture regulates development, homeostasis, and cancer. Annu Rev Cell Dev Biol. 22: 287-309.
Nelson PG, et al. (1993) Synapse elimination from the mouse neuromuscular junction in vitro: a non-Hebbian activity-dependent process. J Neurobiol. 24:1517-1530.
Nelson PG. (1975) Nerve and muscle cells in culture. Physiol Rev. 55: 1-61.
Nerbonne JM and Kass RS. (2005) Molecular physiology of cardiac repolarization. Physiol Rev. 85: 1205-1253.

Nguemo F, et al. (2012) In vitro model for assessing arrhythmogenic properties of drugs based on high-resolution impedance measurements. Cell Physiol Biochem. 29: 819-832.
Nguyen L, et al. (2006) The Yin and Yang of cell cycle progression and differentiation in the oligodendroglial lineage. Ment Retard Dev Disabil Res Rev. 12: 85-96.
Nicolelis MAL and Ribeiro S. (2002) Multielectrode recordings: the next steps. Curr Opin Neurobiol. 12: 602-606.
Nimmrich V, et al. (2008) Amyloid beta oligomers (A beta(I-42) globulomer) suppress spontaneous synaptic activity by inhibition of P/Q-type calcium currents. J Neurosci. 28: 788-797.
Nishikawa J, et al. (2005) Increase of Cardiotrophin-1 immunoreactivity in regenerating and overloaded but not denervated muscles of rats. Neuropathology. 25: 54-65.
Nishimaru H, et al. (2005) Mammalian motor neurons corelease glutamate and acetylcholine at central synapses. Proc Natl Acad Sci US A. 102: 5245-5249.
Nistor GI, et al. (2005) Human embryonic stem cells differentiate into oligodendrocytes in high purity and myelinate after spinal cord transplantation. Glia. 49: 385-396.
Noble D. (2004) Modeling the heart. Physiology (Bethesda). 19: 191-197.
Noll E and Miller RH. (1993) Oligodendrocyte precursors originate at the ventral ventricular zone dorsal to the ventral midline region in the embryonic rat spinal cord. Development. 118: 563-573.
Normann RA, et al. (1999) A neural interface for a cortical vision prosthesis. Vision Res. 39: 2577-2587.
Norris W, et al. (2000) Slow muscle induction by Hedgehog signalling in vitro. J Cell Sci. 113: 2695-2703.
Nugaeva, N, et al. (2005). Micromechanical cantilever array sensors for selective fungal immobilization and fast growth detection. Biosensors and Bioelectronics, 21(6), 849-856.
Nyitrai G, et al. (2006) Extracellular level of GABA and Glu: III VIVO microdialysis-HPLC measurements. Curr Top Med Chem. 6: 935-940.
Oakley RA, et al. (1997) Neurotrophin-3 promotes the differentiation of muscle spindle afferents in the absence of peripheral targets. J Neurosci. 17: 4262-4274.
O'Connor SM, et al. (2000) Immobilization of neural cells in three-dimensional matrices for biosensor applications. Biosens Bioelectron. 14: 871-881.
Offenhausser A and Knoll W. (2001) Cell-transistor hybrid systems and their potential applications. Trends Biotechnol. 19: 62-66.
Offenhausser A, et al. (1997) Field-effect transistor array for monitoring electrical activity from mammalian neurons in culture. Biosensors and Bioelectronics. 12: 819-826.
Oh TI, et al. (2007) Real-time fluorescence detection of multiple microscale cell culture analog devices in situ. Cytometry A. 71: 857-865.
Oliver L, et al. (1992) Acidic fibroblast growth factor (aFGF) in developing normal and dystrophic (mdx) mouse muscles. Distribution in degenerating and regenerating mdx myofibres. Growth Factors. 7: 97-106.
Olson E. (1992a) Activation of muscle-specific transcription by myogenic helixloop-helix proteins. Symp Soc Exp Biol. 46: 331-341.
Olson EN and Perry WM. (1992b) MyoD and the paradoxes of myogenesis. Curr Biol. 2: 35-37.
Olson EN and Williams RS. (2000) Calcineurin Signaling and Muscle Remodeling. Cell. 101: 689-692.
Olson EN. (1992c) Interplay between proliferation and differentiation within the myogenic lineage. Dev Biol. 154: 261-272.
Olwin BB and Rapraeger A. (1992) Repression of myogenic differentiation by aFGF, bFGF, and K-FGF is dependent on cellular heparan sulfate. J Cell Biol. 118: 631-639.
Oppenheim RW, et al. (1991) Control of embryonic motoneuron survival in vivo by ciliary neurotrophic factor. Science. 251: 1616-1618.
Oppenheim RW, et al. (2001) Cardiotrophin-1, a muscle-derived cytokine, is required for the survival of subpopulations of developing motoneurons. J Neurosci. 21: 1283-1291.
Orentas DM and Miller RH. (1999) Regulation of oligodendrocyte development. Mol Neurobiol. 18: 247-259.

(56) References Cited

OTHER PUBLICATIONS

Orlov SN and Hamet P. (2006) Intracellular monovalent ions as second messengers. J Membr Biol. 210: 161-172.
Ostuni E, et al. (2000) Patterning mammalian cells using elastomeric membranes. Langmuir. 16: 7811-7819.
Oumata N, et al. (2008) Roscovitine-derived, dual-specificity inhibitors of cyclindependent kinases and casein kinases 1. J Med Chem. 51: 5229-5242.
Padmanabhan J, et al. (1999) Role of cell cycle regulatory proteins in cerebellar granule neuron apoptosis. J Neurosci. 19: 8747-8756.
Pagan SM, et al. (1996) Surgical removal of limb bud Sonic hedgehog results in posterior skeletal defects. Dev Biol. 180: 35-40.
Pancrazio JJ, et al. (1998) Portable cell-based biosensor system for toxin detection. Sensors and Actuators B Chem. 53: 179-185.
Park J, et al. (2005) Real-time measurement of the contractile forces of self-organized cardiomyocytes on hybrid biopolymer microcantilevers. Anal Chem. 77: 6571-6580.
Park, TH et al. (2003) Integration of Cell Culture and Microfabrication Technology. Biotechnol. Prog. 19: 243-253.
Parker KK, et al. (2008) Myofibrillar architecture m engineered cardiac myocytes. Circ Res. 103: 340-342.
Parng C, et al. (2002) Zebrafish: A Preclinical Model for Drug Screening. Assay Drug Dev Technol. 1: 41-48.
Parviz M and Gross GW. (2007) Quantification of zinc toxicity using neuronal networks on microelectrode arrays. Neurotoxicolo12:v. 28: 520-531.
Paspalas CD and Papadopoulos GC. (1996) Ultrastructural relationships between noradrenergic nerve fibers and non-neuronal elements in the rat cerebral cortex. Glia. 17: 133-146.
Payne ET, et al. (2006) Nutritional therapy improves function and complements corticosteroid intervention in mdx mice. Muscle Nerve. 33: 66-77.
Peng HB, et al. (2003) Differential effects of neurotrophins and schwann cell-derived signals on neuronal survival/growth and synaptogenesis. J Neurosci. 23:5050-5060.
Peroulakis ME and Forger NG. (2000) Ciliary neurotrophic factor increases muscle fiber number in the developing levator ani muscle of female rats. Neurosci Lett. 296: 73-76.
Perrier AL, et al. (2004) Derivation of midbrain dopamine neurons from human embryonic stem cells. Proc Natl Acad Sci USA. 101: 12543-12548.
Peters A. (1964) Observations on the Connexions Between A709. Myelin Sheaths and Glial Cells in the Optic Nerves of Young Rats. J Anat. 98: 125-134.
Peterson CA, et al. (1999) Effects of moisture on Fowler-Nordheim characterization of thin silicon-oxide films. J Vac Science Technol A. 17: 2753-2758.
Pette D and Staron S. (2001) Transitions of muscle fiber phenotypic profiles. Histochem and Cell Biol. 115: 359-372.
Pette D, et al. (2002) Partial fast-to-slow conversion of regenerating rat fast-twithc muscle by chronic low frequency stimulation. J Muscle Res Cell Motil. 3:215-221.
Pfeiffer SE, et al. (1993) The oligodendrocyte and its many cellular processes. Trends Cell Biol. 3: 191-197.
Pfrieger FW and Barres BA. (1997) Synaptic efficacy enhanced by glial cells in vitro. Science. 277: 1684-1687.
Pijnappels DA, et al. (2007) Resynchronization of separated rat cardiomyocyte fields with genetically modified human ventricular scar fibroblasts. Circulation. 116: 2018-2028.
Pillekamp F, et al. (2012) Contractile properties of early human embryonic stem cell-derived cardiomyocytes: beta-adrenergic stimulation induces positive chronotropy and lusitropy but not inotronv. Stem Cells Dev. 21: 2111-2121.
Podratz J, et al. (2004) Antioxidants are necessary for myelination of dorsal root ganglion neurons, in vitro. Glia. 45: 54-58.
Pomp O, et al. (2005) Generation of peripheral sensory and sympathetic neurons and neural crest cells from human embryonic stem cells. Stem Cells. 23: 923-930.

Pomp O, et al. (2008) PA6-induced human embryonic stem cell-derived neurospheres: a new source of human peripheral sensory neurons and neural crest cells. Brain Res. 1230: 50-60.
Pontier C, et al. (2001) HT29-MTX and Caco-2/TC7 monolayers as predictive models for human intestinal absorption: role of the mucus layer. J Pharm Sci. 90:1608-1619.
Popat KC, et al. (2004) Surface modification of nanoporous alumina surfaces with poly(ethylene glycol). Langmuir. 20: 8035-8041.
Popat KC, et al. (2004b) Quantitative xps analysis of peg-modified silicon surfaces. J Phys Chem. 108: 5185-5188.
Porto F, et al. (2008) Towards a Scientific Model Management System. ER Workshops 2008. NCS 5232: 55-65.
Pouton CW and Haynes JM. (2005) Pharmaceutical applications of embryonic stem cells. Adv Drug Deliv Rev. 57: 1918-1934.
Powell C, et al. (1999) Tissue engineered human bioartificial muscles expressing a foreign recombinant protein for gene therapy. Hum Gene Ther. 10: 565-577.
Powell C, et al. (2002) Mechanical stimulation improves tissue-engineered human skeletal muscle. Am J Physiol Cell Physiol. 283: C1557-C1565.
Price PJ and Brewer GJ. (2001) Serum-Free Media for Neural Cell Cultures. Protocols for Neural Cell Cultures, 3rd Ed, Humana Press Inc., Totowa, NJ, Chapter 19, 255-264.
Pringle NP, et al. (1996) Determination of neuroepithelial cell fate: induction of the oligodendrocyte lineage by ventral midline cells and sonic hedgehog. Dev Biol. 177: 30-42.
Quinn LS, et al. (1990) Paracrine control of myoblast proliferation and differentiation by fibroblasts. Dev Biol. 140: 8-19.
Raible DW and McMorris FA. (1989) Cyclic AMP regulates the rate of differentiation of oligodendrocytes without changing the lineage commitment of their progenitors. Dev Biol. 133: 437-446.
Raible DW and Mc Morris FA. (1990) Induction of oligodendrocyte differentiation by activators of adenylate cyclase. J Neurosci Res. 27: 43-46.
Raiteri R, et al. (2001) Micromechanical cantilever-based biosensors. Sensors and Actuators B-Chemical. 79: 115-126.
Rajnicek AM, et al. (1997) Contact guidance of CNS neurites on grooved quartz: influence of groove dimensions, neuronal age and cell type. J Cell Sci. 110: 2905-2913.
Raley-Susman KM, et al. (1991) Regulation of intracellular pH in cultured hippocampal neurons by an amiloride-insensitive Na+/H+ exchanger. J Biol Chem. 266: 2739-2745.
Rampe D, et al. (1997) A mechanism for the proarrhythmic effects of cisapride (Propulsid): high affinity blockade of the human cardiac potassium channel Herg. Febs Lett. 417: 28-32.
Ravenscroft MS, et al. (1998) Developmental Neurobiology Implications from Fabrication and Analysis of Hippocampal Neuronal Networks on Patterned Silane-Modified Surfaces. J Am Chem Soc. 120: 12169-12177.
Ravenscroft-Chang MS, et al. (2010) Altered calcium dynamics in cardiac cells grown on silane-modified surfaces. Biomaterials. 31: 602-607.
Recanatini M, et al. (2005) QT prolongation through hERG K(+) channel blockade: current knowledge and strategies for the early prediction during drug development. Med Res Rev. 25: 133-166.
Rekling JC, et al. (2000) Synaptic control of motoneuronal excitability. Physiol Rev. 80: 767-852.
Reppel M, et al. (2004) Beta-adrenergic and muscarinic modulation of human embryonic stem cell-derived cardiomyocytes. Cell Physiol Biochem. 14: 187-196.
Reppel M, et al. (2005) The electrocardiogram of human embryonic stem cell-derived cardiomyocytes. J Electrocardiol. 38: 166-170.
Reppel M, et al. (2007) Effect of cardioactive drugs on action potential generation and propagation in embryonic stem cell-derived cardiomyocytes. Cell Physiol Biochem. 19: 213-224.
Revzin A, et al. (2003) Surface Engineering with Poly( ethylene glycol) Photolithography to Create High-Density Cell Arrays on Glass. Langmuir. 19:9855-9862.
Reyes D, et al. (2004) Micropatterning neuronal cells on polyelectrolyte multilayers. Langmuir. 20: 8805-8811.
Richards S, et al. (2008) Development of defined media for the serum-free expansion of primary keratinocytes and human embryonic stem cells. Tissue Eng Part C Methods. 14: 221-232.

(56) References Cited

OTHER PUBLICATIONS

Richert L, et al. (2004) pH dependent growth of poly(L-lysine )/poly(L-glutamic) acid multilayer films and their cell adhesion properties. Surface Science. 570: 13-29.
Riley M. (1993) Functions of the gene products of *Escherichia coli*. Microbiol Rev. 57: 862-952.
Robertson TA, et al. (2000) Comparison of astrocytic and myocytic metabolic dysregulation m apolipoprotein E deficient and human apolipoprotein E transgenic mice. Neuroscience. 98: 353-359.
Rodan SB, et al. (1989) Effects of acidic and basic fibroblast growth factors on osteoblastic cells. Connect Tissue Res. 20: 283-288.
Roden DM, et al. (2002) Cardiac ion channels. Annu Rev Physiol. 64: 431-475.
Rogister B, et al. (1999) From neural stem cells to myelinating oligodendrocytes. Mol Cell Neurosci. 14: 287-300.
Rohr S, et al. (1991) Patterned growth of neonatal rat heart cells in culture. Morphological and electrophysiological characterization. Circ Res. 68: 114-130.
Rosati B and McKinnon D. (2004) Regulation of ion channel expression. Circ Res. 94: 874-883.
Rosenberg SS, et al. (2008) The geometric and spatial constraints of the microenvironment induce oligodendrocyte differentiation. Proc Natl Acad Sci USA. 105: 14662-14667.
Rumsey JW, et al. (2008) Tissue Engineering Intrafusal Fibers: Dose and Time Dependent Differentiation of Nuclear Bag Fibers in a Defined In Vitro System using Neuregulin 1-beta-I. Biomaterials. 29: 994-1004.
Rumsey JW, et al. (2009) Node of Ranvier formation on motoneurons in vitro. Biomaterials. 30: 3567-3572.
Rumsey JW, et al. (2010) Tissue engineering the mechanosensory circuit of the stretch reflex arc: sensory neuron innervation of intrafusal muscle fibers. Biomaterials. 31: 8218-8227.
Rutten WLC. (2002) Selective electrical interfaces with the nervous system. Annu Rev Biomed Eng. 4: 407-452.
Sakuma K, et al. (2000) Differential adaptation of growth and differentiation factor 8/myostatin, fibroblast growth factor 6 and leukemia inhibitory factor in overloaded, regenerating and denervated rat muscles. Biochim Biophys Acta. 1497: 77-88.
Sala M, et al. (2009) Electrophysiological changes of cardiac function during antidepressant treatment. Ther Adv Cardiovasc Dis. 3: 29-43.
Sander D, et al. (1995) A simple technique to measure stress in ultrathin films during growth. Rev Sci Instrum. 66: 4734.
Sanes JR and Lichtman JW. (1999) Development of the vertebrate neuromuscular junction. Annu Rev Neurosci. 22: 389-442.
Sanes JR and Lichtman JW. (2001) Induction, assembly, maturation and maintenance of a postsynaptic apparatus. Nat Rev Neurosci. 2: 791-805.
Sanes JR. ( 1997) Genetic analysis of postsynaptic differentiation at the vertebrate neuromuscular junction. Curr Opin Neurobiol. 7: 93-100.
Sasahara K, et al. (2007) Mode of action and functional significance of estrogen-inducing dendritic growth, spinogenesis, and synaptogenesis in the developing Purkinje cell. JNeurosci. 27: 7408-7417.
Sathaye A, et al. (2006) Electrical pacing counteracts intrinsic shortening of action potential duration of neonatal rat ventricular cells in culture. J Mol Cell Cardiol. 41: 633-64.
Scaal M, et al. (1999) SF/HGF is a mediator between limb patterning and muscle development. Development. 126: 4885-4893.
Schaffner AE, et al. (1995) Investigation of the factors necessary for growth of hippocampal neurons in a defined system. J Neurosci Methods. 62: 111-11.
Scherer J, et al. (1995) Differentiation and maturation of rabbit retinal oligodendrocyte precursor cells in vitro. Brain Res Dev Brain Res. 89: 214-226.
Schiaffino S and Serrano A. (2002) Calcineurin signaling and neural control of skeletal muscle fiber type and size. Trends Pharmacol Sci. 23: 569-575.
Schiaffino S, et al. (2007) Activity-Dependent Signaling Pathways Controlling Muscle Diversity and Plasticity. Physiology. 22: 269-278.
Schluter H and Kaur P. (2009) Bioengineered human skin from embryonic stem cells. Lancet. 374: 1725-1726.
Schneider A, et al. (2006) Glycated polyelectrolyte multilayer films: differential adhesion of primary versus tumor cells. Biomacromolecules. 7: 2882-2889.
Schneider AG, et al. (1999) Muscle LIM protein: expressed in slow muscle and indcued in fast muscle by enhanced contractile activity. Am J Physiol. 276:C900-C906.
Scholzen T and Gerdes J. (2000) The Ki-67 protein: from the known and the unknown. J Cell Physiol. 182: 311-322.
Schulz TC, et al. (2004) Differentiation of human embryonic stem cells to dopaminergic neurons in serum-free suspension culture. Stem Cells. 22: 1218-1238.
Schuster D, et al. (2005) Why drugs fail—a study on side effects in new chemical entities. Curr Pharm Des. 11: 3545-3559.
Schuster Rand Holzhutter HG. (1995) Use of mathematical models for predicting the metabolic effect of large-scale enzyme activity alterations. Application to enzyme deficiencies ofred blood cells. Eur J Biochem. 229: 403-418.
Schwab ME. (2002) Repairing the injured spinal cord. Science. 295: 1029-1031.
Schwarz JJ, et al. (1992) The basic region of myogenin cooperates with two transcription activation domains to induce muscle-specific transcription. Mol Cell Biol. 12: 266-275.
Scollon EJ, et al. (2009) In vitro metabolism of pyrethroid pesticides by rat and human hepatic microsomes and cytochrome p450 isoforms. Drug Metab Dispos. 37: 221-228.
Scoote Mand Williams AJ. (2004) Myocardial calcium signalling and arrhythmia pathogenesis. Biochem Biophys Res Commun. 322: 1286-1309.
Scott W, et al. (2001) Human Skeletal Muscle Fiber Type Classifications. Phys Ther. 81: 1810-1816.
Selivanov VA, et al. (2004) Nucleotide-gated KA TP channels integrated with creatine and adenylate kinases: amplification, tuning and sensing of energetic signals in the compartmentalized cellular environment. Mol Cell Biochem. 256-257: 243-256.
Selivanova OM, et al. (2003) Compact globular structure of Thermus thermophilus ribosomal protein S 1 in solution: sedimentation and calorimetric study. J Biol Chem. 278: 36311-36314.
Semsarian C, et al. (1999) Skeletal muscle hypertrophy is mediated by a Ca2+ dependent calcineurin signalling pathway. Nature. 400: 576-581.
Sghirlanzoni A, et al. (2005) Sensory neuron diseases. Lancet Neurol. 4: 349-361.
Shah NM, et al. (1996) Alternative neural crest cell fates are instructively promoted by TGFbeta superfamily members. Cell. 85: 331-343.
Shainberg A, et al. (1976) Induction of acetylcholine receptors in muscle cultures. Pflugers Arch. 361: 255-261.
Shankar GM, et al. (2008) Amyloid-beta protein dimers isolated directly from Alzheimer's brains impair synaptic plasticity and memory. Nat Med. 14:837-842.
Shansky J, et al. (1997) A simplified method for tissue engineering skeletal muscle organoids in vitro. In Vitro Cell Dev Biol Anim. 33: 659-661.
Shansky J, et al. (2006a) Paracrine release of insulin-like growth factor 1 from a bioengineered tissue stimulates skeletal muscle growth in vitro. Tissue Eng. 12:1833-1841.
Shansky J, et al. (2006b) Tissue engineering human skeletal muscle for clinical applications. Culture of Cells for Tissue Engineering. 239-257.
Sheikh SI and Amato AA. (2010) The dorsal root ganglion under attack: the acquired sensory ganglionopathies. Pract Neurol. 10: 326-334.
Sheng Z, et al. (1996) Cardiotrophin-1 displays early expression in the murine heart tube and promotes cardiac myocyte survival. Development. 122: 419-428.
Sheridan DC, et al. (2003a) Ca2+-dependent excitation-contraction coupling triggered by the heterologous cardiac/brain DHPR beta2a-subunit in skeletal myotubes. Biophys J. 85: 3739-3757.

(56) References Cited

OTHER PUBLICATIONS

Sheridan DC, et al. (2003b) Truncation of the carboxyl terminus of the dihydropyridine receptor betala subunit promotes Ca2+ dependent excitation-contraction coupling in skeletal myotubes. Biophys J. 84: 220-237.
Sherman DL and Brophy PJ. (2005a) Mechanisms of axon ensheathment and myelin growth. Nat Rev Neurosci. 6: 683-690.
Sherman DL, et al. (2005b) Neurofascins are required to establish axonal domains for saltatory conduction. Neuron. 48: 737-742.
Shimono K, et al. (2000) Multielectrode Recording of Rhythmic Oscillations in Brain Slices: A Novel Technique for Screening Psychoactive Drugs. Faseb J. 14:1047.
Shin S, et al. (2005) Human motor neuron differentiation from human embryonic stem cells. Stem Cells Dev. 14: 266-269.
Shuler ML. (2012) Modeling life. Ann Biomed Eng. 40: 1399-1407.
Silver JH, et al. (1999) Surface properties and hemocompatibility of alkyl-siloxane monolayers supported on silicone rubber: effect of alkyl chain length and ionic functionality. Biomaterials. 20: 1533-1543.
Simmons A, et al. (2005) Painful lessons. Nat Rev Drug Discov. 4: 800-803.
Simon M, et al. (2003) Effect of NT-4 and BDNF delivery to damaged sciatic nerves on phenotypic recovery of fast and slow muscles fibres. Eur J Neurosci. 18: 2460-2466.
Simpson ML, et al. (2001) Whole-cell biocomputing. Trends Biotechnol. 19:317-323.
Sin A, et al. (2004) The design and fabrication of three-chamber microscale cell culture analog devices with integrated dissolved oxygen sensors. Biotechnol Prog. 20: 338-345.
Singh RP, et al. (2009) Retentive multipotency of adult dorsal root ganglia stem cells. Cell Transplant. 18: 55-68.
Singhvi R, et al. (1994) Engineering cell shape and function. Science. 264: 696-698.
Slepchenko BM, et al. (2003) Quantitative cell biology with the Virtual Cell. Trends Cell Biol. 13: 570-576.
Smith J and Schofield PN. (1994) The effects of fibroblast growth factors in long-term primary culture of dystrophic (mdx) mouse muscle myoblasts. Exp Cell Res. 210: 86-93.
Smith JR, et al. (2008) Inhibition of Activin/Nodal signaling promotes specification of human embryonic stem cells into neuroectoderm. Dev Biol. 313:107-1.
Smith PF, et al. (1991) HMG-COA reductase inhibitor-induced myopathy in the rat: cyclosporine A interaction and mechanism studies. J Pharmacol Exp Ther. 257: 1225-1235.
Smolen PD, et al. (2004) Mathematical Modeling and Analysis of Intracellular Signaling Pathways. From Molecules to Networks—An Introduction to Cellular and Molecular Neuroscience. p. 391-430.
Sofia SJ and Merrill EW. (1997) Protein Adsorption on Poly(ethylene oxide)-Grafted Silicon Surfaces. ACS Symposium Series. 680: 342-360.
Song WK, et al. (1992) H36-alpha 7 is a novel integrin alpha chain that is developmentally regulated during skeletal myogenesis. J Cell Biol. 117: 643-657.
Soni AS, et al. (2008) Determination of critical network interactions: an augmented Boolean pseudo-dynamics approach. IET Syst Biol. 2: 55-63.
Soundarapandian MM, et al. (2007) Role of K(ATP) channels in protection against neuronal excitatory insults. J Neurochem. 103: 1721-172.
Soundararajan P, et al. (2007) Easy and rapid differentiation of embryonic stem cells into functional motoneurons using sonic hedgehog-producing cells. Stem Cells. 25: 1697-1706.
Spach MS and Heidlage JF. (1995) The stochastic nature of cardiac propagation at a microscopic level. Electrical description of myocardial architecture and its application to conduction. Circ Res. 76: 366-380.
Spach MS. (1983) The role of cell-to-cell coupling in cardiac conduction disturbances. Adv Exp Med Biol. 161: 61-77.

Spargo BJ, et al. (1994) Spatially controlled adhesion, spreading, and differentiation of endothelial cells on self-assembled molecular monolayers. Proc Natl Acad Sci USA. 91: 11070-11074.
Spencer CI, et al. (2001) Actions of pyrethroid insecticides on sodium currents, action potentials, and contractile rhythm in isolated mammalian ventricular myocytes and perfused hearts. J Pharmacol Exp Ther. 298: 1067-1082.
St John PM, et al. (1997) Preferential glial cell attachment to microcontact printed surfaces. J Neurosci Methods. 75: 171-177.
St. George-Hyslop PH and Petit A. (2004) Molecular biology and genetics of Alzheimer's disease.CR Biol. 328: 119-130.
Stavarachi M, et al. (2010) Spinal muscular atrophy disease: a literature review for therapeutic strategies. J Med Life. 3: 3-9.
Steffen LS, et al. (2007) Zebrafish orthologs of human muscular dystrophy genes. BMC Genomics. 8: 7.
Stenger DA, et al. (1992) Coplanar Molecular Assemblies of Aminoalkylsilane and Perfluorinated Alkylsilane -Characterization and Geometric Definition of Mammalian-Cell Adhesion and Growth. Journal of the American Chemical Society. 114: 8435-8442.
Stenger DA, et al. (1993) Surface determinants of neuronal survival and growth on self- assembled monolayers in culture. Brain Res. 630: 136-147.
Stenger DA, et al. (1998) Microlithographic determination of axonal/dendritic polarity in cultured hippocampal neurons. J Neurosci Methods. 82: 167-173.
Sternberger NH, et al. (1985) Immunocytochemistry of myelin basic proteins in adult rat oligodendroglia. J Neuroimmunol. 7: 355-363.
Stett A, et al. (2003) Biological application of microelectrode arrays in drug discovery and basic research. Anal Bioanal Chem. 377: 486-495.
Stevens JL. (2006) Future of toxicology—mechanisms of toxicity and drug safety: where do we go from here? Chem Res Toxicol. 19: 1393-1401.
Stinstra J, et al. (2006) A Model of 3D Propagation in Discrete Cardiac Tissue. Comput Cardiol. 33: 41-44.
Stockwell BR. (2004) Exploring biology with small organic molecules. Nature. 432: 846-854.
Stoney GG. (1909) The Tension of Metallic Films Deposited by Electrolysis. Proc Roy Soc London. 82: 172-175.
Subramanian B, et al. (2010) Tissue-engineered three-dimensional in vitro models for normal and diseased kidney. Tissue Eng Part A. 16: 2821-2831.
Sun L, et al. (2007) JAK1-STAT1-STAT3, a key pathway promoting proliferation and preventing premature differentiation of myoblasts. J Cell Biol. 179: 129-138.
Sung JH and Shuler ML. (2009a) A micro cell culture analog (microCCA) with 3-D hydrogel culture of multiple cell lines to assess metabolism-dependent cytotoxicity of anti-cancer drugs. Lab Chip. 9: 1385-1394.
Sung JH and Shuler ML. (2009b) Prevention of air bubble formation in a microfluidic perfusion cell culture system using a microscale bubble trap. Biomed Microdevices. 11: 731-738.
Sung JH, et al. (2009c) Fluorescence optical detection in situ for real-time monitoring of cytochrome P450 enzymatic activity of liver cells in multiple microfluidic devices. Biotechnol Bioeng. 104: 516-525.
Sung JH, et al. (2010) A microfluidic device for a pharmacokinetic-pharmacodynamic (PK-PD) model on a chip. Lab Chip. 10: 446-455.
Sung JH, et al. (2013) Microfabricated mammalian organ systems and their integration into models of whole animals and humans. Lab Chip. 13: 1201-1212.
Suter W. (2006) Predictive value of in vitro safety studies. Curr Opin Chem Biol. 10: 362-366.
Sutton NM, et al. (2007) Clinical effects and outcome of feline permethrin spot-on poisonings reported to the Veterinary Poisons Information Service (VPIS), London. J Feline Med Surg. 9: 335-339.
Swasdison Sand Mayne R. (1992) Formation of highly organized skeletal muscle fibers in vitro. Comparison with muscle development in vivo. J Cell Sci. 102:643-652.

(56) References Cited

OTHER PUBLICATIONS

Swynghedauw B. (1999) Molecular mechanisms of myocardial remodeling. Physiol Rev. 79: 215-262.
Takagishi Y, et al. (2000) Species-specific difference in distribution of voltage-gated L-type Ca(2+) channels of cardiac myocytes. Am J Physiol Cell Physiol. 279: C1963-C1969.
Takahashi T. (1978) Intracellular recording from visually identified motoneurons in rat spinal cord slices. Proc R Soc Lond B Biol Sci. 202: 417-421.
Takashima Y, et al. (2007) Neuroepithelial cells supply an initial transient wave of MSC differentiation. Cell. 129: 1377-1388.
Tan W and Desai TA. (2003) Microfluidic patterning of cells in extracellular matrix biopolymers: effects of channel size, cell type, and matrix composition on pattern integrity. Tissue Eng. 9: 255-267.
Tanaka M, et al. (2005) An Unbiased Cell Morphology Based Screen for New, Biologically Active Small Molecules. PLoS Biol. 3: e128.
Tanaka Y, et al. (2006) An actuated pump on-chip powered by cultured cardiomyocytes. Lab Chip. 6: 362-368.
Tarasenko YI, et al. (2007) Human fetal neural stem cells grafted into contusion-injured rat spinal cords improve behavior. JN eurosci Res. 85: 4 7-57.
Tatosian DA and Shuler ML. (2009) A novel system for evaluation of drug mixtures for potential efficacy in treating multidrug resistant cancers. Biotechnol Bioeng. 103: 187-198.
Termin A and Pette D. (1992) Changes in myosin heavy-chain isoform synthesis of chronically stimulated rat fast-twitch muscle. Eur J Biochem. 204: 569-573.
Terstappen GC, et al. (2007) Target deconvolution strategies in drug discovery. Nat. Rev Drug Discov. 6: 891-9.
Thomas CA, et al. (1972) A miniature microelectrode array to monitor the bioelectric activity of cultured cells. Exp Cell Res. 74: 61-66.
Thomas R. (1973) Boolean formalization of genetic control circuits. J Theor Biol. 1973. 42: 563-585.
Thompson PD, et al. (2006) An assessment of statin safety by muscle experts. Am J Cardiol. 97: 69C-76C.
Thompson RB, et al. (2005) Intracardiac transplantation of a mixed population of bone marrow cells improves both regional systolic contractility and diastolic relaxation. J Heart Lung Transplant. 24: 205-214.
Thorrez L, et al. (2008) Growth, differentiation, transplantation and survival of human skeletal myofibers on biodegradable scaffolds. Biomaterials. 29: 75-84.
Timmerman W and Westerink BH. (1997) Brain microdialysis of GABA and glutamate: what does it signify? Synapse. 27: 242-261.
Tobert JA. (2003) Lovastatin and beyond: the history of the HMGCoA reductase inhibitors. Nat Rev Drug Discov. 2: 517-526.
Toga T, et al. (2007) The 5-HT( 4) agonists cisapride, mosapride, and CJ-033466, a Novel potent compound, exhibit different human ether-a-go-go-related gene (hERG)-blocking activities. J Pharmacol Sci. 105: 207-210.
Tomb JF, et al. (1997) The complete genome sequence of the gastric pathogen Helicobacter pylori. Nature. 388: 539-547.
Torgan CE and Daniels MP. (2001) Regulation of myosin heavy chain expression during rat skeletal muscle development in vitro. Mol Biol Cell. 12: 1499-1508.
Torgan CE and Daniels MP. (2006) Calcineurin localization in skeletal muscle offers insights into potential new targets. J Histochem Cytochem. 54: 119-128.
Torimitsu Kand Kawana A. (1990) Selective growth of sensory nerve fibers on metal oxide pattern in culture. Brain Res Dev Brain Res. 51: 128-131.
Townsend KP and Pratico D. (2005) Novel therapeutic opportunities for Alzheimer's disease: focus on nonsteroidal anti-inflammatory drugs. FASEB J.
Tung L and Cysyk J. (2007) Imaging fibrillation/defibrillation in a dish. J Electrocardiol. 40: S62-S65.
Tung L and Zhang YB. (2006) Optical imaging of arrhythmias in tissue culture. J Electrocardiol. 39: S2-S6.

Uhm CS, et al. (2001) Synapse-forming axons and recombinant agrin induce microprocess formation on myotubes. J Neurosci. 21: 9678-9689.
Ullian EM, et al. (2004) Schwann cells and astrocytes induce synapse formation by spinal motor neurons in culture. Mol Cell Neurosci. 25: 241-251.
Umbach JA, et al. (2012) Functional neuromuscular junctions formed by embryonic stem cell-derived motor neurons. PLoS One. 7: e36049.
Urakami H and Chiu A Y. (1990) A monoclonal antibody that recognizes somatic motor neurons in the mature rat nervous system. J Neurosci. 10: 620-630.
Urazaev AK, et al. (1995) Muscle NMDA receptors regulate the resting membrane potential through No. synthase. Physiol Res. 44: 205-208.
Vakakis N, et al. (1995) In vitro myoblast to myotube transformations in the presence ofleukemia inhibitory factor. Neurochem Int. 27: 329-335.
Valentin JP, et al. (2004) Review of the predictive value of the Langendorff heart model (Screenit system) in assessing the proarrhythmic potential of drugs. J Pharmacol Toxicol Methods. 49: 171-181.
Van de Ven C, et al. (2007) The potential of umbilical cord blood multipotent stem cells for nonhematopoietic tissue and cell regeneration. Exp Hematol. 35:1753-1765.
Van der Valk J, et al. (2010) Optimization of chemically defined cell culture media—replacing fetal bovine serum in mammalian in vitro methods. Toxicol In Vitro. 24: 1053-1063.
Van Rijen HV, et al. (2006) Connexins and cardiac arrhythmias. Adv Cardiol. 42:150-160.
Van Soest PF and Kits KS. (1998) Conopressin affects excitability, firing, and action potential shape through stimulation of transient and persistent inward currents in mulluscan neurons. J Neurophysiol. 79: 1619-1632.
Vandenburgh HH, et al. (1991) Computer aided mechanogenesis of skeletal muscle organs from single cells in vitro. FASEB J. 5: 2860-2867.
Vandenburgh HH, et al. (1996) Tissue engineered skeletal muscle organoids for reversible gene therapy. Hum Gene Ther. 7: 2195-2200.
Vandenburgh HH, et al. (2008) A drug screening platform based on the contractility of tissue engineered muscle. Muscle Nerve. 37: 438-447.
Vandenburgh HH, et al. (2009) Automated drug screening with contractile muscle tissue engineered from dystrophic myoblasts. FASEB J. 23: 3325-3334.
Vandenburgh HH. (1988) A computerized mechanical cell stimulator for tissue A888. culture: Effects on skeletal muscle organogenesis. In Vitro Cell Dev Biol. 24:609-619.
Varghese K, et al. (2009) Regeneration and characterization of adult mouse A889. hippocampal neurons in a defined in vitro system. J N eurosci Methods. 177: 51-59.
Varghese K, et al. (2010) A new target for amyloid beta toxicity validated by standard and high-throughput electrophysiology. PLoS One. 5: e8643.
Vargo TG, et al. (1992) Monolayer Chemical Lithography and Characterization of Fluoropolymer Films. Langmuir. 8: 130-1.
Vartanian T, et al. (1988) Oligodendrocyte substratum adhesion modulates expression of adenylate cyclase-linked receptors. Proc Natl Acad Sci US A. 85:939-943.
Ventimiglia R, et a. (1987) Localization of beta-adrenergic receptors on differentiated cells of the central nervous system in culture. Proc Natl Acad Sci USA. 84: 5073-507.
Vidarsson H, et al. (2010) Differentiation of human embryonic stem cells to cardiomyocytes for in vitro and in vivo applications. Stem Cell Rev. 6: 108-120.
Viravaidya K and Shuler ML. (2004) Incorporation of 3T3-LI cells to mimic bioaccumulation in a microscale cell culture analog device for toxicity studies. Biotechnol Prog. 20: 590-597.
Vogel V and Sheetz M. (2006) Local force and geometry sensing regulate cell functions. Nat Rev Mol Cell Biol. 7: 265-275.
Vogel Zand Daniels MP. (1976) Ultrastructure of acetylcholine receptor clusters on cultured muscle fibers. J Cell Biol. 69: 501-507.

(56) References Cited

OTHER PUBLICATIONS

Waataja JJ, et al. (2008) Excitotoxic loss of post-synaptic sites is distinct temporally and mechanistically from neuronal death. J Neurochem. 104: 364-375.
Waggoner PS and Craighead HG. (2007) Micro- and nanomechanical sensors for environmental, chemical, and biological detection. Lab Chip. 7: 1238-1255.
Wagner I, et al. (2013) A dynamic multi-organ-chip for long-term cultivation and substance testing proven by 3D human liver and skin tissue co-culture. Lab Chip. 13: 3538-3547.
Wakatsuki T, et al. (2004) Phenotypic screening for pharmaceuticals using tissue constructs. Curr Pharm Biotechnol. 5: 181-189.
Walro JM and Kucera J. (1999) Why adult mammalian intrafusal and extrafusal fibers contain different myosin heavy-chain isoforms. Trends Neurosci. 22: 180-184.
Walsh DM and Selkoe DJ. (2007) A beta oligomers—a decade of discovery. J N eurochem. 101: 1172-1184.
Walsh K, et al. (2005) Human central nervous system tissue culture: a historical review and examination ofrecent advances. Neurobiol Dis. 18: 2-18.
Wang HW, et al. (2002) Soluble oligomers of beta amyloid (1-42) inhibit long-term potentiation but not long-term depression in rat dentate gyrus. Brain Res. 924: 133-140.
Wang P, et al. (2005) Defective neuromuscular synapses in mice lacking amyloid precursor protein (APP) and APP-Like protein 2. J Neurosci. 25: 1219-1225.
Wang X, et al. (2008) Effects of interleukin-6, leukemia inhibitory factor, and A907. ciliary neurotrophic factor on the proliferation and differentiation of adult human myoblasts. Cell Mol Neurobiol. 28: 113-124.
Ward JH, et al. (2001) Micropatteming of biomedical polymer surfaces by novel UV polymerization techniques. J Biomed Mater Res. 56: 351-360.
Warf BC, et al. (1991) Evidence for the ventral origin of oligodendrocyte precursors in the rat spinal cord. J Neurosci. 11: 2477-2488.
Wende AR, et al. (2007) A Role for the Transcriptional Coactivator PGC-1 alpha in Muscle Refueling. J Biol Chem. 282: 36642-36651.
Wesierska-Gadek J, et al. (2003) Dual action of cyclin-dependent kinase inhibitors: induction of cell cycle arrest and apoptosis. A comparison of the effects exerted by roscovitine and cisplatin. Pol J Pharmacol. 55: 895-902.
White SM and Claycomb WC. (2005) Embryonic stem cells form an organized, functional cardiac conduction system in vitro. Am J Physiol Heart Circ Physiol. 288: H670-H679.
Wilson K, et al. (2006) Reflex-arc on a chip: An in silico cell culture analogue. NSTI-Nanotech. 2: 297-300.
Wilson K, et al. (2007) Integration of Functional Myotubes with a Bio-MEMS Device for Non-Invasive Interrogation. Lab Chip. 7: 920-922.
Wilson K, et al. (2010) Measurement of contractile stress generated by cultured rat muscle on silicon cantilevers for toxin detection and muscle performance enhancement. PLoS One. 5: e11042.
Wilson K, et al. (2011) Direct patterning of coplanar polyethylene glycol alkylsilane monolayers by deep-ultraviolet photolithography as a general method for high fidelity, long-term cell patterning and culture. J Vac Sci Technol B Nanotechnol Microelectron. 29: 21020.
Windebank AJ, et al. (1985) Myelination determines the caliber of dorsal root ganglion neurons in culture. J Neurosci. 5: 1563-1569.
Wink T, et al. (1997) Self-assembled Monolayers for Biosensors. Analyst. 122:R43-R50.
Winslow RL, et al. (2005) Using models of the myocyte for functional interpretation of cardiac proteomic data. J Physiol. 563: 73-81.
Wise KD, et al. (2004) Wireless Implantable Microsystems: High-Density Electronic Interfaces to the Nervous System. Proceedings of the IEEE. 92: 76-97.
Witzemann V. (2006) Development of the neuromuscular junction. Cell Tissue Res. 326: 263-271.
Wong ROL. (1998) Calcium imaging and multielectrode recordings of global patterns of activity in the developing nervous system. Histochem J. 30: 217-229.
Wood P, et al. (1990) Studies of the initiation ofmyelination by Schwann cells. Ann NY Acad Sci. 605: 1-14.
Wright CD, et al. (2008) Nuclear alphal-adrenergic receptors signal activated ERK localization to caveolae in adult cardiac myocytes. Circ Res. 103: 992-1000.
Wu H, et al. (2010) To build a synapse: signaling pathways in neuromuscular junction assembly. Development. 137: 1017-1033.
Wu P, et al. (2002) Region-specific generation of cholinergic neurons from fetal human neural stem cells grafted in adult rat. Nat Neurosci. 5: 1271-1278.
Wu ZR, et al. (2007) Layer-by-layer assembly of polyelectrolyte films improving cytocompatibility to neural cells. J Biomed Mater Res A. 81: 355-362.
Wyart C, et al. (2002) Constrained synaptic connectivity m functional mammalian neuronal networks grown on patterned surfaces. J Neurosci Methods. 117: 123-131.
Xi J, et al. (2005) Self-assembled microdevices driven by muscle. Nat Mater. 4:180-184.
Xu C, et al. (2006) Growth and differentiation of human embryonic stem cells for cardiac cell replacement therapy. Curr Stem Cell Res Ther. 1: 173-187.
Xu H, et al. (2008) Development of a stable dual cell-line GFP expression system to study estrogenic endocrine disruptors. Biotechnol Bioeng. 101: 1276-1287.
Xu L, et al. (2006) Human neural stem cell grafts ameliorate motor neuron disease in SOD-I transgenic rats. Transplantation. 82: 865-875.
Xu T, et al. (2004) Construction of high-density bacterial colony arrays and patterns by the ink-jet method. Biotechnol Bioeng. 85: 29-33.
Xu T, et al. (2005) Inkjet printing of viable mammalian cells. Biomaterials. 26:93-99.
Xu T, et al. (2006) Viability and electrophysiology of neural cell structures generated by the inkjet printing method. Biomaterials. 27: 3580-3588.
Xu T, et al. (2009) Electrophysiological characterization of embryonic hippocampal neurons cultured in a 3D collagen hydrogel. Biomaterials. 30: 4377-4383.
Yablonka-Reuveni Z. (1995) Development and postnatal regulation of adult myoblasts. Microsc Res Tech. 30: 366-380.
Yan J, et al. (2007) Extensive neuronal differentiation of human neural stem cell grafts in adult rat spinal cord. PLoS Med. 4: 318-33.
Yan Z, et al. (2002) Roscovitine: a novel regulator of P/Q-type calcium channels and transmitter release in central neurons. J Physiol. 540: 761-770.
Yang FS, et al. (2005) Curcumin inhibits formation of amyloid beta oligomers and fibrils, binds plaques, and reduces amyloid in vivo. J Biol Chem. 280: 5892-5901.
Yang J, et al. (2006) Synthesis and evaluation of poly( diol citrate) biodegradable elastomers. Biomaterials. 27: 1889-1898.
Yang L, et al. (2007) Increased asynchronous release and aberrant calcium channel activation m amyloid precursor protein deficient neuromuscular synapses. Neuroscience. 149: 768-778.
Yang LX and Nelson PG. (2004) Glia cell line-derived neurotrophic factor regulates the distribution of acetylcholine receptors in mouse primary skeletal muscle cells. Neuroscience. 128: 497-509.
Yang SY, et al. (2003) New class of ultrathin, highly cell-adhesion-resistant polyelectrolyte multilayers with micropatteming capabilities. Biomacromolecules. 4: 987-994.
Yang Y, et al. (2003) Neuronal cell death is preceded by cell cycle events at all stages of Alzheimer's disease. J Neurosci. 23: 2557-2563.
Yang Z, et al. (1999) Protein Interactions with Poly(ethylene glycol) Self-Assembled Monolayers on Glass Substrates: Diffusion and Adsorption. Langmuir. 15: 8405-8411.
Yankner BA. (1996) Mechanisms of neuronal degeneration in Alzheimer's disease. Neuron. 16: 921-932.
Yap FL and Zhang Y. (2007) Protein and cell micropatteming and its integration with micro/nanoparticles assembly. Biosens Bioelectron. 22: 775-788.

(56) References Cited

OTHER PUBLICATIONS

Yasuda SI, et al. (2001) A novel method to study contraction characteristics of a single cardiac myocyte using carbon fibers. Am J Physiol Heart Circ Physiol. 281: H1442-H1446.
Yeung CK, et al. (2007) Drug profiling using planar microelectrode arrays. Anal Bioanal Chem. 387: 2673-2680.
Yin SH, et al. (2005) Measuring single cardiac myocyte contractile force via moving a magnetic bead. Biophys J. 88: 1489-1495.
Zhao BL, et al. (1989) Scavenging effect of extracts of green tea and natural antioxidants on active oxygen radicals. Cell Biophys. 14: 175-185.
Zhou L, et al. (2005) Mechanistic model of cardiac energy metabolism predicts localization of glycolysis to cytosolic subdomain during ischemia. Am J Physiol Heart Circ Physiol. 288: H2400-H2411.
Zhou Z, et al. (1999) Block of HERG potassium channels by the antihistamine astemizole and its metabolites desmethylastemizole and norastemizole. J Cardiovasc Electrophysiol. 10: 836-843.
Zimmermann WH, et al. (2000) Three-dimensional engineered heart tissue from neonatal rat cardiac myocytes. Biotechnol Bioeng. 68: 106-114.
Zimmermann WH, et al. (2002) Tissue Engineering of a Differentiated Cardiac Muscle Construct. Circ Res. 90: 223-230.
Zorzano A, et al. (2003) Intracellular signals involved in the effects of insulin-A957. like growth factors and neuregulins on myofibre formation. Cell Signal. 15: 141-149.
Zurn AD, et al. (1996) Combined effects of GDNF, BDNF, and CNTF on motoneuron differentiation in vitro. J Neurosci Res. 44: 133-141.
Zweigerdt R, et al. (2003) Generation of confluent cardiomyocyte monolayers derived from embryonic stem cells in suspension: a cell source for new therapies and screening strategies. Cytotherapy. 5: 399-413.
Shuler ML. (Mar. 19, 2012) Functional In Vitro System for Drug Discovery. https://www.nibib.nih.gov/sites/default/files/S2_MShuler_FunctionalInvitroSystemsForDrugDiscovery.pdf.
Hierlemann et al., "CMOS-Based Bio/Chemosensor and Bioelectronic Microsystems", Procedia Chemistry, Elsevier, Amsterdam, NL, vol. 1, No. 1, Sep. 2009, pp. 5-8.
Jose Francisco Saenz Cogollo et al., "A Novel AFM-MEA Platform for Studying the Real Time Mechano-Electrical Behavior of Cardiac Myocytes", MRS Proceedings, vol. 1261, 2010, pp. 17-22.
Park et al., Neuromuscular Junction in a Micrifluidic Device, 35th Annual International Conference of the IEEE EMBS Osaka, Japan, Jul. 3-7, 2013.
Smith et al., A functional system for high-content screening of neuromuscular junctions in vitro, Technology (Singap World Sci) 2013; 1(1):37-48. doi:10.1142/S2339547813500015.
Natarajan et al., Patterned Cardiomyocytes on Microelectrode Arrays for High-Throughput Functional Side Effect Screening with Enhanced Information Content, Oct. 21-23, 2008.
Todorova et al., Transducers and Eurosensors '07, 2007 International Solid-State Sensors, Actuators and Microsystems Conference (2007).
Liu et al., Current Organic Chemistry, vol. 15, pp. 477-485 (2011).
Pramanik et al., Journal of Micromechanics and Microengineering, vol. 16, No. 10, pp. 2060-2066 (2006).
Cogollo, Jose F. Saenz, et al. "A new integrated system combining atomic force microscopy and micro-electrode array for measuring the mechanical properties of living cardiac myocytes." Biomedical microdevices 13.4 (2011): 613-621. (electronically published Apr. 1, 2011).
Office action issued for U.S. Appl. No. 14/764,683, dated Aug. 2, 2018.
Office action issued for U.S. Appl. No. 14/764,683, dated Feb. 20, 2019.
Office action issued for U.S. Appl. No. 14/764,683, dated Jun. 13, 2019.
Office action issued for U.S. Appl. No. 14/764,683, dated Jan. 7, 2020.
Advisory action issued for U.S. Appl. No. 14/764,683, dated Apr. 13, 2020.
Office action issued for U.S. Appl. No. 14/422,082, dated May 9, 2016.
Office action issued for U.S. Appl. No. 14/422,082, dated Nov. 28, 2016.
Office action issued for U.S. Appl. No. 14/422,082, dated Oct. 5, 2017.
Office action issued for U.S. Appl. No. 14/422,082, dated Jul. 27, 2018.
Advisory action issued for U.S. Appl. No. 14/422,082, dated Jan. 4, 2019.
Office action issued for U.S. Appl. No. 14/422,082, dated Feb. 6, 2020.
Advisory action issued for U.S. Appl. No. 14/422,082, dated Apr. 5, 2017.
Office action issued for U.S. Appl. No. 14/422,082, dated May 31, 2019.
Office action issued for U.S. Appl. No. 15/190,958, dated Aug. 31, 2018.
Office action issued for U.S. Appl. No. 15/190,958, dated Jun. 3, 2019.
Office action issued for U.S. Appl. No. 15/190,958, dated Mar. 16, 2020.
Advisory action issued for U.S. Appl. No. 15/190,958, dated May 18, 2020.
Office action issued for U.S. Appl. No. 14/821,675, dated Sep. 20, 2017.
Office action issued for U.S. Appl. No. 14/821,675, dated May 31, 2018.
Office action issued for U.S. Appl. No. 14/821,675, dated Mar. 14, 2019.
Advisory action issued for U.S. Appl. No. 14/821,675, dated Sep. 13, 2019.
Office action issued for U.S. Appl. No. 14/821,675, dated Apr. 6, 2020.
Notice of Allowance issued for U.S. Appl. No. 15/594,697, dated Apr. 4, 2019.
Office action issued for U.S. Appl. No. 12/661,323, dated Mar. 13, 2013.
Office action issued for U.S. Appl. No. 12/661,323, dated Nov. 5, 2013.
Office action issued for U.S. Appl. No. 12/661,323, dated Mar. 18, 2015.
Office action issued for U.S. Appl. No. 12/661,323, dated Aug. 7, 2015.
Office action issued for U.S. Appl. No. 12/661,323, dated May 5, 2016.
Office action issued for U.S. Appl. No. 12/661,323, dated Dec. 13, 2016.
Advisory action issued for U.S. Appl. No. 12/661,323, dated Nov. 4, 2015.
Office Action issued in Canadian Patent Application No. 2,899,445 dated Nov. 6, 2019, 3 pages.
Supplementary European Search Report issued in European Application No. EP 14745661, dated Aug. 10, 2016.
Extended European Search Report issued in European Application No. EP 14745661, dated Aug. 19, 2016.
Communication Pursuant to Article 94(3) issued in European Application No. EP 14745661, dated Apr. 10, 2017.
Communication Pursuant to Article 94(3) issued in European Application No. EP 14745661, dated Aug. 18, 2017.
International Search Report and Written Opinion of the International Searching Authority from Application No. PCT/US2013/055617, dated Dec. 17, 2013 (10 pages).
International Search Report and Written Opinion for International Application No. PCT/US2014/013903 mailed May 15, 2014, 13 pages.

\* cited by examiner

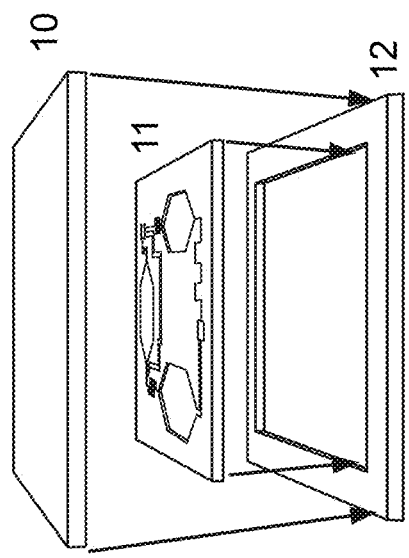
FIG. 1A
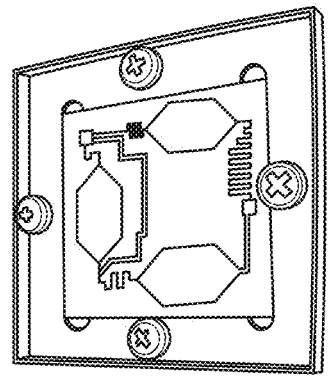
FIG. 1B
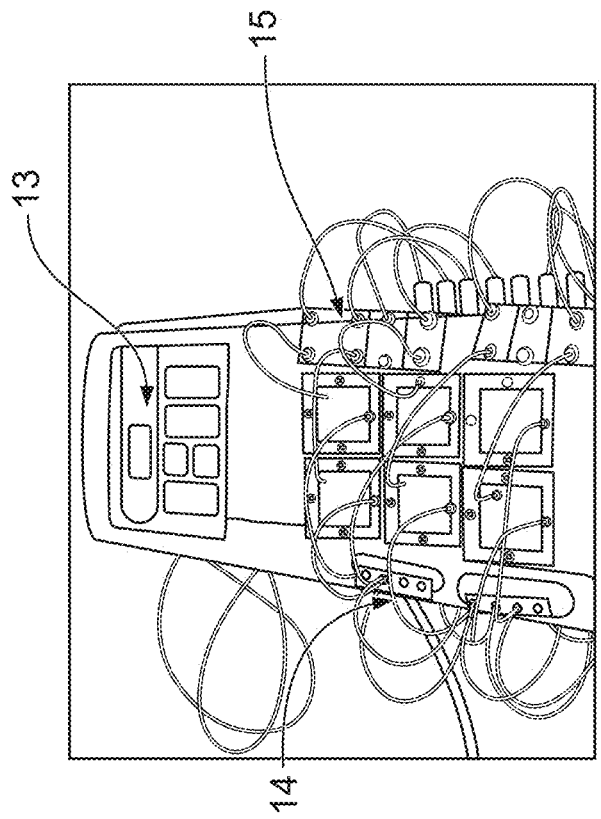
FIG. 1C
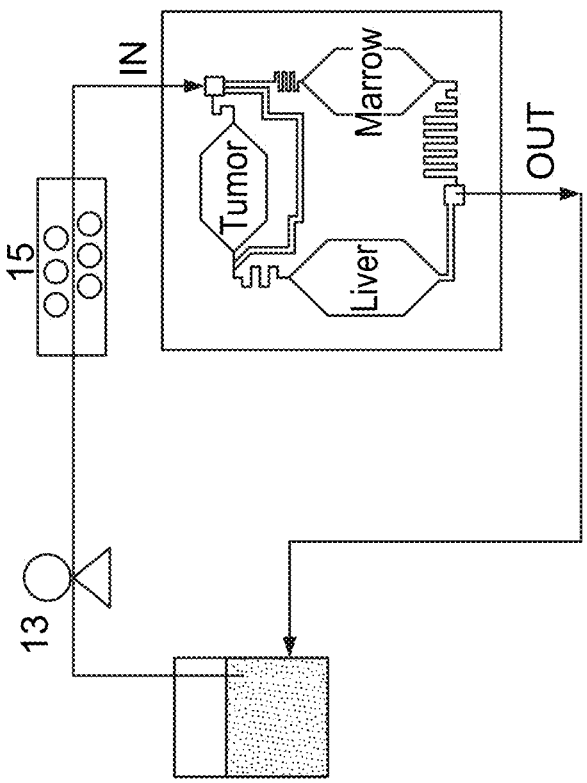
FIG. 1D

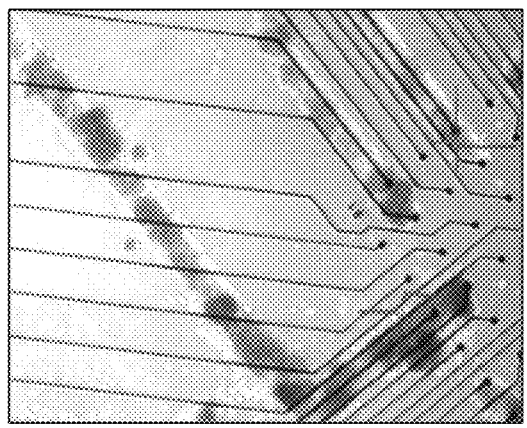
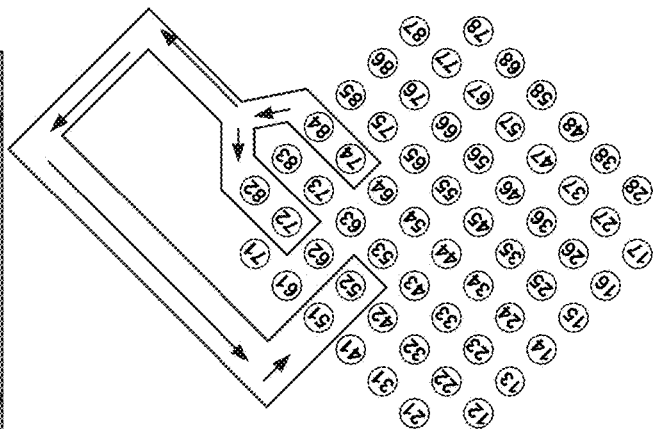
FIG. 3A  FIG. 3B
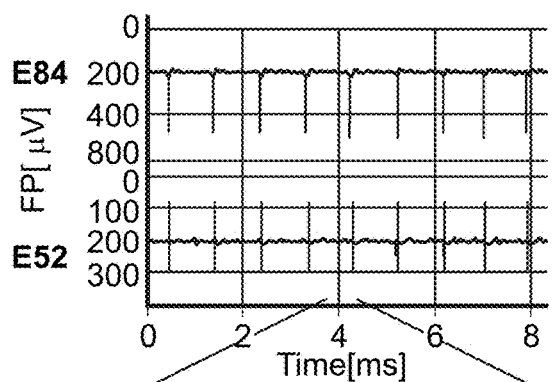
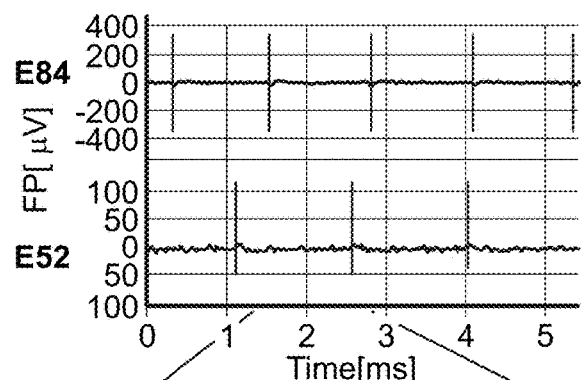
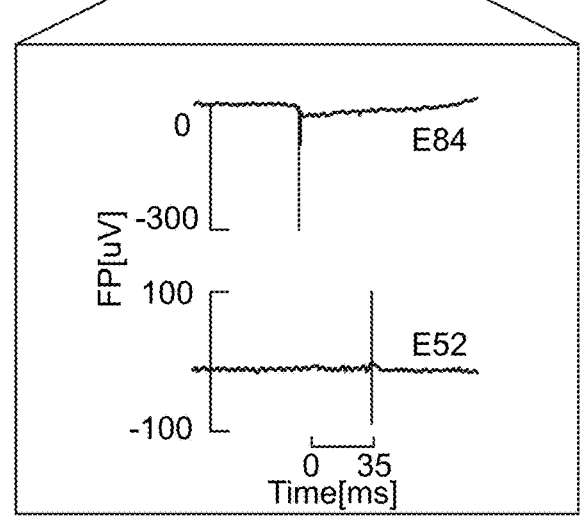
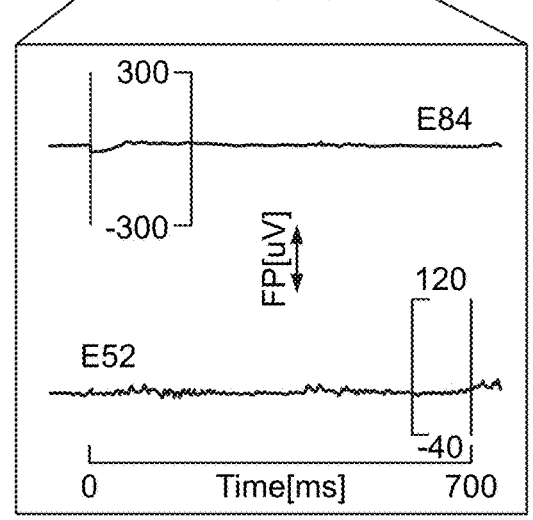
FIG. 3C  FIG. 3D

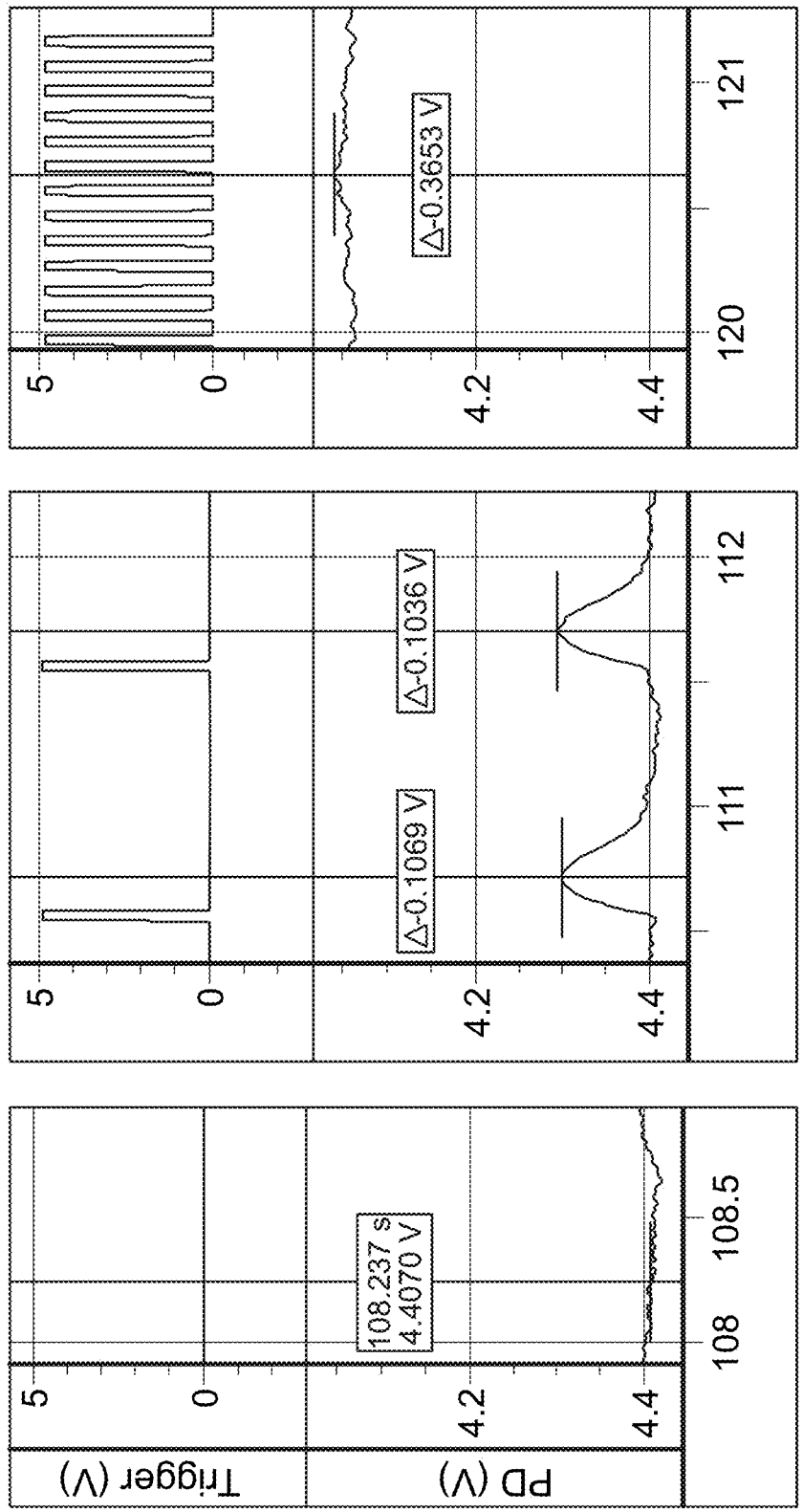

METHODS, SYSTEMS AND COMPOSITIONS FOR FUNCTIONAL IN VITRO CELLULAR MODELS OF MAMMALIAN SYSTEMS

CROSS-REFERENCE TO RELATED APPLICATIONS

The present application is a continuation of U.S. application Ser. No. 14/422,082, filed Feb. 17, 2015, which is a U.S. National Phase Application of International Application No. PCT/US2013/055617, filed Aug. 19, 2013, which claims the benefit of priority to U.S. Provisional Patent Application No. 61/684,168 filed Aug. 17, 2012 and U.S. Provisional Patent Application No. 61/789,184 filed Mar. 15, 2013. Each of the aforementioned applications is incorporated herein by reference in its entirety.

STATEMENT REGARDING FEDERALLY SPONSORED RESEARCH

This invention was made with government support under Contract No. W81XWH-10-1-0542 awarded by U.S. Army Medical Research and Material Command. The government has certain rights in the invention.

FIELD OF THE INVENTION

Disclosed herein are methods, systems and compositions relating to functional in vitro cell culture devices to mimic mammalian organ systems.

BACKGROUND

The major research uses of animals are both in assessing potential toxicity of chemicals and in drug testing. Animal tests often are long in duration, expensive, and raise ethical issues. Further, animal tests are not always predictive of human response. This fact is easily demonstrated in drug development where only 11% of chemicals exiting animal trials are successful in humans [Hughes 2007]. In terms of human response to environmental toxicants, it is not ethically possible to conduct direct tests on humans, and extrapolation of animal results to human response is problematic. Over-regulation results in unnecessary expense; under-regulation endangers human health and the environment, so better testing systems are necessary.

In vitro tests can supplement and may reduce dependency on animal tests. However, current in vitro tests fail to capture many important aspects of human and mammalian response to chemicals. Most in vitro tests are based on the use of multi-well plates where isolated cells or tissues are placed in medium spiked with a bolus dose of the test chemical. Such systems miss key aspects of physiological response. For example, the dose dynamics in the body differ considerably from static systems as time-dependent changes in chemical concentration occur in the body at a tissue site due to the processes controlling absorption, distribution, metabolism and excretion of a compound. Further, static well systems typically use a single cell or tissue type; in the body, metabolites are exchanged between different tissue/organ compartments. Even if multiple tissue types were represented in a single well, the ratio of one tissue to another and the nature of the circuits connecting them can alter the time-dependent concentration of the metabolites. In addition to these factors, single cells in a well, in most cases, do not represent functional tissues or subsystems of the body, nor experience the mechanical forces the cells in the body do, particularly those associated with fluid flow, and these mechanical forces are known to alter gene expression and metabolism of many chemicals. What is needed in the art is a cell culture analog device (a component) and methods and systems thereof, comprising biologically functioning cells that mimic interactions of tissues, organs and whole organism systems.

SUMMARY

Disclosed are methods, systems and compositions comprising one or more cell culture analog devices, comprising biologically functional cells, animal or human, which function similarly to or mimic in vivo physiological conditions of whole organs or living organisms. For example, a component may comprise cardiac myocytes on microelectrode arrays.

Disclosed are cell culture analog systems comprising one or a plurality of components. A component may comprise a microscale cell culture device, also referred to as a μCCA device which may comprise cells. A component, with or without cells contained within a chamber, and/or other elements, is analogous to an organ or organ system. A component may comprise a container for cells, such as a chamber, in which cells are contained, grown, acted on and/or maintained in the chamber. For example, a component may comprise, but is not limited to, a cardiac component comprising patterned biologically functional cardiac myocytes on microelectrode arrays, a hepatic component comprising liver cells, a gastrointestinal component comprising cells such as epithelial cells and/or mucus-producing cells, a muscular component comprising muscle cells, a kidney-like filtering component, an "other tissues" component, a neural component, a neuromuscular component or other components analogous to body structures, organs or organ systems.

A cell culture analog system of the present invention may comprise one component, two components, three components, four components, five components, six components, seven components, eight components or more than eight components. It is contemplated that in a plurality of components each component is different from the other components, for example, different in that each component has one type of cells or has one physiological function. For example, a cell culture analog system may comprise a plurality of components comprising a cardiac component, a hepatic component, a neural component, a motoneuron component, and a muscle component. For example, a cell culture analog system may comprise a plurality of components comprising a cardiac component, a hepatic component, a motoneuron component, and a muscle component. For example, a cell culture analog system may comprise a plurality of components comprising a cardiac component, a neural or motoneuron component, and an other tissues component. The components can be combined in any desired number and manner to form a cell culture analog system that can mimic or simulate physiological conditions in a living subject such as a human or an animal. In an aspect, fluid can be moved in the system using pumps or by utilizing gravity driven fluid movement technology. In an aspect, static culture in multiple well systems can also be used in certain applications.

Further disclosed are methods for determining the effect of an input variable on one or more components, comprising contacting the one or more components with at least one input variable and monitoring at least one output parameter. For example, one or more components may be used for example, in a non-limiting listing, the testing of compounds, the effects of infectious agents, the effects of immune response cells or cellular factors, cellular factors, hormones, molecules, gases, and environmental effects on in vitro whole body systems (such as pressure or atmospheric changes), or other input variables to be tested on a living organism.

Disclosed is a cell culture analog system, comprising a plurality of components such as micro cell culture analog devices, for example, wherein one or more components is a component comprising patterned biologically functional cardiac myocytes on microelectrode arrays, a component for measurement of muscle or cardiac cell responses using a cantilever, a hepatic component comprising liver cells, a gastrointestinal component comprising epithelial cells and/or mucus-producing cells, a muscular component comprising muscle cells, a kidney-like filtering component, an "other tissues" component, a neural component, and/or other component analogous to body structures, organs or organ systems, and optionally, further comprising housing for enclosing the component, or a planar solid material for immobilizing one or a plurality of components in a system. A component may comprise a microscale chamber having a geometry simulating an in vivo interaction with cells and culture medium, wherein the chamber comprises a first inlet and a first outlet for flow of the culture medium and channels or connections coupled to the inlet(s) and outlet(s) of the chamber. An "other tissues" compartment represents and is analogous to fluid retained in nonabsorbing, nonadsorbing, nonmetabolizing tissues that simulate the dynamics of fluid flow or blood flow in a cell culture analog system.

The present invention comprises methods, systems and means for dynamically controlling a cell culture analog system, for example, comprising a computer and other elements, such as processors, sensors, actuators, etc., wherein, in an aspect, a method comprises analyzing data from a plurality of sensors to measure physiological events in one or more chambers of one or more components disclosed herein; optionally, regulating a cell culture characteristic such as temperature, light, oxygen, carbon dioxide, and/or fluid flow rates of a culture medium in at least one chamber of a component; or regulating the position of the component or a portion of a component in three dimensional space, and detecting biological or toxicological reactions in the cells or other elements of a component; and optionally, upon detection, recording the change and/or reacting to or changing one or more parameters of a component.

The present invention comprises a computer-readable medium having computer-executable instructions stored thereon to perform a method. For example, a method may comprise analyzing data from a plurality of sensors to measure physiological events in one or more chambers of one or more components disclosed herein; optionally, regulating a characteristic such as temperature, light, oxygen, carbon dioxide, and/or fluid flow rates of a culture medium in at least one chamber of a component; and detecting biological or toxicological reactions in the cells or other elements of one or more chambers of a component; and optionally, upon detection, recording the change and/or changing one or more pharmacokinetic parameters of a component.

BRIEF DESCRIPTION OF THE DRAWINGS

FIGS. 1A-1D show photographs and schematic diagram of an exemplary μCCA, a component. FIG. 1A shows a silicon μCCA chip (11) sandwiched between a Plexiglas top cover (10) and an aluminum bottom housing (12) with a recess for the chip and a silicon rubber gasket. The scaling was secured by screws around the edges of the housing. The channels and chambers in the chip were made in silicon with conventional photolithographic techniques using a plasma ion etcher. Channel and chamber dimensions were chosen to replicate PBPK physiological based pharmacokinetic (PBPK) model values for distribution of cardiac output, fluid residence time in a "tissue", and the correct relative sizes of organs/tissues. FIG. 1B shows a picture of an assembled μCCA to show chambers and channels. FIG. 1C shows a schematic diagram of operation for a cell culture analog system with full re-circulation of medium acting as a blood surrogate. The "other tissues" compartment (14) represented fluid hold-up in non-adsorbing, non-metabolizing tissues to capture the dynamics of exposure to a chemical. It also acts as a debubbler or bubble trap (15) which aids in reliable operation for at least 72 hours. Pump (13) exists between bubble trap (15) and other tissues compartment (14). FIG. 1D shows a picture of a standard set-up using a peristaltic pump and 6 units [Sung 2009].

FIG. 2A shows a phase contrast picture of cardiac myocytes cultured on the electrodes. FIG. 2B shows a sample recording with the MEA system. FIG. 2C shows a graph of the effect on spontaneous firing frequency.

FIGS. 3A-3D show field potential recordings from patterned neonatal cardiomyocytes. FIG. 3A shows a patterned monolayer on electrode arrays on day 12 showing field potentials at individual electrodes. FIG. 3B shows a map of electrodes and direction of excitation spread based on spiking activity and time delays. FIG. 3C and FIG. 3D show the effect of the gap junction blocker 1-Heptanol. FIG. 3C shows the time delay between action potentials on electrodes 84 and 52 (see FIG. 3B for geometry) before addition of the drug. The conduction velocity (CV) was measured as 0.22 m/sec. FIG. 3D shows the time delay between the two electrodes after Heptanol exposure. The CV was calculated as 0.011 m/sec after drug administration.

FIG. 4A shows a PBPK model. FIG. 4B shows a schematic of device with pump (43), other tissues compartment (44), and bubble trap (45).

FIG. 8A shows a micrograph using a 5× objective, and FIG. 8B shows a micrograph using a 20× objective.

FIG. 9A shows a PBPK model. FIG. 9B shows a schematic of the device.

FIG. 10A shows a SEM micrograph of a silicon cantilever array at low magnification (60×). FIG. 10B shows a high magnification (14000×) image used to measure the thickness of the cantilever. Both images were taken at 50 u from normal. FIG. 10C shows a schematic representation of a functioning array. Muscle cells are plated on top of silicon cantilevers and differentiated into primary muscle fibers (myotubes). As these cells contract, they cause the cantilever substrate to bend. Force is calculated using a laser directed onto the cantilever tip. As the cantilever bends in response to myotube contraction, it causes displacement of the laser beam which can be measured (in Volts) using a photo-detector and then mathematically converted into a measurement of force (in Newtons). Further complexity can be added to this system through incorporation of supporting cell types, such as motoneurons (illustrated in red).

FIGS. 11A-11D are graphs of the establishment and characterization of a functional system designed to assess skeletal muscle contraction in vitro. FIG. 11A shows representative traces illustrating selective stimulation and control of contraction achieved using broad field electrical stimulation. Timed electrical pulses (illustrated in the upper trace) correlate to the functional contractile activity on cantilevers as measured by laser deflection (lower trace). FIGS. 11B-11D demonstrate that complete temporal control can be elicited over myotube activity. FIG. 11B shows that without stimulation, no muscle activity is observed. FIG. 11C shows low frequency pulses induce individual contractions. FIG. 11D shows that high frequency stimulation pushes the cell into a tetanic contraction.

FIG. 12A shows time to fatigue (measured as time taken for contractile force to reach half its initial measurement) using cells from wild type (WT) mice. FIG. 12B shows time to fatigue using cells derived from PGC-1 αβ knock-out mice. PGC-1 is involved in mitochondrial biogenesis and knockout animals consequently display significantly reduced endurance. A phenotype mirrored in this in vitro assay.

FIG. 13A shows that broad field electrical stimulation pulses used to elicit myotube contraction can be used to exercise the cells and the effect of this treatment can then be effectively measured and quantified using our laser and photo-detector system. FIG. 13B shows initial peak force (PF) measurements (in Volts) from cells subjected to one week CLFS compared with age-matched, un-stimulated controls. FIG. 13C shows time to fatigue (TTF) measurements (in seconds) from cells subjected to one week CLFS compared with age-matched, un-stimulated controls.

FIG. 14A shows a schematic representation of integrated MEAs and cantilevers on a single chip for measurement of whole heart function. FIG. 14B shows a phase contrast image of cardiac cells growing on cantilevers. FIG. 14C shows a representative trace for a laser and photo-detector system demonstrating contractile function of cultured cardiac cells. FIG. 14D shows phase contrast imaging demonstrating chemical patterning of a MEA culture surface to control cardiomyocyte adhesion and development. FIG. 14E demonstrates that the use of such patterning allows for measurement of signal transduction and potentiation across cellular monolayer networks. FIG. 14F demonstrates that treatment with drugs, such as norepinephrine, elicits alteration of spontaneous firing rates in cultured cardiomyocytes, mimicking the phenotypic response of the native tissue in vivo.

FIG. 16A and FIG. 16C show phase contrast images of human stem cell derived motoneurons on DETA/13F polarity patterns at 2 and 8 days in vitro, respectively. FIG. 16B and FIG. 16D show metallization images of the corresponding polarity patterns with 20 μm somal adhesion site.

FIG. 17A shows a schematic representation of our lung on a chip device modeling an alveolus (top) and layout of fluid side of lung-based body-on-a-chip device fabricated in silicon (bottom). The bottom panel shows bubble trap as 171, conditioning chamber as 172, alveolar chamber as 173, bubble trap as 174 and sensor chambers as 175. FIG. 17B shows a simulation of gas sensor function measuring $CO_2$ fluctuation using the geometry of the silicon lung model in FIG. 17A. Water at the inlet was in equilibrium with breathing air. The gas above the membrane was initially at 5% $O_2$ and 5% $CO_2$, was switched to 10% $O_2$ and 10% $CO_2$ and allowed to equilibrate, and then switched back. The boundary condition that represents the membrane is a fixed-concentration boundary; the membrane is very thin and quickly comes into equilibrium with the gas above it. The dissolved gas concentrations after the alveolar chamber were measured in the first sensor chamber (oxygen) and the second sensor chamber ($CO_2$).

FIG. 18A shows tilt direction and flow path options may produce two or more separate flows of compositions, such as media, and the flows may have the same or different flow rates or ratios of mixing. FIG. 18B1 (left) and FIG. 18B2 (right) shows particular flow paths. FIG. 18C1 (left) and FIG. 18C2 (right) shows mixing ratios for mixing two compositions.

FIG. 19A shows a stacked embodiment comprising a plurality of components in a three-dimensional relationship with one another. FIG. 19B shows a cell culture analog system comprising a planar relationship of a plurality of components in fluid connection that is formed within a planar rectangular form. FIG. 19C shows a cell culture analog system comprising a planar relationship of a plurality of components in fluid connection. FIG. 19D shows a cell culture analog system comprising a planar relationship of a plurality of components in fluid connection that is formed within a planar rectangular form.

DETAILED DESCRIPTION

Figure 2A:
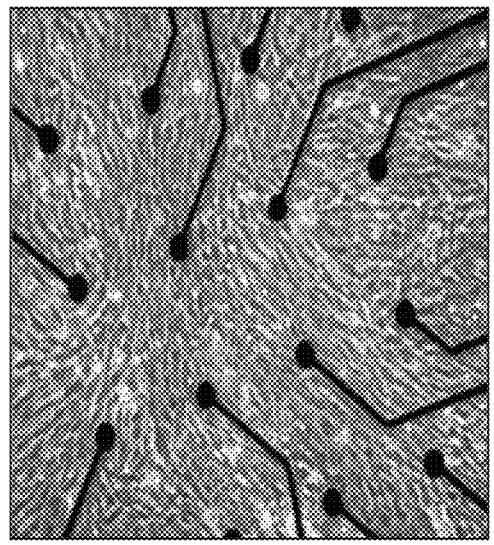
FIGS. 2A-2C show the effect of pyrethroids on the firing frequency of chicken cardiac myocytes measured by multielectrode recordings of extracellular action potentials.

Over time, cell culture medium has evolved from a simple salt solution to preserve tissue to more complex compositions, which can be used to maintain cells and tissues for extended periods of time. Human or animal sera, the most commonly used being fetal bovine serum, can be used to supplement basic media since they contain essential compounds for the growth and maintenance of cells.

To improve the quality, consistency and definition of the culture medium, serum free mediums can be used. Variations in mediums are known to affect cell culture maintenance and subsequent experimental data (Van der Valk et al., 2010). Serum-free media formulations can be based on the addition of cell-specific growth factors and supplements to a common base medium in order to facilitate the correct maintenance of specific cell cultures (Edwards et al., 2010). For example, following the first serum-free defined culture system for hippocampal neurons (Schaffner et al., 1995), a defined serum-free medium has been used with cardiomyocytes (Natarajan et al., 2011), motoneurons (Das et al., 2003), sensory neurons (Rumsey et al., 2010), and skeletal muscle cells (Das et al., 2006). In an aspect, in vitro cell-cultures can be designed to mimic the relevant in vivo environment. For example, a temperature of 37° C., and a controlled humidified gas mixture of 5% $CO_2$ and 95% $O_2$ can be used as the standard physical conditions. A blood surrogate medium with appropriate micro and macronutrients can be used to recreate the chemical milieu.

With respect to the disclosed systems, an advancement in the formulation of serum-free media was needed. These disclosed systems can maintain different cell types in a single housing; thus, it is a challenge to identify a common, serum-free formulation that can preserve functionality and morphological phenotypes of the different cells in co-culture. The need to maintain in vitro models for extended periods is of great importance for drug development applications. Assessment of chronic compound exposure to various tissues, and understanding the effects of prolonged metabolite or waste build-up in specific organ compartments can be essential for obtaining accurate predictions of in vivo responses to drug treatment.

Typical in vitro assessment of cell functionality and maturation within novel micro-devices designed for drug development applications takes place over 1 to 2 weeks in culture. Such time frames have been employed for the assessment of a wide variety of in vitro analogues, including cardiac (Natarajan et al., 2011, Agarwal et al., 2013), lung (Huh et al., 2010), kidney (Subramanian et al., 2010), liver (Wagner et al., 2013), pancreas (Lipsett et al., 2007), skin (Bellas et al., 2012), fat (Kang et al., 2009) and neuronal (Natarajan et al., 2013) tissue models, with little information provided regarding more long-term survival. Longer in vitro culture periods tend to lead to cellular senescence or induction of apoptotic pathways, which can confound data analysis. While useful for a wide variety of basic biomolecular research, such timeframes are of more limited value for the study of chronic disease states and long term drug toxicity studies. Furthermore, when designing multi-organ systems for more accurate modeling of whole body responses (Sung et al., 2013), uniformity with regards to cell survival over extended time periods is preferable. An ability to maintain certain cells for 30 days in vitro is immaterial if other cells within the same culture platform begin to die after 14.

Longer culture periods have been established for certain cell types, and assessment of their development and functional maturation over such timeframes has been assessed. For example, skeletal muscle cultures have been shown to survive in vitro for up to 90 days, during which time they promote phenotype maturation, as evidenced by quantifiable changes in Myosin Heavy Chain isoform composition (Das et al., 2009). The systems disclosed herein can promote the long-term (30+ days) co-culture and functional interaction of skeletal muscle myotubes and motoneurons in defined conditions. The data provided herein demonstrate that maintenance of co-cultures is possible over longer periods provided careful consideration is given to culture variables such as surface, media formulation and correct temporal addition of exogenous stimuli.

The present invention comprises an in vitro model of biological living systems, such as animals or humans, for example, in response to chemicals or chemical mixtures. Such a model that mimics or simulates in vivo living biological systems reduces dependency on animal testing while providing improved predictions of responses of human or other organisms, such as plants, animals or insects. The present invention comprises micro cell culture analog (µCCA) methods, systems, and devices. These methods, systems and devices comprise microfabrication techniques, cell culture/tissue engineering and micro fluidics. A µCCA device, also referred to herein as "a cell culture analog system device." or a "component", is a physical representation of a physiologically-based pharmacokinetic (PBPK) model, and the functional in vitro systems reproduce in vivo effects of living tissues and organs, such as cardiac pacemaking, muscle dynamics, and neuronal information processing.

The present invention comprises cell culture analog systems comprising one or a plurality of components comprising cells grown in a microscale cell culture device, also referred to as a µCCA device, comprising one or more chambers or regions, wherein a component, along with cells contained therein a chamber or otherwise, and/or other elements, is analogous to a tissue, an organ or organ system. A component comprises a substrate for cells, such as a container for cells, a chamber, in which cells are contained, grown, acted on and/or maintained in the component. For example, a component may comprise, but is not limited to, a cardiac component comprising patterned biologically functional cardiac myocytes on microelectrode arrays. See U.S. patent application Ser. No. 12/938,701, which is incorporated by reference herein in its entirety for disclosing patterned rat cardiomyocyte cultures on microelectrode arrays in a serum-free medium for the study of cardiac physiology and pharmacology, utilizing a high-throughput technique. A disclosed component comprises a support substrate bearing a multielectrode array (MEA) and a negative surface resistant to cell attachment and deposited on the support substrate covering the MEA. The negative surface bears a pattern ablated on it by, for example, laser photolithography. A positive surface promoting cell attachment is deposited on the pattern ablated on the negative surface and cardiomyocytes adherent to the positive surface and growing aligned along the pattern. This application also teaches methods of making the culture of patterned cardiomyocytes. For example, a method comprises preparing a support substrate bearing a MEA, overlaying on the support substrate a negative surface resistant to cell adherence. The surface can comprise polyethylene glycol covering the MEA. Further, the method comprises ablating a pattern on the negative surface, depositing on the ablated pattern a positive surface promoting cell adherence and including fibronectin, adhering cardiomyocytes on the positive surface, and culturing the cardiomyocytes to grow on the positive patterned surface and align with the patterned surface.

A component may comprise more than one type of cell and may simulate organ systems which are comprised of more than one type of cell. Multicellular interactions, such as between the same cells and/or between different types of cells are included in the methods and compositions of the present invention. For example, muscle and neurons, which function in communication in a living body, may be provided in a single component and the cells may form neuromuscular junctions between the neurons and the muscle cells. Cells with genetic alterations may be used in methods and compositions of the present invention.

In an aspect, a component may comprise a muscular component comprising muscle cells. See U.S. patent application Ser. No. 12/765,399, which is incorporated by reference herein in its entirety for disclosing methods for lengthening the useful life of a culture of muscles cells by using disclosed mixtures of serum-free media, supplemented with growth factors. Tables 1 and 2 show the individual growth factors, hormones, and neurotransmitters that support muscle and neuromuscular junction development. For example, the composition shown in Table 1 is a formulation for a serum-free medium for culturing motor neurons with adult spinal cord neurons. Table 2 lists additional factors identified in muscle development and neuromuscular junction formation. NBactiv4, used for maintenance of the cells, improves the survival of the skeletal muscle cells.

In an aspect, a component can comprise a neural component. See U.S. patent application Ser. No. 12/117,339, which is incorporated by reference herein in its entirety for disclosing a method of culturing adult mammalian spinal cord neurons so that they exhibit electrical functionality. Table 3 shows a non-limiting example of a serum-free culture medium used in the disclosed method.

In an aspect, a component can comprise a kidney-like filtering region, an "other tissues" region, and/or other regions analogous to body structures, organs or organ systems.

In an aspect, a cell culture analog system may comprise a hepatic component comprising liver cells, a gastrointestinal component comprising epithelial cells and/or mucus-producing cells.

The present invention comprises methods for determining the effect of an input variable on a culture of cells, comprising contacting the cells of one or a plurality of components with an input variable and monitoring at least one output parameter. For example, a cell culture analog system may comprise a plurality of components comprising an hepatic (liver) component, a cardiac component, a motoneuron component, and a muscle component may be used for testing compounds found in compositions that are commercially available, such as personal care compositions.

Also provided is cell culture analog system as disclosed herein, comprising one or a plurality of components, for example, comprising one or more of patterned biologically functional cardiac myocytes on microelectrode arrays, a hepatic component comprising liver cells, a gastrointestinal component comprising epithelial cells and/or mucus-producing cells, a muscular component comprising muscle cells, a kidney-like filtering component, an "other tissues region", a neural component, a neuromuscular component and/or other components analogous to body structures, organs or organ systems, and optionally, further comprising housing for enclosing the components or a board for immobilizing components. A component may comprise a first microscale chamber having a geometry simulating a first in vivo interaction with culture medium, wherein the first chamber comprises a first inlet and a first outlet for flow of the culture medium, and one or more channels coupled to the inlets and outlets of the chamber. An "any other tissues compartment or "other tissues compartment" represents fluid hold-up or retention in non-adsorbing, non-metabolizing tissues which captures the dynamics of exposure to a chemical in the cell culture analog systems.

An aspect of the present invention comprises a component that mimics or simulates heart function in organisms, such as a human, animal or insect, comprising cardiac myocytes, surface embedded microelectrodes and patterned substrates on the microelectrode array to monitor the condition of the cardiac chamber in the μCCA in real time and detect both acute and chronic functional toxic effects on the system.

Cultured cardiac myocytes are widely used in toxin detection and in drug development to screen for unwanted cardiac side effects [Meyer 2004]. Cardiac myocytes are almost ideal whole-cell biosensors as they are spontaneously active, can be kept in culture in stable conditions for extended periods [Dhir 2009] and they respond to a wide spectrum of known and unknown toxins. Patterning cardiac myocytes on microelectrode arrays allows for the measurement of more advanced parameters, such as reverse use dependence, variability in QT interval and relative refractory periods [Natarajan 2011].

A cell culture analog system of the present invention comprises one or a plurality of components, which provide in vitro reproduction or simulation of a living body, with each component representing an organ or tissue in the living body. In a PBPK mathematical model, these chambers are interconnected in a manner analogous to blood flow in the body. In a μCCA or component, the equations representing metabolism or adsorption in these chambers or compartments are replaced by living cells or tissues (e.g. liver, fat, lung, etc. all in the same device). Systems and devices of the present invention may be used for research, testing, diagnosis and insight into underlying biochemical mechanisms and how function is affected. By inserting functional tissues into components comprising mammalian cells or tissues, response from exposure to active agents, such as environmental chemicals, can be measured.

Components, systems and methods can be used with both animal cells and human cells, and non-animal cells such as insect or plant cells, and methods may comprise cross-species extrapolation. A basic concept of a μCCA has been demonstrated with studies on naphthalene toxicity [Sin 2004; Viravaidya 2004] on drug combinations to treat multidrug resistant cancer [Tatosain 2009] or colon cancer [Sung 2009] and, in preliminary studies, on hormone disruptors [Xu 2008]. The functional in vitro systems have been demonstrated for cardiac [Natarajan 2011; Natarajan 2006; Das 2004], neuronal [Jung 1998; Mohan 2006], muscle (Das 2007; Wilson 2007; Wilson 2010) and neuromuscular junction [Das 2010, Liu 2005) systems. See U.S. patent application Ser. No. 12/765,996, which is incorporated by reference herein in its entirety for disclosing long term in vitro cultures of tissue engineered functional neuromuscular junctions. Tables 1, 2, and 3 show the serum-free medium used in the disclosed methods. See also U.S. patent application Ser. No. 13/102,672, which is incorporated by reference herein in its entirety for disclosing the formation of neuromuscular junctions in a defined system by co-culturing one or more human motor neuron cells and one or more rat muscle cells in a substantially serum-free medium. Tables 1, 2, and 3 represent non-limiting examples of serum-free media used in the disclosed methods.

For the validation of the integrated cardiac myocyte reporter construct and a μCCA, the effect of metabolism on the functional effects of stereoisomers of permethrin, a pyrethroid and an environmental toxin, was measured (Example 1). The role of enantioselectivity in environmental safety is poorly understood for pesticides, and the knowledge gap is reflected in that the great majority of chiral pesticides are used and regulated as if they were achiral, that is, single compounds. Stereoisomerism is critically important for pyrethroid toxicity; it determines not only their efficacy on their main target, but more importantly, their metabolic rate. Components, arrays and methods are ideal in vitro systems to study the effect of metabolism on the effect of environmental toxins in a system that is adaptable to a high-throughput format. For example, an in vitro system that allows for the observation of functional units derived from human cells/tissues is advantageous for environmental toxin studies. In a non-limiting example, human stem cells can be used for more authentic constructs leading to human-based components, arrays, and methods. Thus, described herein are components, arrays and methods using specific organ systems represented by in vitro models, including, but not limited to, for example, a cardiac analog using patterned cardiac myocytes. The invention is not limited to the particular analogs described herein but contemplates organ or tissue analogs found in human, animal, plant or insect bodies. Particular examples are not to be seen as limitations of the invention.

Incorporation of a functional cardiac system in component enables the discovery of complex, unknown and unexpected effects of active agents, such as toxicants. Reverse use dependence, variability in QT intervals and relative refractory period (which is related to triangulation) are measured in an in vitro system based on patterned cardiac myocytes. The in vitro electrophysiological measurement parameters are analogous to the parameters used in the SCREENIT scoring system introduced by Hondeghem and coworkers in 1994. In that model, variability in action potential (AP) duration, triangulation of the repolarization phase of the AP and reverse use dependence is measured on female rabbit Langendorff-perfused hearts. This in vitro system does not reproduce the whole complexity of the heart but shows that the measured parameters are able to measure the most important arrhythmogenic mechanisms including rhythm generation (chronotropy, firing frequency dispersion), conduction (conduction velocity, conduction velocity dispersion, frequency dependence of conduction velocity) and re-entry (QT interval, QT interval dispersion, reverse use dependence, absolute and relative refractory period). These parameters have high predictive value for cardiac side effects. In addition, by utilizing a scrum-free, defined culture medium, as disclosed herein, one of the major unknown variables in the system would be removed.

The present invention comprises cells, including but not limited to, animal, human plant or insect cells, and provides data that can reduce dependency on animals for testing and provides insights that cannot be obtained from whole animals. The present invention can lead to a more accurate and cost-effective assessment of the toxicological potential of environment chemicals or chemical mixtures. Aspects of the present invention combine both "cell culture analogs" (CCA) with the development of functional tissue mimics. These approaches are combined to make a realistic in vitro model of a mammal and predict its response from exposure to a chemical or chemical mixture, referred to herein as an active agent, whether particularly active on a cell or not. The present invention may comprise systems for functional muscle as well as neuronal systems. The present invention may comprise use of human stem cells for more authentic constructs leading to a human based components, systems and methods.

The present invention comprises a physical representation of a physiological based pharmacokinetic (PBPK) model. A PBPK model is a mathematical representation of the body, which treats the body as a set of interconnected compartments, each of which describes an organ or tissue. Each compartment is modeled as a chemical reactor, absorber, or surge tank. A set of reactive mass balances on parental compounds and metabolites are written for each compartment. Blood flow in and out of each compartment is simulated to match measured values. The model predicts the time dependent changes in the plasma and tissue compartment concentrations of parental compounds and metabolites. A person of skill would know that these mathematical models have been used in numerous studies on the toxicology of environmental chemicals.

While such computational models have proven to be useful aids in studies of absorption, distribution, metabolism, elimination, and toxicity (ADMET), they are limited. All relevant reactions and physiological responses are identified, particularly molecular mechanisms underlying cell response. For complex systems, such as mammals, it is difficult to capture not only the primary reactions but also all of the secondary responses (e.g., the metabolite of A, made in the liver, circulates to another tissue causing the release of B which then causes other cells to change physiologically). The disclosed components, arrays and methods compensate for this lack of complete knowledge.

In addition to the limitations of current in vitro tests to predict systemic effects, most assays are based on single cell analysis. It is well known that single cells are limited in their ability to mimic in vivo tissue function. Recently, functional cellular models, or multi-cellular systems that allow evaluation of properties previously only possible in intact animals or organs such as muscle dynamics [Wilson 2010], cardiac pacemaking [Natarajan 2011], neuronal function [Varghese 2010] and neuromuscular junction (NMJ) function [Guo 2010], have been developed to overcome these limitations but have not as yet been integrated. The disclosed components, arrays and methods provide a combination of these functional in vitro systems into a system that more accurately recapitulates the human response.

Components, systems and methods of the present invention comprise physical replicas of a PBPK model with multiple types of mammalian cells cultured in a component instead of a mathematical description of the metabolism or absorption. Thus, the physiology of the cells compensates for lack of prior or incomplete knowledge. In an aspect, the fluid fraction feeding each component functions as the blood fraction received by the corresponding organ in vivo. Fluid is re-circulated just as in the body. Also, the fluid residence time, which describes the duration of cell-compound contact, in each component equals its in vivo value. For well-mixed systems, this residence time controls the amount of reaction. The liquid to cell ratio in each cell culture unit is managed to be as close as possible to its physiological value. Shear stress introduced by the flow is calculated and is kept at the physiological value for that type of tissue. Shuler described and constructed the first CCA and demonstrated its potential usefulness with naphthalene as a model toxicant in 1995. The initial device and several subsequent studies used bench scale systems. In later studies, the CCA's were constructed as microfabricated devices.

An advantage of the components, arrays (systems) and methods of the present invention is that they are relatively inexpensive to make and can support high throughput studies. Further, the natural length scale (10 to 100 µm) is consistent with physiological length scales. Unlike other in vitro systems, such as multi-well plates, the disclosed components, systems and methods provide realistic dose dynamics (similar to what occurs in an animal or human) and allow for the formation and exchange of metabolites between compartments as well as exchange of compounds induced by the presence of the parental compound or metabolites. Coupling of the PBPK to the CCA and then to functional systems, as do the components, arrays (systems) and methods of the present invention is straightforward and can be used to test underlying molecular mechanisms.

Shuler has demonstrated the µCCA concept with naphthalene (Sin 2004; Viravaidya 2004], showing that naphthaquinone (rather than naphthalene epoxide) was the reactive metabolite generated in the liver causing gluthathione depletion and loss of viability in the lung compartment. Subsequent studies examined the response to drug combinations. While animal studies are expensive with a single compound, such studies become even more difficult when chemical mixtures are to be tested. The combinations and permutations become large when several compounds are tested, particularly when each compound can involve multiple doses and when the order of exposure may be important. For example, the use of doxorubicin was tested with two multidrug resistant (MDR) suppressing compounds (cyclosporine and nicardipine) for the treatment of MDR cancer [Tatosian 2009]; the action of the two MDR suppressors was found to be synergistic in the µCCA, but this was not observable in multi-well plate assays. The use of Tegafur (a pro-drug for 5-flurouracil (5-FU)) and uracil combination treatment was examined for colon cancer using both a PK-PD model and a µCCA [Sung 2009]. As observed in animal trials, the µCCA predicted that a uracil to Tegafur ratio of 4 to 1 was optimal in maximizing the concentration of 5-FU in the tumor relative to that in the blood. Unlike multi-well plates, the system indicated that 5-FU must be produced in the liver and circulate to the tumor to kill cells and that uracil (which inhibits the enzyme dihydroprymidinedehydrogenase) enhances the toxicity of Tegafur.

Technical enhancements to the µCCA system such as bubble traps, use of human reporter cell lines, and techniques to image the system in near real time have been made. A further enhancement involves connecting this model of systemic circulation with a model of a barrier tissue that controls entry into the body. Models of the gastrointestinal (GI) tract to model response to oral absorption of chemicals and drugs have also been constructed.

These initial CCA studies have been done primarily with cell lines either as monolayers or embedded in hydrogels. Such unorganized cell systems often lack key enzymes at realistic levels, and the biological functionality of the tissue is not well represented. Further measurements have been based solely on optically accessible end points such as fluorescence (e.g., dye reaction with gluthathione, uptake of naturally fluorescent compounds, viability stains, or reporter proteins, such as GFP). The addition of biologically functional tissues, such as patterned cardiac myocytes integrated with Microelectrode Arrays (MEAs), increases the information control and allows for the use of electrical measurements to monitor response.

An aspect of the components, arrays and methods of the present invention comprises using monitoring methods, which are 1) non-invasive, 2) more high throughput, 3) high information content, 4) functional, 5) able to detect known and unknown effects of active agents at physiological concentrations, 6) appropriate for continuous monitoring, 7) compatible with fluidic systems, and 8) mechanically robust. Hybrid (live-cell/electronic) systems have been developed to overcome several shortcomings of traditional whole-cell biosensors, at the same time preserving their advantageous properties over traditional physico-chemical or biochemical sensing methods.

Figure 2B:
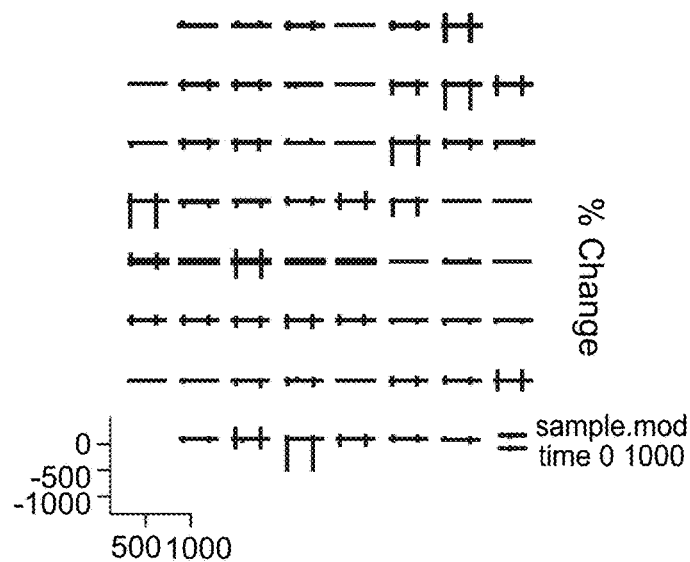
Figure 2C:
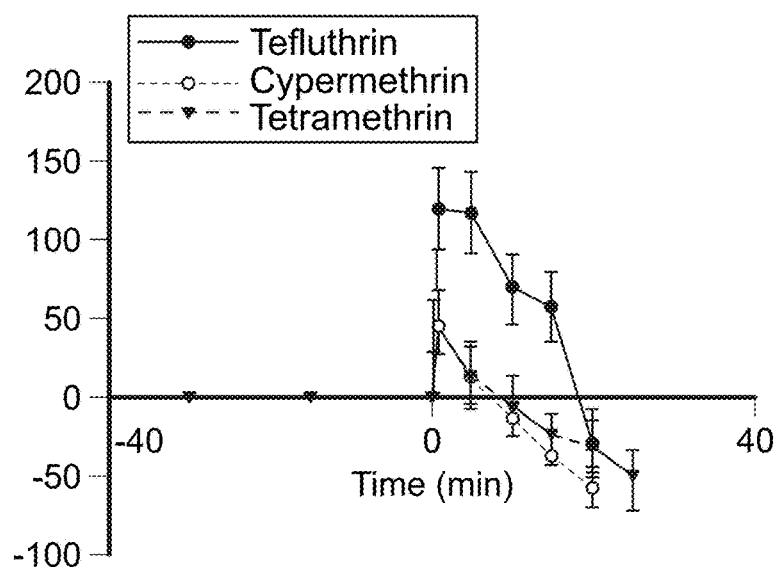

An aspect of the present invention comprises a method which utilizes a cellular construct comprising cardiac myocytes, surface embedded microelectrodes and patterned substrates on the microelectrode array to monitor the condition of the cardiac chamber in a device of the present invention in real time. Cultured cardiac myocytes are widely used in toxin detection and in drug development to screen for unwanted cardiac side effects [Meyer 2004]. It has been shown that pyrethroids [Natarajan 2006] and heavy metals can be detected, and in some extent classified, based on their physiological effects on the spontaneous activity of cultured cardiac myocytes measured using a non-invasive, high-throughput, chronic protocol with substrate-embedded MEAs (FIG. 2).

By using an appropriate double-stimulation protocol and 'collide' action potentials at the intersection of line patterns with variable delay, the measurement of action potential length, the absolute and relative refractory period as well as measurement of the effects of 1-Heptanol were achieved (FIG. 3). This functional assay, combined with components, arrays and method of the present invention, allows for the observation of systemic effects of compounds on parameters that are normally used in vivo to monitor human health. This is a major advance for increasing the relevance of in vitro systems to predict effects on a mammal's response to active agents, such as toxins. This patterned cardiac system has also been shown to be responsive to sparfloxacin, an antibiotic known to cause fibrillation as recently shown.

An aspect of the present invention comprises components, systems and methods comprising a "liver" analog region to mimic metabolism, a patterned cardiac myocyte/MEA functional reporter region, and an "other tissues" region, which is a compartment without any cells that represents the holdup of recirculating fluid in tissues where there is no adsorption or metabolism. For example, the present invention allows for the validation of the integrated cardiac myocyte reporter region and the functional effects of stereoisomers of permethrin (a pyrethroid which is an environmental toxin) on the tissues in the system can be measured. Permethrin has four stereospecific isomers: 1R-cis-, 1R-trans-, 1S-cis-, and 1 S-trans-. The 1R-cis- and 1R-trans- isomers are active, whereas the other two are not. Moreover, the cis isomers are about ten times more toxic than the trans isomers in vivo. Recent data indicated that the metabolic rate of cis-permethrin is much slower than that of the trans isoform, which could be an explanation for the different in vivo toxicity.

An aspect of the present invention comprises components, systems and methods that can be used to determine and measure the effect of different enantiomers, for example permethrin, on spontaneous beating and conduction velocity of patterned cardiac myocytes in the presence and absence of one or more chambers of a component representing the major metabolic pathways in the body. The lifetime of components can be extended to examine the effects of a compound in chronic studies.

The present invention comprises components, arrays and methods comprising patterned biologically functional cardiac myocytes on microelectrode arrays and other chambers comprising cells, structures, factors, co-factors or other elements for constructing analogs of organ tissues or systems that mimic physiological, physical, chemical, and/or electrical conditions of whole organisms.

The present invention comprises methods for determining the effect of an input variable on components, arrays and methods, comprising contacting cells comprised by one or more components with an input variable and monitoring at least one output parameter. For example, components, arrays and methods may comprise testing of active agents for beneficial or deleterious effects, long-term studies of exposure to active agents, determination of active metabolites or other studies designed by those skilled in the art using the components, arrays and methods of the present invention.

An aspect of the present invention comprises components and/or systems comprising a housing for enclosing a component and/or systems disclosed herein, at least one component, wherein a component may be a microscale chamber having a geometry that simulates an in vivo interaction with culture medium, wherein the chamber comprises a first inlet and a first outlet for flow of the culture medium, and channels coupled to the inlets and outlets of the chamber. A component or system may be held in place or immobilized by attachment to or association with a board, a planar solid, to which the one or more components of a system are attached or associated.

An aspect of the present invention comprises cell culture analog systems comprising one or a plurality of components, wherein a component comprises a cardiac component, a neural component, a gastrointestinal component, a kidney-like component, an other tissues component or a hepatic component. A cell culture analog system comprises a cell culture analog system comprising cardiac component and a hepatic component. A system comprises a cell culture analog system comprising a plurality of components comprising a cardiac component, a neural component and a hepatic component. A cell culture analog system comprises a cell culture analog system comprising a plurality of components comprising a cardiac component, a neural component, a gastrointestinal component, and a hepatic component. A cell culture analog system comprises a cell culture analog system comprising a plurality of components comprising a cardiac component, a neural component, a gastrointestinal component, a kidney-like component, and a hepatic component. A cell culture analog system comprises a cell culture analog system comprising a plurality of components comprising a cardiac component, a neural component, a gastrointestinal component, a kidney-like component, an other tissues component, a neuromuscular component, a muscular component and a hepatic component. A cell culture analog system comprises a cell culture analog system comprising a plurality of components comprising a cardiac component, a neural component, a gastrointestinal component, a kidney-like component, an other tissues component, a neuromuscular component, a muscle component and a hepatic component. A cell culture analog system comprises a cell culture analog system comprising a plurality of components comprising a neural component, a gastrointestinal component, a kidney-like component, an other tissues component and a hepatic component. A cell culture analog system comprises a cell culture analog system comprising a plurality of components comprising a gastrointestinal component, a kidney-like component, an other tissues component and a hepatic component. A cell culture analog system comprises a cell culture analog system comprising a plurality of components comprising an other tissues component and a hepatic component. A cell culture analog system comprises a cell culture analog system comprising a plurality of components comprising a cardiac component, a gastrointestinal component, a kidney-like component, an other tissues component and a hepatic component. A cell culture analog system comprises a cell culture analog system comprising a plurality of components comprising a cardiac component, a kidney-like component, an other tissues component and a hepatic component. A cell culture analog system comprises a cell culture analog system comprising a plurality of components comprising a cardiac component, an other tissues component and a hepatic component. A cell culture analog system comprises a cell culture analog system comprising a plurality of components comprising a cardiac component, and a gastrointestinal component. A cell culture analog system comprises a cell culture analog system comprising a plurality of components comprising a cardiac component, and a kidney-like component. A cell culture analog system comprises a cell culture analog system comprising a plurality of components comprising a cardiac component, a neuromuscular component, a muscle component and a hepatic component. An aspect of the present invention comprises a cell culture analog system comprising one component, two components, three components, four components, five components, six components, seven components, eight components, or more than eight components.

The present invention comprises methods, systems and means for dynamically controlling a cell culture analog system, for example, comprising a computer and other elements, such as processors, sensors, actuators, etc., wherein, in an aspect, a method comprises analyzing data from a plurality of sensors to measure physiological events in one or more chambers of one or more components disclosed herein; optionally, regulating a cell culture characteristic such as temperature, light, oxygen, carbon dioxide, and/or fluid flow rates of a culture medium in at least one chamber of a component; and detecting biological or toxicological reactions in the cells or other elements of one or more chambers of a component; and optionally, upon detection, recording the change and/or changing one or more pharmacokinetic parameters of a component.

The present invention comprises a computer-readable medium having computer-executable instructions stored thereon to perform a method. For example, a method may comprise analyzing data from a plurality of sensors to measure physiological events in one or more chambers of one or more components disclosed herein; optionally, regulating a characteristic such as temperature, light, oxygen, carbon dioxide, and/or fluid flow rates of a culture medium in at least one chamber of a component; and detecting biological or toxicological reactions in the cells or other elements of one or more chambers of a component; and optionally, upon detection, recording the change and/or changing one or more pharmacokinetic parameters of component.

An aspect of a cell culture analog system comprises the arrangement of the components in a system. A component may be in fluid connection with one or more components or conduits for fluid connection. A component may be a defined area in a solid material, such as a chamber formed by removal of a portion of the solid material to form an indentation or well in the solid material, such as the wells connected by fluid connections or channels formed in a solid material. See FIG. 18A for an example of wells configured to be in fluid connection via channels connecting the wells. In an aspect, gravity can move fluid from component to component.

An aspect of a system of the present invention may comprise placing one or more components or portions of components on a platform that is capable of movement. In an aspect, a movable platform can allow gravity to affect or to drive fluid flow. For example, the component may be tilted. A method of the present invention may comprise tilting or moving a component from a position substantially parallel to a particular reference location, such as the earth's surface, or to a position at an angle to the particular reference location, such as the earth's surface. The tilting motion may be a one time, intermittently or constantly occurring for the component and/or system. A system or component of the present invention may comprise a movable stage that moves a cell culture analog system or component from a first position relative to a reference point to at least one different position, and may or may not return the system or component to the first position. For example, a system, component or method comprising a system and/or component may comprise a moveable platform on which a system or component is placed such that the system and/or component may be moved from a first position to at least one different position if movement is desired. A portion of a system or component may be configured to be moveable such that the portion may be moved from a first position to at least one different position if movement is desired. As used herein, tilting means moving a system or component of a system or a portion of a system or a component from a first position in three dimensional space to at least one different position in three dimensional space. A tilting action may include, but is not limited to, a one-time tilt wherein the system or component moves from one position to a second position; or may include tilting in a continuous or intermittent pattern between one or more positions other than the first position. Tilting may occur in a smooth, non-liner function. Tilting may be in a step function, for example, the system, component or portion thereof, may be moved from a first position to a one or more other positions, such as a tilt to a 10° position from the first position, pause at the second position, tilt to a 20° position from the first position, pause at the third position, tilt to a 30° position, pause at the fourth position, return tilt to a 20° position from the first position, pause at the third position, return tilt to a 10° position from the first position, pause at the second position, return to the first position, and optionally, repeat one or more times. Tilting may be in a single step function. For example, move the system or component quickly to +30° from the starting position, pause, move quickly to −30°, pause, back to +30°, and optionally, repeat one or more times.

An aspect of movement of a system or component or portion thereof comprises the time the system, component or portion thereof remains in one or more positions. Such time may be brief or long, from seconds to minutes to days to weeks, and may be determined by one of skill in the art, or may be used to mix compositions comprising media, cellular factors, cells, compounds to be tested, or other ingredients in a component or between components in a system. The period of movement of the system may be brief or long-term, and may be for seconds, minutes days or weeks, and may occur continuously from the start-up of a system or component to completion, or for one or more times during the use of the system or component, or may occur intermittently or randomly during the use of the system or component.

The movement of a system, component or portion thereof, may be uniform or non-uniform in any aspect, such as in time at a position, in time between movements, speed of the movement from one position to another, degree of tilt from the horizontal axis, number of cycles of movement from one position to one or more other positions, and combinations of these aspects. The amount and type of movement of a system, component or position thereof may be determined by keeping the flow rate constant to and between one or more components, a need to produce time-dependent flow rates or time dependent shear stresses, and/or to produce flow and movement to and between one or more components to mimic blood flow and conditions found in fluid dynamics in a living organism.

Figure 18A:
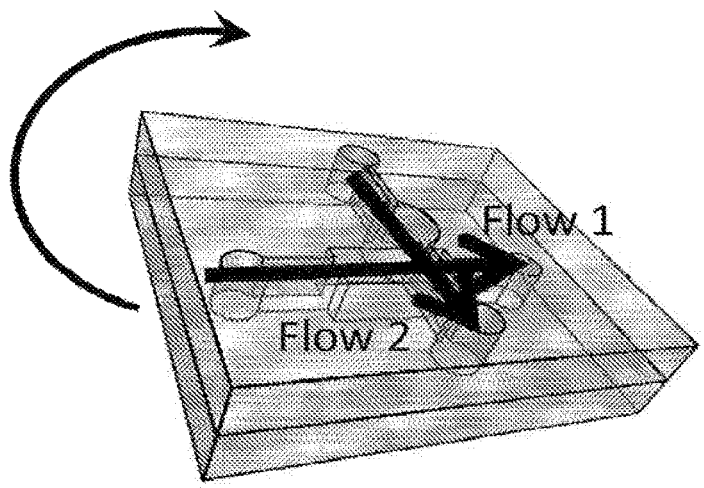
FIGS. 18A-18C show mixing of compositions in components that may be controlled by smooth, non-linear tilting of the component or a portion of a component.
Figure 18B:
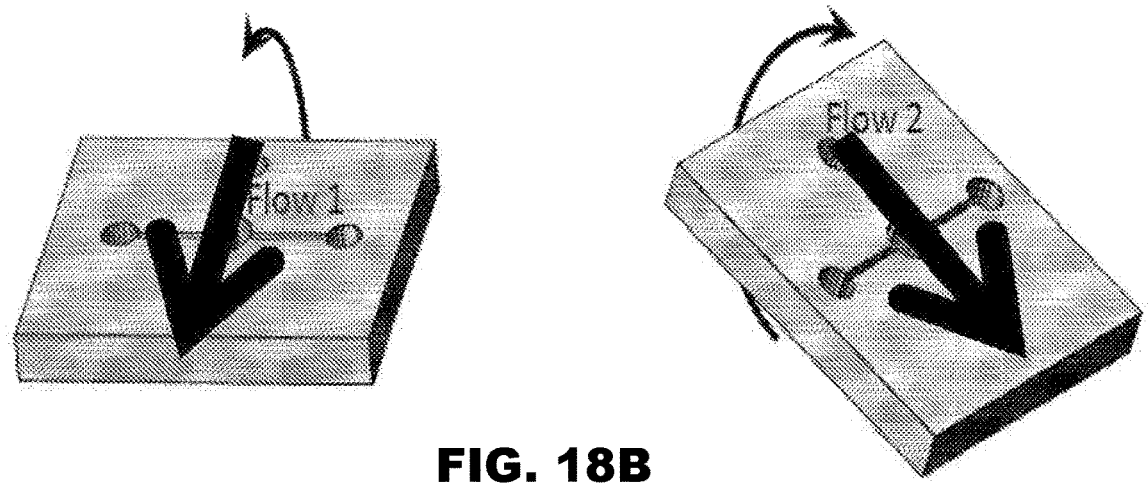

As shown in FIG. 18A, the design of the tilt direction and the flow paths may be used to produce two or more separate flows of liquid compositions in and/or between one or more components. By controlling the orientation of the component in three dimensional space, there may be, for example, two separate flows of liquid in separate components, or intersecting flows between components. As shown in FIG. 18A, a system can comprise two components, wherein the components are in fluid connection with a media well, respectively, through fluid channels. Fluid in a media well can be moved from one media well to a different media well, the media flow Flow 2 traverses a component, and may or may not be mixed with the media from Flow 1. By determining the orientation of the component in three dimensional space, the ratios of mixed fluids may be controlled, for example the ratio of the amount of flow 1 mixed with flow 2 may be controlled by the axis of tilt of the flow paths.

Figure 18C:
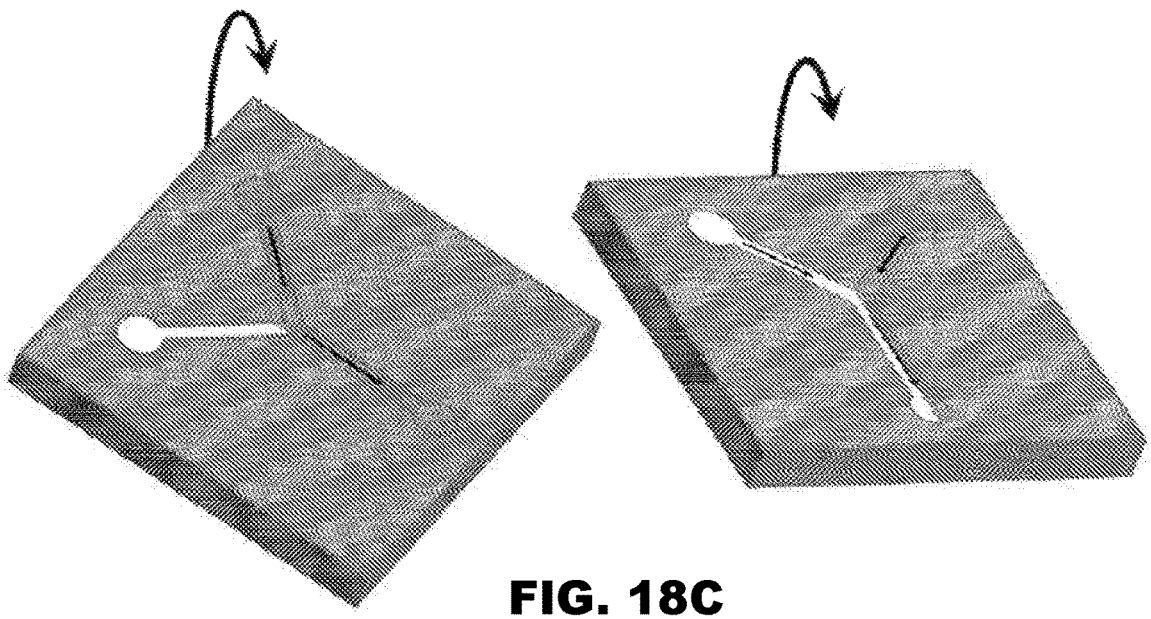

In FIGS. 18B1 and 18B2, and 18C1 and 18C2, only the fluid flow paths are shown, and components are not shown. In 18B1, with a particular tilt or orientation of a system or components (not shown), fluid will flow from well to well and not to the other wells. A mixing well may be located between one or more wells. In 18B2, in a different tilt or orientation of a system or component, fluid flows from media well to media well. Other aspects of moving fluids or mixing fluids are shown in FIGS. 18C1 and 18C2. In FIG. 18C1, fluids move but are not mixed, and in FIG. 18C2, two fluids flow and are mixed.

Figure 19A:
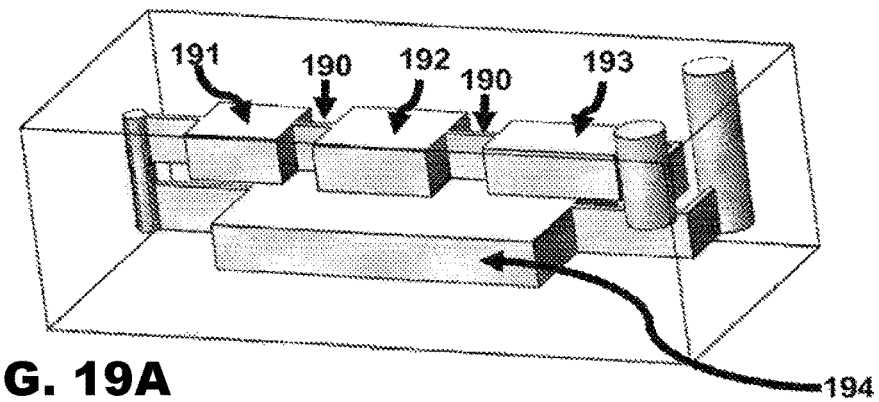
FIGS. 19A-19D show exemplary embodiments for cell culture analog systems of the present invention.
Figure 19B:
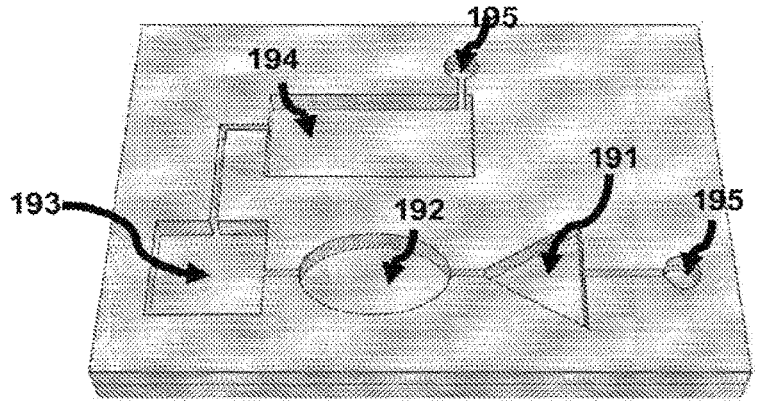
Figure 19C:
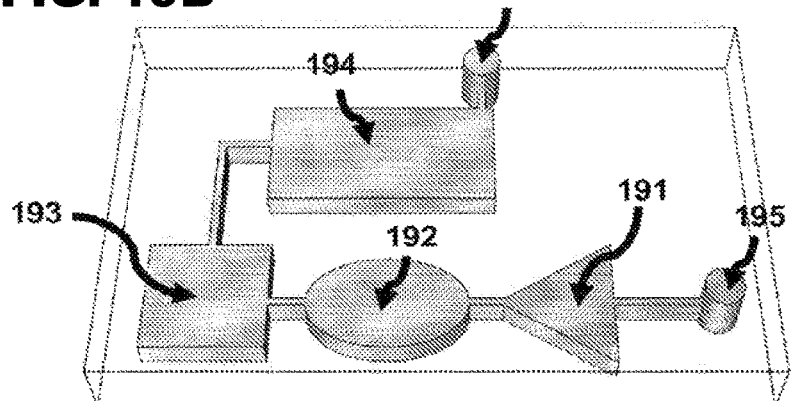
Figure 19D:
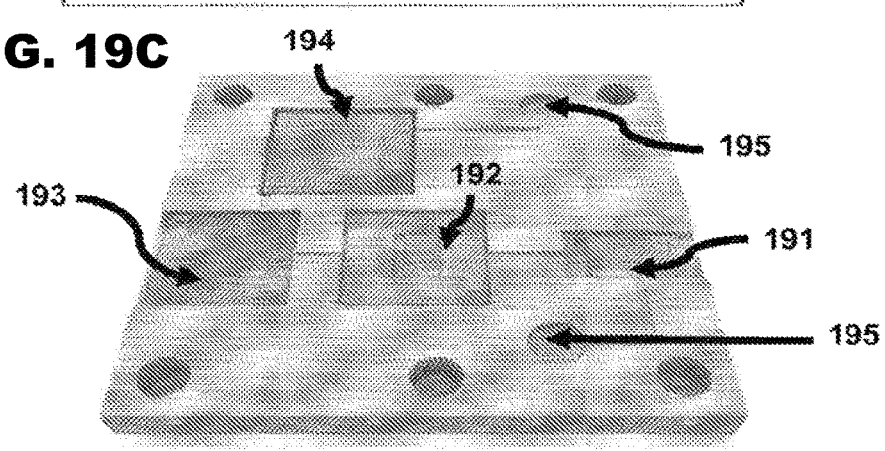

FIG. 19A shows an arrangement of components wherein the components are in fluid connection with one or more components. For example, component 191 is in fluid connection with component 192 through connection 190, and with component 194. Component 192 is in fluid connection with component 191 through connection 190, with component 193 through connection 190, and component 194. Component 193 is in fluid connection with component 192 through connection 190, and with component 194. Components in a system may be positioned in any physical relationship that is functional for the operation of the system. In FIG. 19B, a system is in a planar sequential arrangement wherein one component is in fluid connection with the adjacent component(s) or a well 193. Components 191-194 are shown in fluid connection by connection 190. The components may be formed in a solid material and individual elements may be added to the indented space(s) in the solid material. See FIG. 19B. The components may be assembled in a planar relationship to one another, see FIG. 19C. A solid planar material may be used to immobilize one or more components, and fluid connections may be channels formed in the solid material to fluidly connect the components. See FIG. 19D where individual components 191, 192, 195, and 194 are placed within shaped wells to hold the components in place and connections 190 fluidly connect wells 193, for example, for containing media, to components arranged in a serial relationship. The present invention comprises parallel arrangements of components.

The present invention comprises in vitro methods and systems for mimicking the in vivo metabolism and response to stimuli of tissues, organs, organ systems of living organisms. A method of the present invention determining the effect of an input variable on a simulated multi-organ system, comprising contacting at least one cell in a cell culture analog system which comprises a plurality of components, wherein a component comprises one or more chambers, chips or regions, and optionally, one or more types of cells; and one or more sensing elements, wherein one or more of the plurality of components is in fluid connection with another component, with an input variable and recording at least one output parameter. The method may comprise measuring and recording more than one output parameter, or a plurality of output parameters from a plurality of components. A step of recording at least one output parameter comprises obtaining information from a sensing element in a component.

A system may comprise a plurality of components of which at least one component is a cardiac-simulating component comprising cardiac cells cultured on one or more microcantilevers. A cardiac-simulating component may comprise cardiac cells cultured in a pattern on a microelectrode array with embedded microelectrodes. A system may comprise a plurality of components of which at least one component is a motoneuron component comprising neurons and myotubes forming neuromuscular junctions cultured on microcantilevers. A motoneuron component may comprise neurons and myotubes forming neuromuscular junctions cultured in a pattern on a microelectrode array with embedded microelectrodes. A system may comprise a plurality of components of which at least two component is a cardiac-simulating component and a motoneuron component. A component may comprise a tissue biopsy, such as ex plant tissue from a body, for example a dissected portion of a tissue or organ.

A cell culture analog system may further comprise connection elements, pumps, filters, sensors, alarms, and computer control elements. One or more components may be a microfluidic device. The cells may be derived from a human, an animal, a plant or an insect, or combinations and mixtures thereof. The cell culture analog system may further comprise serum-free culture medium.

A cell culture analog system may comprise at least a first component comprising a microscale chamber containing a first type of cell under conditions where the first type of cell provides at least one pharmacokinetic parameter value comparable to a value obtained for the same type of cell in vivo, wherein the first chamber comprises a first inlet and a first outlet for flow of culture medium; and comprises, a second component comprising a microscale chamber containing a second type of cell under conditions where the second type of cell provides at least one pharmacokinetic parameter value comparable to a value obtained for the same type of cell in vivo, wherein the second chamber comprises a second inlet and a second outlet for flow of culture medium; and a microfluidic channel interconnecting the first and second chambers. At least one component may comprise a first chamber comprising a first cell type maintained under conditions providing at least one pharmacokinetic parameter value comparable to values obtained for the cells in vivo; a second component comprises a second chamber of the same or different geometry than the first chamber comprising a second cell type maintained under conditions providing at least one pharmacokinetic parameter value comparable to values obtained for the cells in vivo; wherein the first and second chambers are interconnected by fluidic channels; and an inlet and outlet for re-circulation of culture medium.

In a method for testing the response(s) of a cell culture analog system to an input variable, an input variable may be an organic or inorganic chemical compound. An input variable may be more than one compound, and may be a mixture of inorganic and organic compounds. An input variable be may a pharmaceutical composition, an environmental sample, a nutritional sample, or a consumer product. An input variable may be a virus, liposome, nanoparticle, biodegradable polymer, radiolabeled particle or toxin, biomolecule, toxin-conjugated particle or biomolecule. The time period for testing the reaction of one or a plurality of components in a cell culture analog system may be for 72 hours, 84 hours, 96 hours, 108 hours, 120 hours, 132 hours, 144 hours, 156 hours, 168 hours, 180 hours, or for days or weeks, or longer, or any amount of time in between.

A cell culture analog system of the present invention may comprise a plurality of components, wherein a component comprises one or more chambers, chips or regions, and one or more types of cells; and one or more sensing elements, wherein one or more of the plurality of components is in fluid connection with another component. The system may further comprise connection elements, pumps, filters, sensors, alarms, and computer control elements. A component of the system may be a microfluidic device. The cells of the components of the system may be derived from a human, an animal, a plant or an insect, or combinations and mixtures thereof. At least one component may comprise a chip comprising biological cells on a microelectrode array comprising surface embedded microelectrodes. A cell culture analog system comprises at least one serum-free fluid culture medium.

A cell culture analog system may comprise at least one component comprising at least a first microscale chamber containing a first type of cell under conditions where the first type of cell provides at least one pharmacokinetic parameter value comparable to a value obtained for the same type of cell in vivo, wherein the first chamber comprises a first inlet and a first outlet for flow of culture medium; and optionally comprises, a second component comprising a second microscale chamber containing a second type of cell under conditions where the second type of cell provides at least one pharmacokinetic parameter value comparable to a value obtained for the same type of cell in vivo, wherein the second chamber comprises a second inlet and a second outlet for flow of culture medium; and a microfluidic channel interconnecting the first and second chambers. A cell culture analog system may comprise at least one component comprising a first chamber comprising a first cell type maintained under conditions providing at least one pharmacokinetic parameter value comparable to values obtained for the cells in vivo; and a second component comprising a second chamber of the same or different geometry than the first chamber comprising a second cell type maintained under conditions providing at least one pharmacokinetic parameter value comparable to values obtained for the cells in vivo; wherein the first and second chambers are interconnected by fluidic channels; and an inlet and outlet for re-circulation of culture medium. A cell culture analog system may comprise one or more additional microscale chambers containing the same or different types of cells as in the first or optionally second chambers, under conditions where the additional cell provides at least one pharmacokinetic parameter value comparable to a value obtained for the same type of cell in vivo, wherein the one or more additional chambers comprise an inlet and outlet for flow of culture medium. A cell culture analog system may operate for 72 hours, 84 hours, 96 hours, 108 hours, 120 hours, 132 hours, 144 hours, 156 hours, 168 hours, 180 hours, or for days or weeks, or longer, or any amount of time in between.

A cell analog system may use one or more culture media. For example, the entire system may use one culture media, such as a serum-free media, and that media may be circulated to one or more of the components in fluid connection in the system. Individual media components, such as nutritional compounds or growth cell factors may be added in individual components, and may or may not be circulated to other components of the system. The cells in a component may be grown and develop to the desired stage or number of cells in a component using a particular culture media and then that component may be joined into a cell analog system in which a different culture media, such as a serum-free media, is circulated throughout the entire system. A cell analog system of the present invention may comprise use of one culture media in each connected component. A cell analog system of the present invention may comprise use of more than one culture media, at different times during the operation of the system, or in different individual components.

It is to be understood that this invention is not limited to particular methods, and as such may, of course, vary. It is also to be understood that the terminology used herein is for the purpose of describing particular embodiments only and is not intended to be limiting.

All patents, patent applications, and other referenced articles, journals or references referred to herein are each hereby expressly incorporated in its entirety.

As used in the specification and the appended claims, the singular forms "a," "an" and "the" include plural referents unless the context clearly dictates otherwise. The term "or" refers to a single element of stated alternative elements or a combination of two or more elements, unless the context clearly indicates otherwise. As used herein, "comprises" means "includes." Thus, "comprising A or B," means "including A, B, or A and B," without excluding additional elements.

Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not. For example, the phrase "optionally obtained prior to treatment" means obtained before treatment, after treatment, or not at all.

As used throughout, by "subject" is meant an individual. Preferably, the subject is a mammal such as a primate, and, more preferably, a human. Non-human primates include marmosets, monkeys, chimpanzees, gorillas, orangutans, and gibbons, to name a few. The term "subject" includes domesticated animals, such as cats, dogs, etc., livestock (for example, cattle, horses, pigs, sheep, goats, etc.), laboratory animals (for example, ferret, chinchilla, mouse, rabbit, rat, gerbil, guinea pig, etc.) and avian species (for example, chickens, turkeys, ducks, pheasants, pigeons, doves, parrots, cockatoos, geese, etc.). The subjects of the present invention can also include, but are not limited to fish (for example, zebrafish, goldfish, tilapia, salmon and trout), amphibians and reptiles.

Throughout this application, various publications and patent applications are referenced. The disclosures of these publications in their entireties are hereby incorporated by reference into this application in order to more fully describe the state of the art to which this invention pertains.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

Each of the following patent applications is herein incorporated by reference in its entirety: (1) U.S. patent application Ser. No. 12/661,323 filed on Mar. 15, 2000 and titled "Bio-Microelectromechanical System Transducer and Associated Methods", (2) U.S. patent application Ser. No. 12/765,399 filed on Apr. 22, 2010 and titled "Method for Culturing Skeletal Muscle for Tissue Engineering", (3) U.S. patent application Ser. No. 12/938,701 filed Nov. 3, 2010 and titled "Patterned Cardiomyocyte Culture on Microelectrode Array", (4) U.S. patent application Ser. No. 13/102,672 filed on May 6, 2011 and titled "Formation of Neuromuscular Junctions in a Defined System", (5) U.S. patent application Ser. No. 12/145,810 filed Jun. 25, 2008 and titled "Cell Culture Media and Process for Differentiation of Human Spinal Cord Stem Cells into Functional Motor Neuron Cells". (6) U.S. patent application Ser. No. 13/576, 442 filed Feb. 7, 2011 and titled "Model and Methods for Identifying Points of Action in Electrically Active Cells", (7) U.S. patent application Ser. No. 13/696,396 filed May 6, 2011 and titled "Formation of Neuromuscular Junctions", (8) U.S. patent application Ser. No. 12/117,339 filed May 8, 2008 and titled "Culture of Electrically Functional Adult Spinal Cord Neurons and Associated Methods", (9) U.S. patent application Ser. No. 12/788,732 filed May 27, 2010 and titled "Method of Myelinating Isolated Motoneurons", (10) U.S. patent application Ser. No. 12/765,996 filed Apr. 23, 2010 and titled "Long Term In vitro Culture of Tissue Engineered Functional Neuromuscular Junctions", (11) U.S. patent application Ser. No. 13/322,903 filed on May 28, 2010 and titled "In vitro Production of Oligodendrocytes from Human Umbilical Cord Stem Cells", and (12) U.S. patent application Ser. No. 13/322,911 filed May 27, 2010 and titled "Method of Screening Drugs for Reversal of Amyloid Beta Neurotoxicity", U.S. Provisional Patent Application Nos. 61/684,168, filed Aug. 17, 2012; 61/758,628, filed Jan. 30, 2013; 61/732,042, filed Nov. 30, 2012; U.S. Pat. No. 6,132,574, filed Dec. 3, 2012; and U.S. Provisional Patent Application Ser. No. 61/784,923, titled "Compositions and Methods for Generating Neural Crest Cells", an inventor James Hickman, filed Mar. 14, 2013; and applications concurrently filed herewith and each incorporated in its entirety, U.S. Provisional Patent Application Ser. No. 61/789,587 titled "Methods, Systems and Compositions for In vitro Concentric Cell Culture Analog Systems", filed Mar. 15, 2013, an inventor James Hickman; and U.S. Provisional Patent Application Ser. No. 61/790,061 titled "Devices and Systems for Whole Heart Function", filed Mar. 15, 2013, an inventor James Hickman.

EXAMPLES

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by mole, temperature is in C or is at ambient temperature, and pressure is at or near atmospheric.

Example 1

Integrating functionally active tissue constructs into a component and demonstrating its ability to respond appropriately to known toxins. A simple μCCA was fabricated with liver, cardiac, and "other tissues" compartments.

Figure 4B:
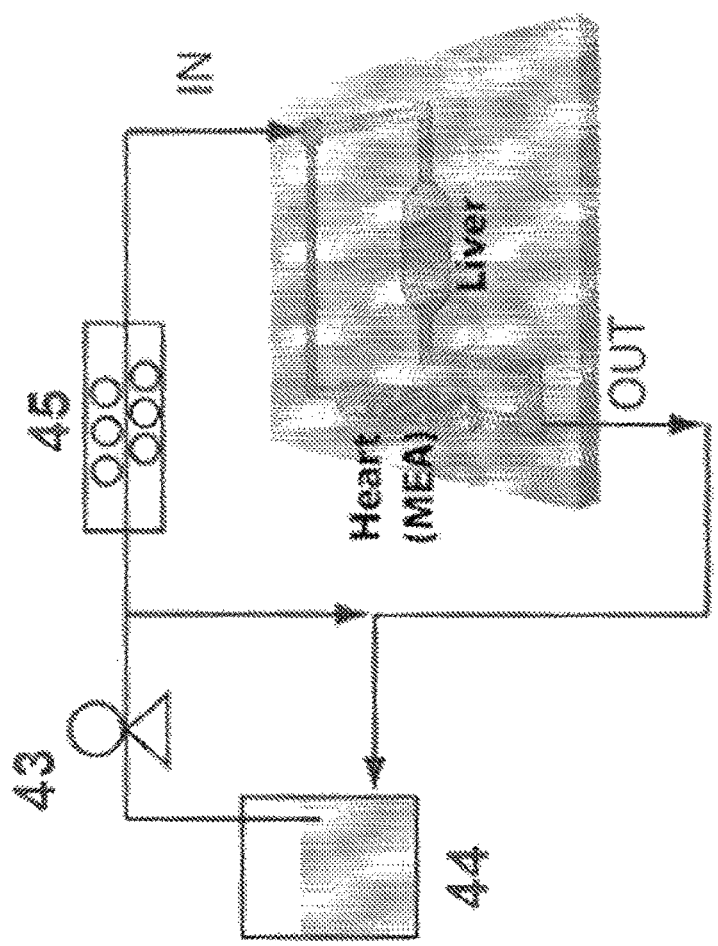
FIGS. 4A-4B show a diagram of a simple μCCA.
Figure 4A:
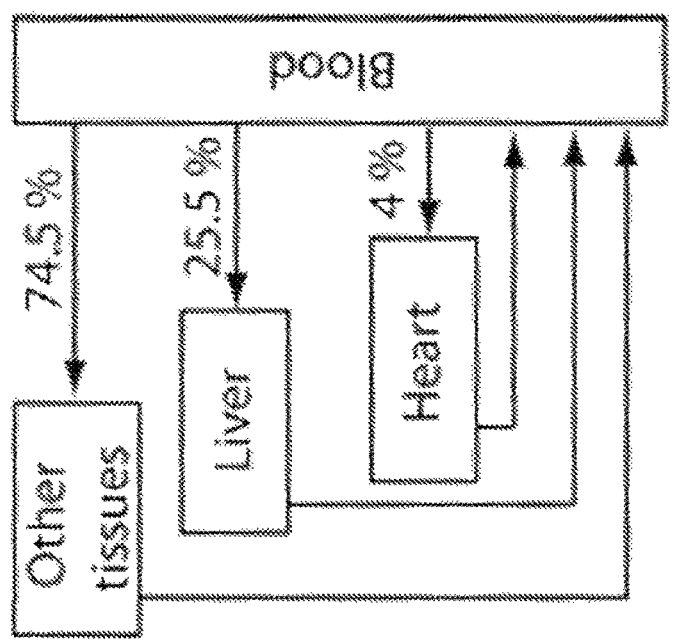

Techniques to fabricate a μCCA that mimics systemic circulation have been described in detail [Sin 2004] with modifications to increase realism [Tatosian 2009] and to use hydrogel entrapped 3-D cultures instead of monolayer cultures [Sung 2009]. The system was fabricated onto a silicon wafer to make identical chips that were 2.5 cm by 2.5 cm using standard photolithographic and deep reactive ion etching techniques at Cornell's Nanoscale Science & Technology Facility (CNF). The design was based on a simplified PBPK consisting of liver, cardiac, and other tissues compartments. Design criteria were based on relative mass of liver to cardiac tissue to the rest of the body. Fluid residence times in these tissues were estimated as 58 s in the heart, 63 s in the liver, and 630 s in "other tissues". FIG. 4 is a diagram of this simple μCCA and the pump (43), the other tissues compartment (44), and the bubble trap (45) are shown in FIG. 4B.

While all of the blood flows through the heart, only about 4% of the blood flow feeds the heart muscle. Also this diagram was simplified in combining many tissues (some well-perfused and others slowly perfused) into "other tissues" compartment. Redrawing the PBPK in this manner led to a change in dynamic response compared to that from a more complete model. In the case of doxorubicin [Tatosian 2009], the change in response to different PBPKs was quantitatively small and qualitatively very similar. Because the PBPK models are available for both configurations, it is possible to go back and forth between the two models. Basically the kinetic parameters for each cell type can be estimated with the data from the μCCA and the corresponding PBPK. Since flow rates and the number of cells are known and the time dependent concentrations of the parental compounds and metabolites can be measured and if absorption of chemicals to the device is measured and included, then one can estimate kinetic parameters assuming a reasonable rate form. Once the kinetic parameters are known, then the response in a PBPK corresponding to the true physiological case is known.

As in previous designs, the flow split was determined from a calculation of pressure drop and the size of the microchannels using the Hagen-Poiseuille equation. The chamber geometry was designed to insure that hydrodynamic fluid stress is less than 2 dynes/cm$^2$. The liver chamber was made 100 μm deep to accommodate a hydrogel containing liver cells (HepG2-C3A). The cardiac chamber required an extra fabrication step for creation of the multi-electrode arrays (MEAs) as detailed in FIGS. 5 and 6.

Patterning of PEG on MEAs: In brief, in the first step PEG self-assembled monolayers were formed on the commercial MEAs and on glass coverslip controls. The patterns were then created by laser ablation through a mask using a 193 nanometer eximer laser. The ablated areas were backfilled using fibronectin as in FIG. 5. Details of the procedures can be found in [Natarajan 2011] and [Wilson 2011]. Surface characterization serves as a quality control measure, and each step of the patterning process was verified by surface characterization; thus, the inter-device variability was controlled and minimized.

Figures 5A, 5B:
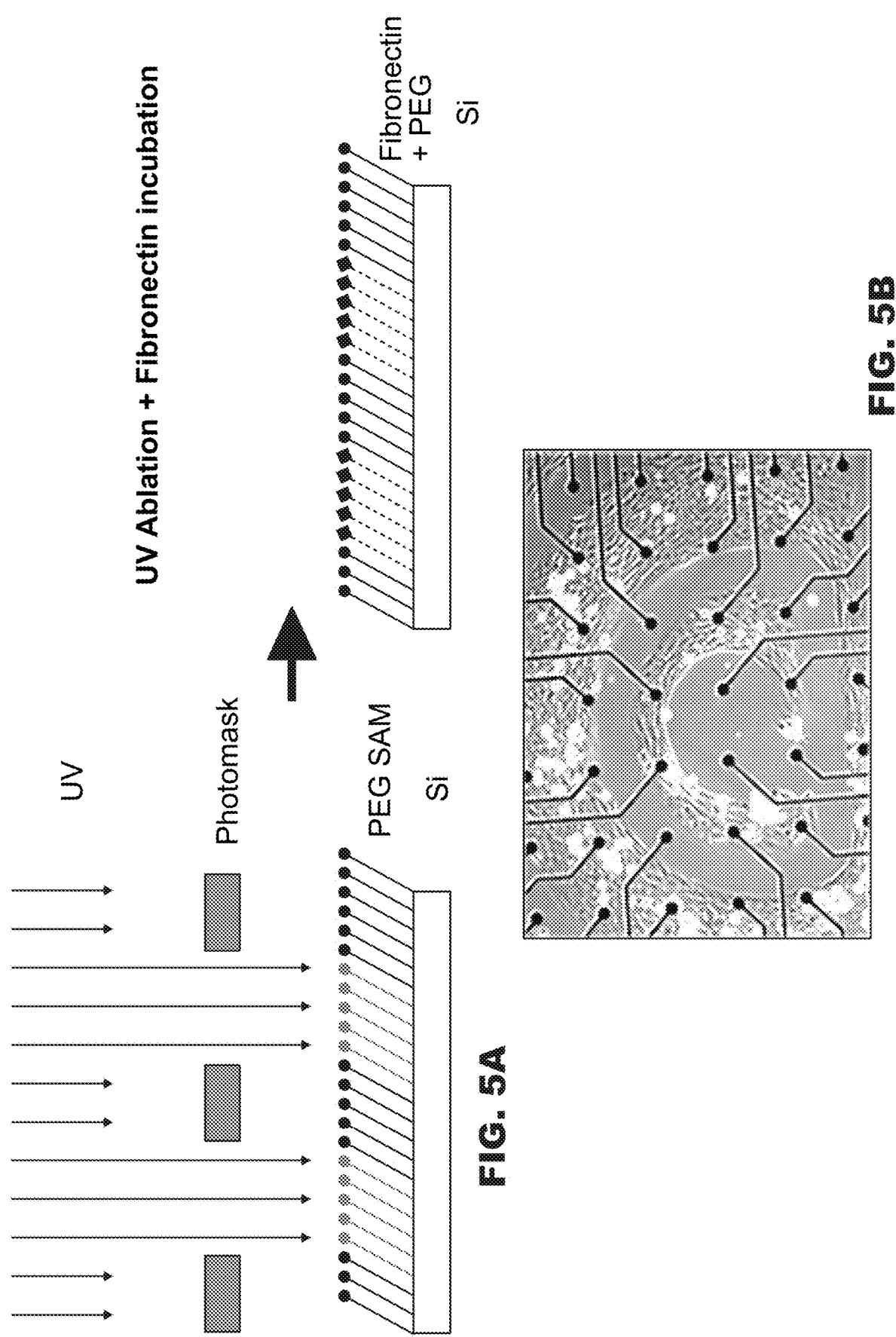
FIG. 5A shows photolithographic patterning of PEG self-assembled monolayers and consequent protein functionalization. PEG self-assembled monolayers are ablated by deep UV irradiation through a photomask. Incubation with fibronectin results in fibronectin adsorption to the ablated areas, whereas the PEG surface is resistant to protein adsorption.
FIG. 5B shows an example of cardiac pattern on MEA.
Figure 6B:
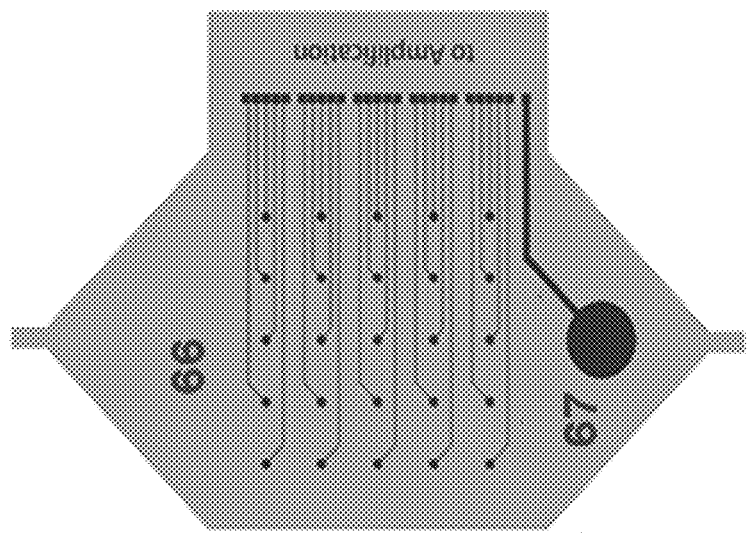
FIG. 6B shows a magnification of the cardiac chamber, the electrode array for recording 66 and one larger ground electrode 67. Electrodes are connected to an amplification head stage (Multichannel Systems, Germany) via contact pads at the right.
Figure 6A:
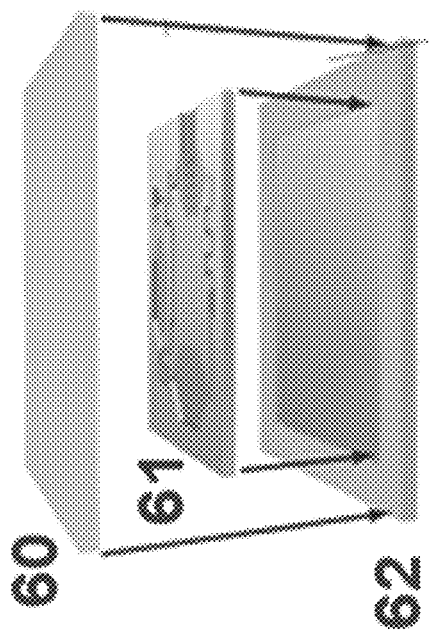
FIG. 6A shows a schematic diagram indicating how a μCCA is assembled that includes the detailed cardiac MEA system. The silicon μCCA chip (61) is sandwiched between a Plexiglas top cover (60) and an aluminum bottom housing (62) with a recess for the chip and a silicon rubber gasket. The scaling is secured by screws around the edges of the housing. The channels and chambers in the chip are made in silicon with conventional photolithographic techniques using a plasma ion etcher. Channel and chamber dimensions are chosen to replicate PBPK model values for distribution of cardiac output, fluid residence time in a "tissue", and the correct relative sizes of organs/tissues.
Figure 6C:
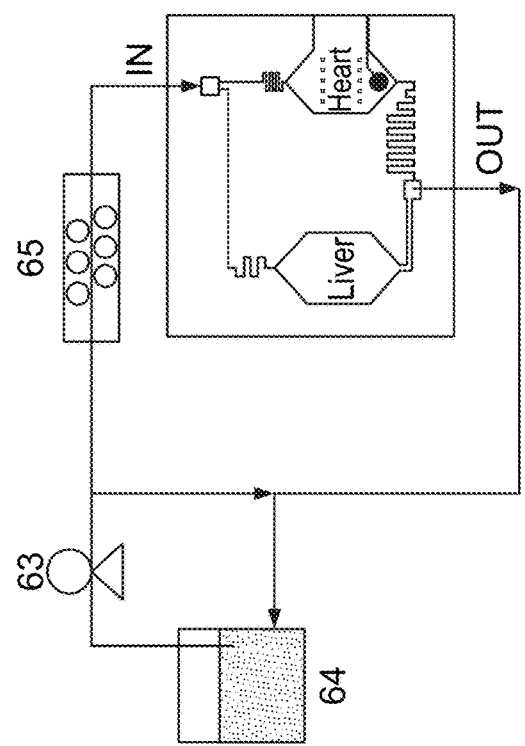
FIG. 6C shows a schematic diagram of operation for a single unit with full re-circulation of medium acting as a blood surrogate. The "other tissues" compartment 64 represents fluid hold-up in non-adsorbing, non-metabolizing tissues which is essential to capture the dynamics of exposure to a chemical. Pump 63 is shown. It also acts as a debubbler or bubble trap 65; a bubble trap provides additional protection allowing reliable operation for at least 72 hours.

Optimizing the pattern geometry to enable paired simulation and measurement of conduction velocity with high fidelity within the cardiac chamber was necessary as demonstrated in FIGS. 3 and 5. However, commercial MEAs have electrodes spaced too close to allow effective measurement of conduction velocity, so the long linear surface chemistry patterns developed in [Natarajan 2011] allowed for measurement of conduction velocity in the spontaneously beating patterned cardiomyocytes effectively. The cardiac/microelectrode functional system was integrated with the device as shown in FIG. 6, which also illustrates how the device is assembled.

Protocols for Cell Culture in the Device

The μCCA in FIG. 4 required the use of liver cells and cardiac myocytes. In FIG. 4GB, pump is 43, other tissues compartment is 44, and bubble is 45. The neonatal cardiac myocyte cultures are obtained from two-day-old rat pups by previously published methods [Dhir 2009; Natajaran 2011]. Cardiac myocytes were plated at a density of $10^5$ cells/mm$^2$ on the patterned MEAs. Approximately 10 days were required for the cultures to establish themselves. Cardiac myocytes were stable on the patterns for at least 30 days. A silicon rubber gasket was used to isolate the tissue chambers on the μCCA prior to assembly to allow optimization of culture conditions in each chamber. After 10 days, cells were introduced to the liver compartment. HepG2/C3A cells derived from a human hepatoma are used. This cell line is available from the American Type Culture Collection (ATCC). They have reasonable levels of most of the cytochrome P450 enzymes and show more "normal" behavior, including modest levels of contact inhibition, than other liver cell lines. Although rat liver cell lines were available, the HepG2/C3A cells contain a more human relevant complement of CYP450 enzymes than a rat cell line. These cells were mixed with Matrigel (BD Matrigel™ Basement Membrane Matrix, LDEV-Free) at 4° C. and placed in the liver chamber. Upon raising the temperature to 37° C. the Matrigel transitions from a liquid (at 4° C.) to a gel entrapping the HepG2/C3A cells as described previously [Sung 2009]. Cells entrapped in Matrigel express higher levels of CYP4501A1 and 1A2 than monolayer cultures. The device was assembled as described previously [Tatosian 2009; Sung 2009]. A single medium was re-circulated throughout the system; the medium is compatible with both cell types and mimics the ability of blood to transport chemicals throughout the body.

One approach to making a common medium is to mix equal parts of the specialized medium for each cell type. In all cases the cells were initially cultured in their compartment on the chip in their preferred medium until cell attachment and differentiation were complete (using a silicon rubber dam to maintain the compartments isolated from each other). Prior to start-up the dam was removed, the specialized media removed, the common medium (with drug or test chemical) added and the system operation was initiated.

Success consists of sustained viability and sustained electrical activity in the cardiac chamber. Viability was measured by combining Cell Tracker Green and the live cell stain. Cell Trace Blue AM (from Invitrogen). Measurement was made by imaging with both a UV (Cell Trace Blue) and FITC (Cell Tracker Green) filter cube. Viable and apoptotic/dead cells were discriminated by direct comparison of both images. Viable cells label with both stains while compromised cells stain weakly or not at all with Cell Trace Blue. Image analysis with Image Pro Plus software (Media Cybernetics) allowed quantification. The method is described in detail in Tatosian and Shuler (2009). Alteration in oxidative capacity of the entrapped HepG2/C3A cells was done by measuring CYP1A1 and 1A2 activity with the ethoxyresorufin-o-dealkylase activity assay [Mufti 1998].

Exposing the Human Liver-Cardiac-Other Tissues μCCA to Challenges from Known Cardiac Antagonists Verapamil (a $Ca^{2+}$ antagonist) was tested at the level of 1 to 10 μM while the antibiotic sparfloxacin (a HERG antagonist) is tested at the level of 10 to 100 μM. Verapamil can cause an irregularity in the spiking activity of cardiac myocytes and, at high concentrations, can reduce beating frequency. Sparfloxacin can cause a lengthening of the QT interval, but it will stabilize beating frequency. It can increase variability in QT intervals and decrease relative refractory period after action potentials. Another compound to be tested, 1-heptanol, is a gap junction blocker. When used at millimolar concentrations, it can decrease the measured conduction velocity. Verapamil can be measured by HPLC [Dakhel 2006] and sparfloxacin by HPLC-PDA [Marona 1999]. The system is operated with and without liver cells in the "liver" compartment. With liver cells present, it can be observed whether metabolism alters cardiac response and toxicity of these compounds or their metabolites on liver and cardiac viability. Sparfloxacin undergoes hepatic glucuronidation and verapamil is oxidized primarily to D-617 and norverapamil by CYP3A4 and CYP1A2.

Results

Response of the system to exposure to cis-permethrin and trans-permethrin independently and to cis- and trans-permethrin in combination. Challenge the human liver-cardiac-other tissue systems with cis-permethrin and trans-permethrin.

Experiments were done with each set of isomers individually (cis then trans) at a range of concentrations (10 μM to 500 μM) to observe effects on cardiac output, viability, and metabolism of the parental compound. Cardiac output was determined from spontaneous beating frequency, conduction velocity, QT interval or refractory period after action potentials [Natarajan 2011]. Viability was determined with live/dead stains as described above. The LC/tandem mass spectrometry method of Scollon et al. [Scollon 2009] was used to measure the levels of cis- and trans-permethrin. It is known that these isomers interact during metabolism, altering dynamic response when mixtures of these permethrin isomers are introduced. For example, the metabolism of the trans form is reduced in the presence of the cis form. Metabolism can be hydrolytic (due to carboxylesterases) or oxidative. The trans-permethrin is hydrolyzed more rapidly (ca. 8 to 50 fold more rapidly) than the cis form. The primary metabolite of hydrolysis is 3-phenoxybenzoic acid [Nakamura 2007]. Oxidative reactions result in a wide variety of metabolites (ca 80). Oxidative reactions occur at the cyclopropane carboxylic acid moiety, at the alcohol moiety, and likely in proximity of the ester bond (which is likely important in the cis forms). There is evidence that the hydrolysis products of permethrin are more cytotoxic than the parent compound (from Nakamura, et al., 2007) and may have species dependence [Sutton 2007]. By removing the liver compartment, the effects of metabolism on cardiac response can be directly determined. Coupled with measurements of trans- and cis-permethrin levels, changes in response to metabolites as well as the parental compounds can be tested.

Length of the Time of Operation of μCCA Devices for Chronic Toxicity Studies with the Toxins Previous μCCA devices developed for drug toxicity measurements are capable of operating for 72 hours without loss of function [Sung 2009]. After 72 hours metabolic waste products accumulate and decrease the viability of cells. Efforts to increase the lifetime of the μCCAs required a focus on both the removal of metabolic waste products and on replenishing the amount of consumed nutrients in the blood surrogate. Replenishing nutrients required the removal of depleted medium and replacing it with fresh medium. This was accomplished by including an intermittent second fluidic loop that replaces a percentage of medium from the inlet reservoir into the system. The fluidic dialysis stream that contains waste products also allows one to continuously analyze waste product concentrations.

On-Chip Microdialysis: The primary waste products generated in μCCA devices were relatively small solutes such as ammonia, lactate, urea, and creatinine. Analyses have shown that naturally the human kidney filters out molecules of up to 66 kDa [Maduell 2005]. Filtering out small molecules such as ammonia and urea can indicate whether they are the most prevalent effectors of cell viability on the chip. The waste removal techniques developed for the μCCA can filter out all waste proteins while maintaining proper ion balance and nutrient concentration in the culture medium.

Figure 7:
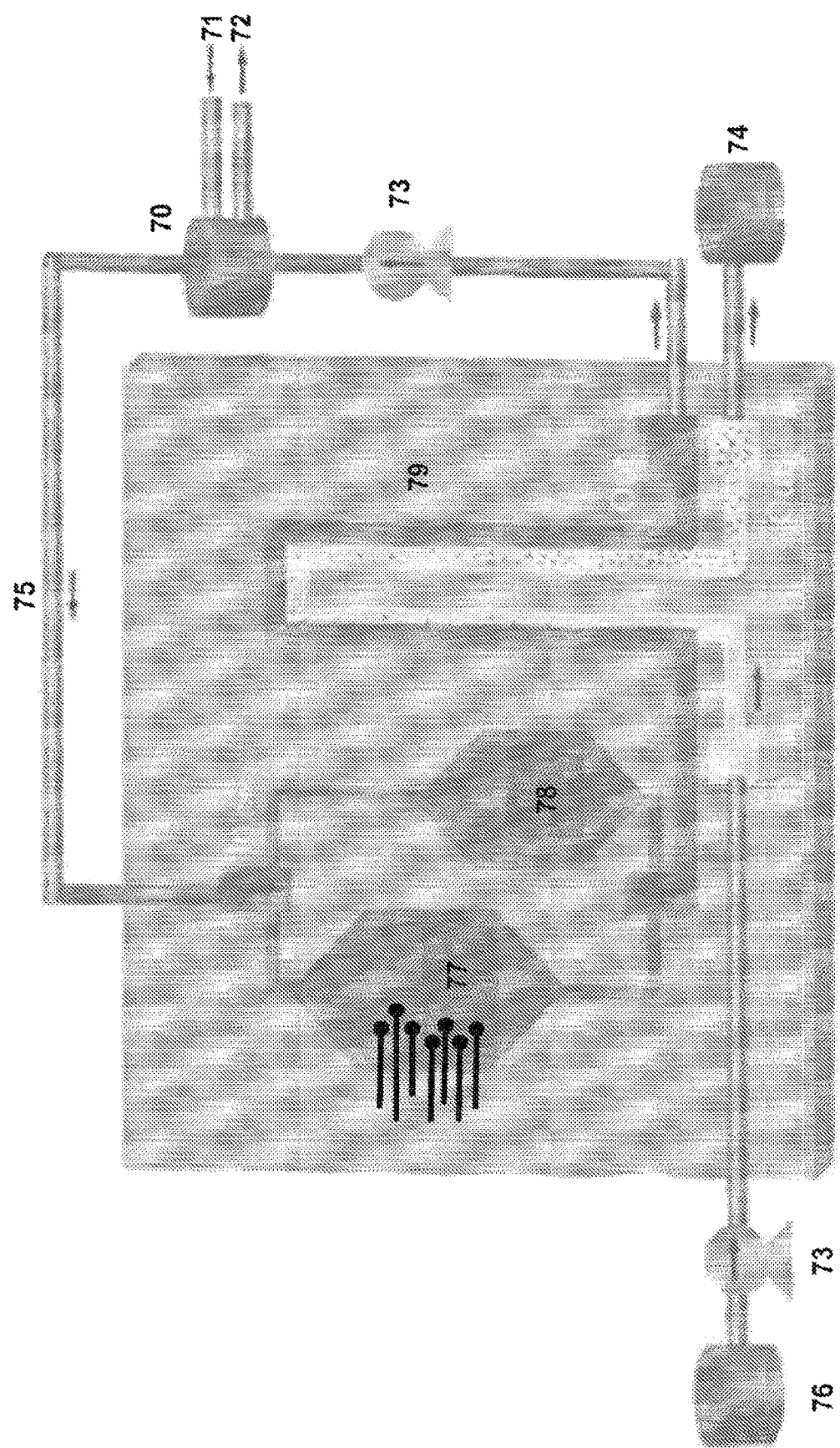
FIG. 7 shows a schematic of a kidney-like chamber, a microdialysis chip with two fluidic circuits and intermittent fresh medium supply: body chip, microdialysis loop, and feeding loop. Medium that circulates within the body chip will be re-circulated via a peristaltic pump. Fresh medium is supplied (and old medium withdrawn) intermittently every 12 hours (~10%). The area of contact between the body chip stream and the dialysis stream depends on the mass transfer coefficients of waste molecules.

The characteristics of two laminar fluid streams at low Reynolds numbers can be used to develop the microdialysis model (FIG. 7). In FIG. 7, the following apply: other tissue component and medium reservoir is 70, fresh medium (intermittent) is 71, removed medium intermittent is 72, peristaltic pump is 73, dialysis outlet is 74, peristaltic tubing is 75, medium reservoir is 76, cardiac myocytes is 77, and liver cells are 78, and dialysis contact loop is 79. If two fluid streams flow parallel to each other, mass transfer of solutes from one stream to another occurs by diffusion. Proteins sized 60 and 66 kDa have been found to have diffusion coefficients of $6.7 \times 10^{-7}$ cm$^2$/s and $6.0 \times 10^{-7}$ cm$^2$/s respectively. In particular, very small molecules such as ammonia and urea that have high diffusion coefficients move faster than larger nutrient molecules with small diffusion coefficients. Creating an interface between the blood surrogate stream containing waste molecules and a fresh dialysate stream allows for the removal of small molecules from the blood surrogate stream. Without a porous barrier, even some large molecules transfer to the dialysate stream, but the effective "cut-off" size for proteins to be removed can be determined by designing the length of the parallel fluid stream in which the two streams are in contact so that the number of large molecules that transfer is limited. The fresh medium stream can also contain nutrient proteins and proper ion concentrations so that the largest diffusion gradient exists for the waste molecules of interest.

The micro-dialysis design required the inclusion of a second fluidic loop on the chip. Both fluidic loops, the general blood surrogate loop and the dialysate loop, were operated with the same pressure drops and fluid velocities so that the interface between the two fluidic streams is stable when they flow parallel to each other without a barrier. Previous designs that required two fluidic streams in µCCA devices, such as those that incorporated the apical side of a digestive module onto the chip, indicated that careful fluid circuit design can accomplish the needed pressure balance [Mahler 2009].

Replenishing Nutrients: Replenishing nutrients required the supply of new culture medium to the chip and the removal of depleted medium. New medium can be supplied using a three fluid circuit design but can be difficult to balance. Nutrients are supplied in the "fresh" medium stream although the rate of nutrient supply and waste removal is coupled. In an effort to reduce the complexity of the fluidic circuit design, the Shuler lab has demonstrated a "pumpless" system using gravity driven flow for the operation of µCCAs [Sung 2010]. Chips were placed on a rocker platform and two reservoirs were used; the system was tilted in one direction for 3 minutes and then reversed. Using this principle, the fluid flow rates in each circuit were determined by the difference in height of the fluid in the supply reservoirs and the outlet reservoirs as well as the channel dimensions. It was shown that gravity driven flow could generate flow rates that were sufficient to operate the chip in a manner that was comparable to that achieved with pressure driven flow via peristaltic pumps. Developing µCCAs with gravity driven flow offers the advantage that with careful design more fluid streams can be incorporated for nutrient re-supply.

Chronic toxicity measurement and Continuous Monitoring of the Dialysis Stream: Starting with day 10, spontaneous beating frequency, conduction velocity and QT interval were measured in the cardiac compartment. The variability of all of these parameters (without drug effects) can be within the ±10% changes/day limits. Histological and physiological studies were performed to ensure viability and stability of the system. Reference compounds with known cardiac effects as well as with known metabolism and absorption were used.

Another method to determine the influence of environmental toxins on the metabolism of cells in µCCA devices was to continuously monitor the dialysate for cellular waste products such as ammonia, urea, and creatinine. On chip, the monitoring of ammonia, urea and other waste molecules gave information on the status of the cells. Many protein assays rely on the addition of substrates and subsequent generation of a product that changes the absorption characteristics of the fluid in which the proteins are contained. On the chip the absorption of light was measured via a detector underneath the chip that measures the light passing through from a source above. A similar system that has been developed in Shuler's laboratory for the detection of P450 enzyme activities can be adapted to measure the absorption of light by medium that has undergone the assay [Sung 2009].

Figure 8A:
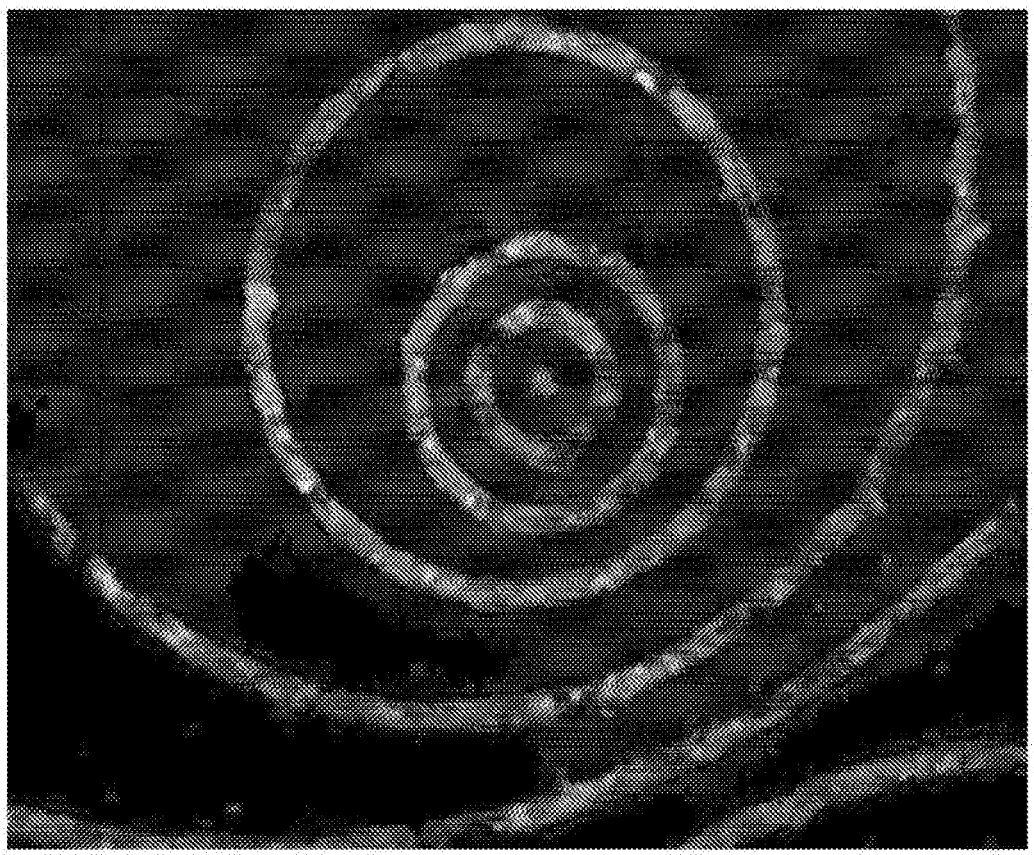
FIGS. 8A-8B show PEG/FN patterned stem cell derived cardiomyocytes, 2 Days after plating.
Figure 8B:

Data have been obtained from cardiomyocytes derived from a number of hiPSC lines (>40) generated in the Mercola laboratory in the Sanford-Burnham Research Institute. Thin needle intracellular electrophysiological recording revealed APs characteristic of immature and ventricular-like cardiomyocytes, as typical for hESC-cardiomyocytes [Kim 2010; Kita-Matsuo 2009]. In a major advance, experiments have shown that human stem cell-derived cardiac myocytes pattern and are spontaneously active on the PEG/fibronectin surfaces in serum-containing media (FIG. 8). Matrigel was the unpatterned positive reference.

Figure 9A:
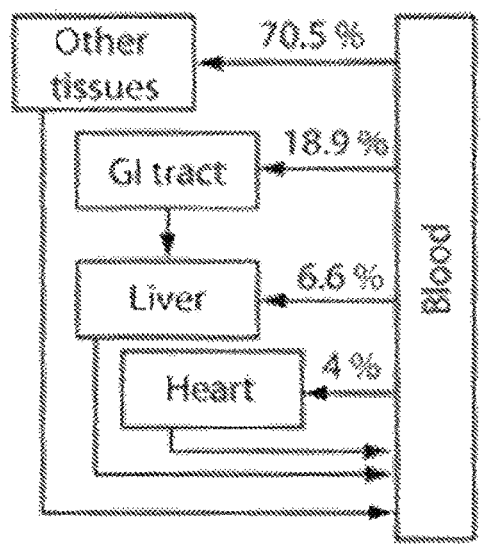
FIGS. 9A-9B show the design of GI/liver/heart/other tissue system.
Figure 9B:
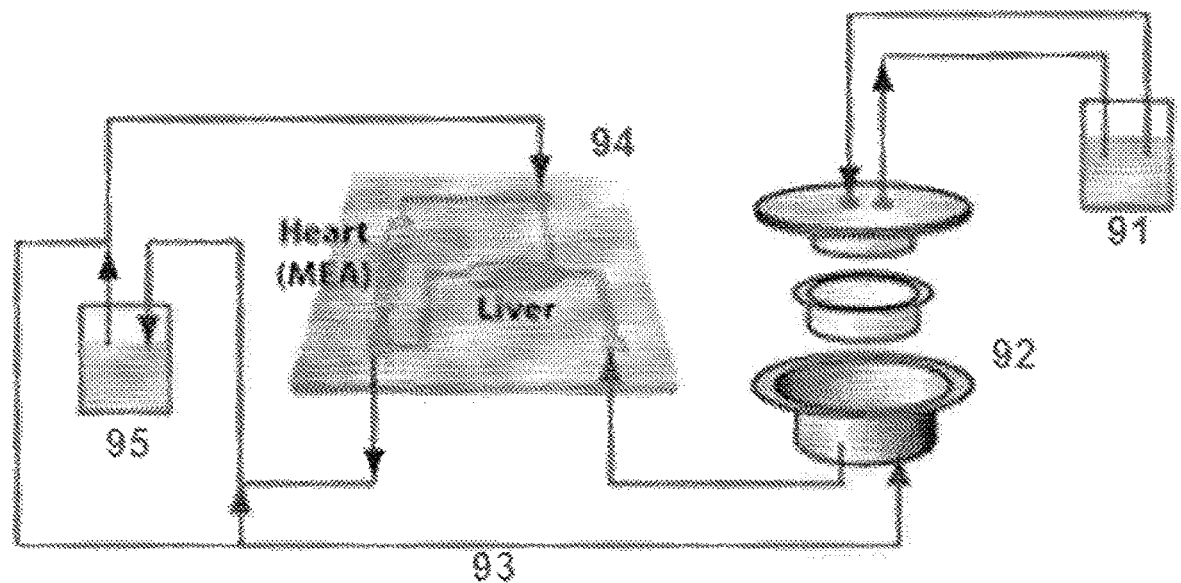
Figure 10A:
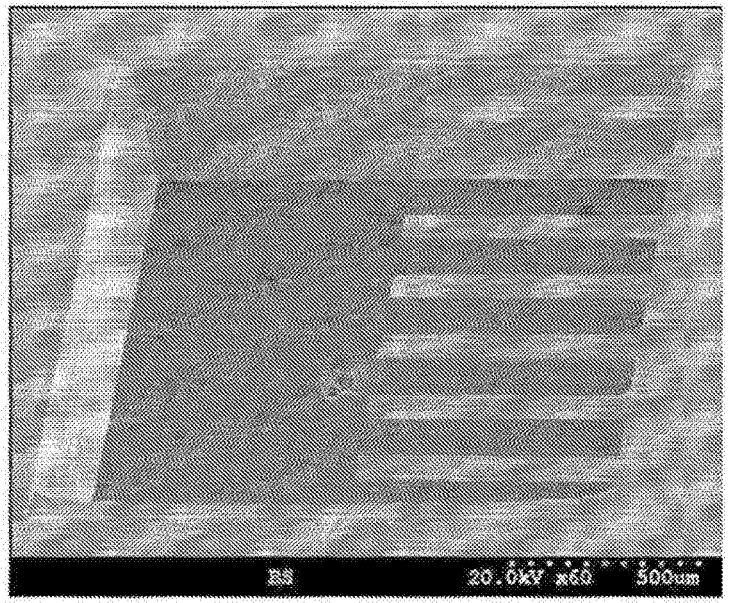
FIGS. 10A-10C show details of the functional assay system for measuring skeletal muscle contraction in vitro.
Figure 10B:
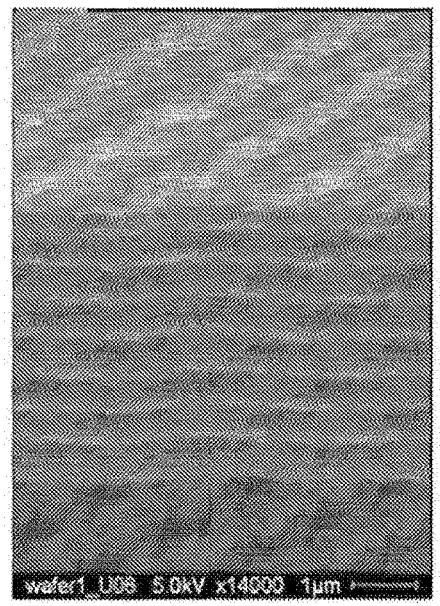
Figure 10C:
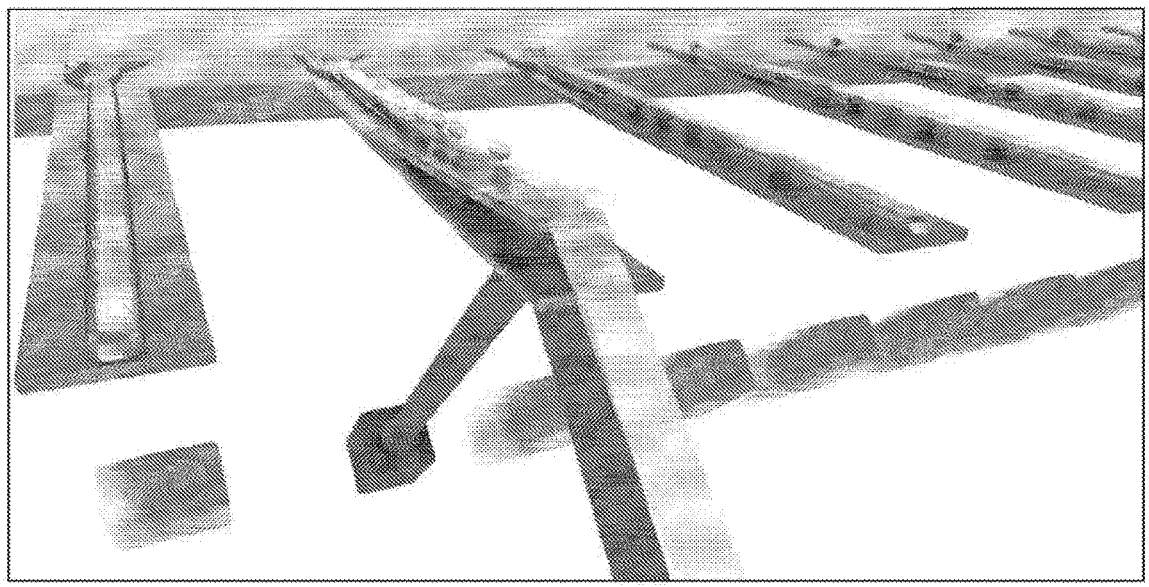

A GI tract with a systemic model consisting of liver/cardiac/other tissues was used with the µCCA. Realistic models of the GI tract consist of Caco-2 (representing epithelial cells in the intestine) and HT29-MTX cells (representing mucus-producing goblet cells) co-cultured as a mixed population with 75% Caco-2 cells [Pointer 2001]. This mixed population forms a coherent structure supported on a polycarbonate membrane. It forms tight junctions, possesses microvilli, can transport small molecules by all four major transport routes, and expresses most phase I and phase II enzymes and mimics absorptive enterocytes. A mucus layer from the goblet-like cells coats the surface in a layer up to 10 µm thick. By integrating a GI tract model with a body model, human response to oral ingestion of a chemical can be predicted. The GI tract model has been incorporated with the body modules previously developed [Mahler 2009; McAuliffe 2008]. FIG. 9 depicts an integrated GI tract/liver/cardiac/other tissues model. In FIG. 9B, the schematic of device shows sample/chyme in 90, GI tract chamber in 92, pump to basolateral GI tract chamber in 93, body chip in 94, and body fluids/other tissues compartment in 95.

A design for a "pumpless" system has also been described [Sung 2010] that would allow multiple units to be operated simultaneously with minimal preparation or assembly. The device could be dosed automatically and the readout (both optical and electronic) recorded electronically. Such a high throughput device with both greater metabolic realism and functional reporter tissues for CNS, heart and muscle can significantly improve testing of potential environmental toxins.

Example 2—Support for Muscle Cells on Cantilevers (FIGS. 10-13)

i) Experimental Materials and Methods
Cantilever Fabrication

Chips containing an array of individual cantilevers were produced from silicon-on-insulator (SOI) wafers fabricated using previously published methods (Das et al., 2007; Wilson et al., 2010, each of which is incorporated herein by reference in its entirety for teachings related to cantilever fabrication). Briefly, to produce the devices, 100 mm SOI wafers with a 4 µm thick device layer and buried oxide layer of 1 µm were used. The cantilever structures were produced in the device layer by patterning with photolithography methods using S 1818 photoresist and etching using deep reactive ion etching (DRIE). The buried oxide layer acted as an etch stop. A 1 µm thick layer of silicon dioxide was deposited on top of each of the cantilevers using plasma enhanced chemical vapor deposition (PECVD) so as to protect the cantilevers during processing. The backside of the wafer was similarly patterned and etched using a second mask. When the silicon beneath the cantilevers was removed, a large window underneath an array of cantilevers remained. The buried oxide layer and oxide layer protecting the cantilevers were removed using a buffered oxide etch solution. The resulting structures were freestanding, bare silicon cantilevers that could be imaged from above and interrogated with a laser from below. The chips were separated by cleaving along perforated edge lines produced during the backside etch. Dimensions of the cantilevers were verified using scanning electron microscopy.

DETA Surface Modification

To promote cell adhesion to the cantilevers and control glass coverslips, the surfaces were coated with an amine-terminated alkylsilane, (3-Trimethoxysilyl propyl) diethylenetriamine (DETA) (United Chemical Technologies, Bristol, PA) using methods published previously (Das et al., 2010; Guo et al., 2010; Wilson et al., 2010, each of which is incorporated herein by reference in its entirety for teachings related to DETA surface modification). DETA is an analog of spermidine; a natural polyamine known to promote long term survival of cells in vitro (Eisenberg et al., 2009; Kaeberlein 2009). This surface coating has been used extensively to modify surfaces for the culture of a variety of cell types (Das et al., 2010; Guo et al., 2010; Das et al., 2007; Wilson et al., 2010; Das et al., 2006; Rumsey et al., 2010; Rumsey et al., 2009).

The cantilevers and glass coverslips were acid washed in baths of concentrated HCl in methanol (1:1) and concentrated $H_2SO_4$, followed by rinsing in boiling de-ionized water and oven drying. The surfaces were silanized using a solution of 0.1% DETA-silane in toluene, which was heated to 70° C. for 30 minutes. To remove any unreacted silane, the surfaces were subjected to a series of toluene rinses with reheating to 70° C. for 30 minutes in fresh toluene. The surfaces were oven cured at 110° C. for 2 hours and stored in a desiccator until use. The surface coatings were verified using X-ray photoelectron spectroscopy and contact angle goniometry.

Cell Culture

All incubations were performed in a 37° C., 5% $CO_2$ incubator. Muscle cells were isolated from E18 Sprague-Dawley rat fetuses. Pregnant rats were then euthanized by exposure to an excess of $CO_2$.

Muscle tissue was dissected from the hind limbs of E18 fetuses and transferred to a 0.25% trypsin solution (Life Technologies, Grand Island, NY). To dissociate the tissue fragments into a single cell suspension, this solution was placed in a shaking water bath set at 37° C. and 100 rpm for 25 minutes. The cell suspension was triturated and run through a 100 µm mesh filter in order to remove any un-dissociated tissue fragments. The cells were then plated onto an uncoated, 100 mm dish and left for 30 minutes at room temperature. After this time, the non-adherent cells were collected in the supernatant and the adherent cells were discarded. Because fibroblasts adhere more rapidly to tissue culture plastic and therefore are selected out, this step enriched the myogenic precursor (myoblast) population, (Machaida et al., 2004). The muscle cell suspension was spun at 300 g for 5 minutes and the pelleted cells re-suspended in a defined muscle proliferation medium developed previously (Table 1). Cells were plated onto DETA coated silicon cantilever chips at an initial density of 2000 cells/$mm^2$ and maintained for 4 days in vitro (DIV). At this point the proliferation medium was replaced with a differentiation medium to promote myoblast fusion into primary myotubes. The differentiation medium contained NBActiv4 (Brain Bits, Springfield, IL)+1% antibiotic/anti-mycotic (i.e., Amphotericin B. Penicillin, and Streptomycin mixture at 100× concentration) (Life Technologies). As described in Brewer et al., 2008, NbActiv4™ comprises all of the ingredients in Neurobasal™, B27™, and Glutamax™, and can also comprise creatine, estrogen, and cholesterol. Cells were maintained in this medium for another 3 days in vitro (DIV).

TABLE 1

Components of Defined Muscle Proliferation Medium

| Component | Conc. | Company (Catalog No.) |
|---|---|---|
| Neurobasal medium | N/A | Life Technologies (21103-049) |
| B27 (50x) | 1x | Life Technologies (17504044) |
| Glutamax (100x) | 1x | Life Technologies (35050061) |
| G5 supplement | 1x | Life Technologies (17503-012) |
| Glial-Derived Neurotrophic Factor | 20 ng/mL | Cell Sciences (CRG400B) |
| Brain-Derived Neurotrophic Factor | 20 ng/mL | Cell Sciences (CRB600B) |
| Ciliary Neurotrophic Factor | 40 ng/mL | Cell Sciences (CRC400A) |
| Neurotrophin-3 | 20 ng/mL | Cell Sciences (CRN500B) |
| Neurotrophin-4 | 20 ng/mL | Cell Sciences (CRN501B) |
| Acidic Fibroblast Growth Factor | 25 ng/mL | Life Technologies (13241-013) |
| Vascular Endothelial Growth Factor | 20 ng/mL | Life Technologies (P2654) |
| Cardiotrophin-1 | 20 ng/mL | Cell Sciences (CRC700B) |
| Heparin Sulphate | 100 ng/mL | Sigma (D9809) |
| Leukemia Inhibitory Factor | 20 ng/mL | Sigma (L5158) |
| Vitronectin | 100 ng/mL | Sigma (V0132) |

Myotube Contraction Detection System

Myotube contraction was recorded and characterized via measurement of cantilever deflection using a laser system. In this system, cantilevers supporting co-cultured myotubes and motoneurons were inserted into a transparent culture dish fitted into a modified upright Olympus BX51WI electrophysiology microscope. The culture dish was filled with NBActiv4 medium (+10 mM HEPES) to maintain the cells during the analysis. A heated culture dish system (Delta T, Bioptechs, Butler, PA) was incorporated into the stage to maintain the culture at 37° C. throughout the analysis.

The laser system consisted of a Helium Neon laser beam that was scanned across the tip of each cantilever at a 30° angle relative to the plane of the cantilever. A quadrant photo-detector module was also moved to detect the reflected beam. A temperature-controlled stage was incorporated into the unit to maintain the cells at physiological temperature. Stainless steel electrodes were mounted inside the stage dish at a separation distance of 15 mm. To allow the system to produce field stimulation of myotubes when appropriate, the electrodes were connected to a pulse generator (A-M systems, Sequim, WA), which was capable of producing field stimulation pulses of varying intensity, frequency, and waveform.

The photo-detector and pulse stimulator were connected through an Axon Instruments 1440 digitizer (Molecular Devices, Union City, CA) to a computer running AxoScope 10.0. The change in position of the reflected laser beam on the photo-detector was recorded in AxoScope, along with the timing of any electrical field pulses produced by the pulse generator.

Measurement of Myotube Contraction in Response to Neuronal Stimulation

Broad field electrical stimulation was used to verify the contractile ability of the cultured myotubes. Cultures were subjected to a 3 V, 40 ms pulse at a frequency of 1 Hz, and the cantilevers were scanned for 5 seconds each to identify those with active myotubes. A representative trace demonstrating the response of cultured myotubes to this stimulation is provided in FIG. 11 A-D. Across all experimental conditions, a successful contractile response was taken as any peak equal to or larger than 0.1 V.

Figure 11A:
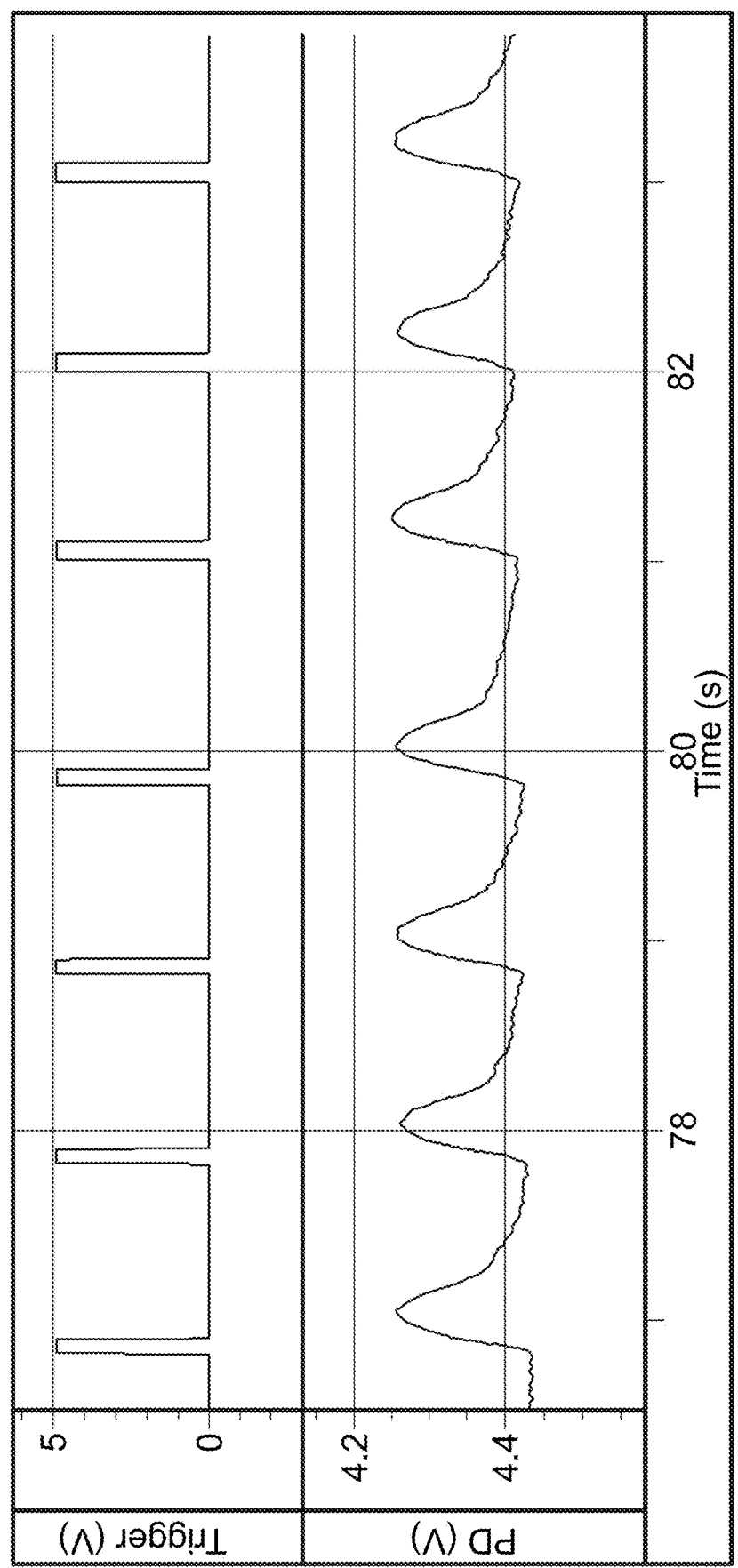
Figures 12A, 12B:
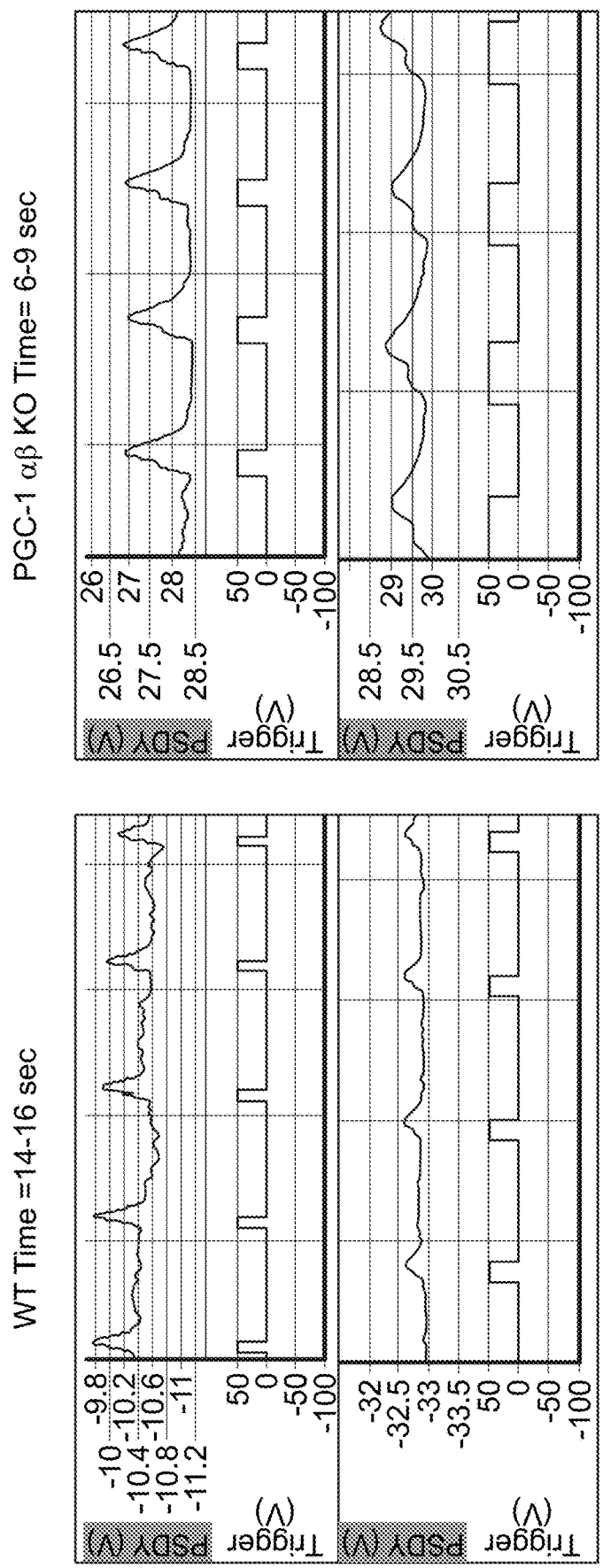
FIGS. 12A-12B are graphs showing recapitulation of in vivo disease phenotype is recreated in this in vitro assay system.
Figure 13A:
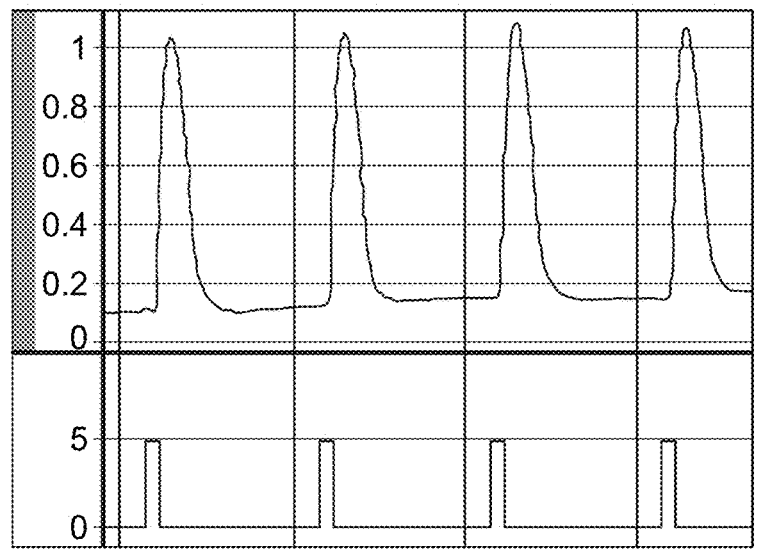
FIGS. 13A-13C show chronic low frequency stimulation (CLFS) of myotubes on cantilevers emulates exercise in vitro.
Figure 13B:
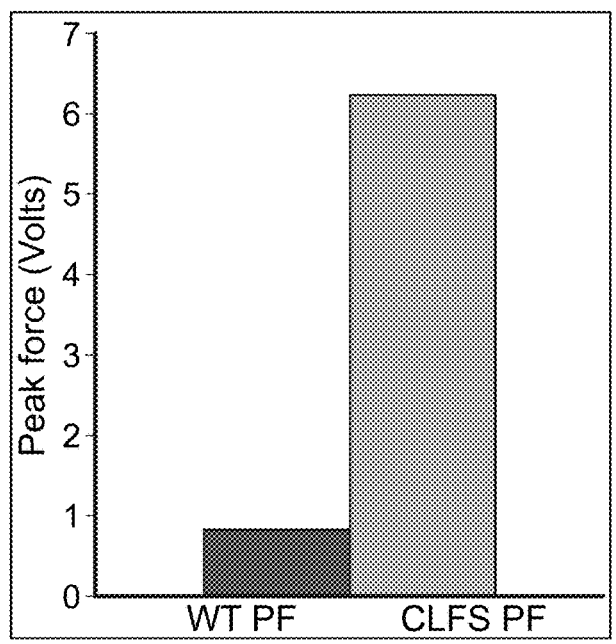
Figure 13C:
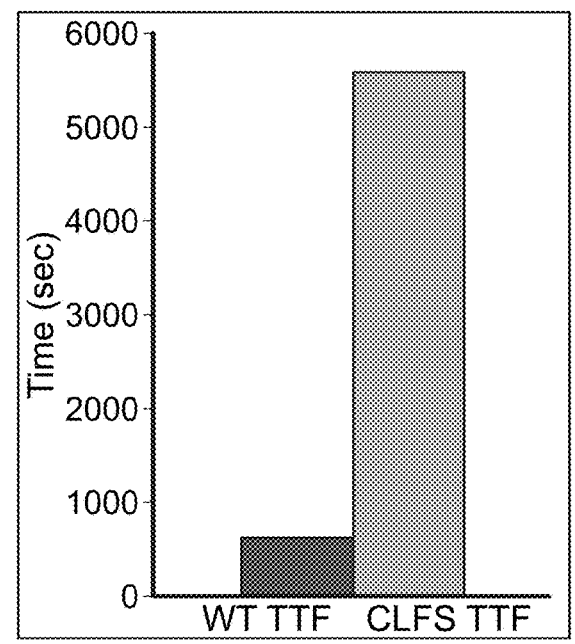

FIGS. 11 A-D, 12 A-B and 13 A-C show the data of the experiments using a component comprising muscle cells on a cantilever.

Example 3—Cardiac Function (FIG. 14)

Figure 14A:
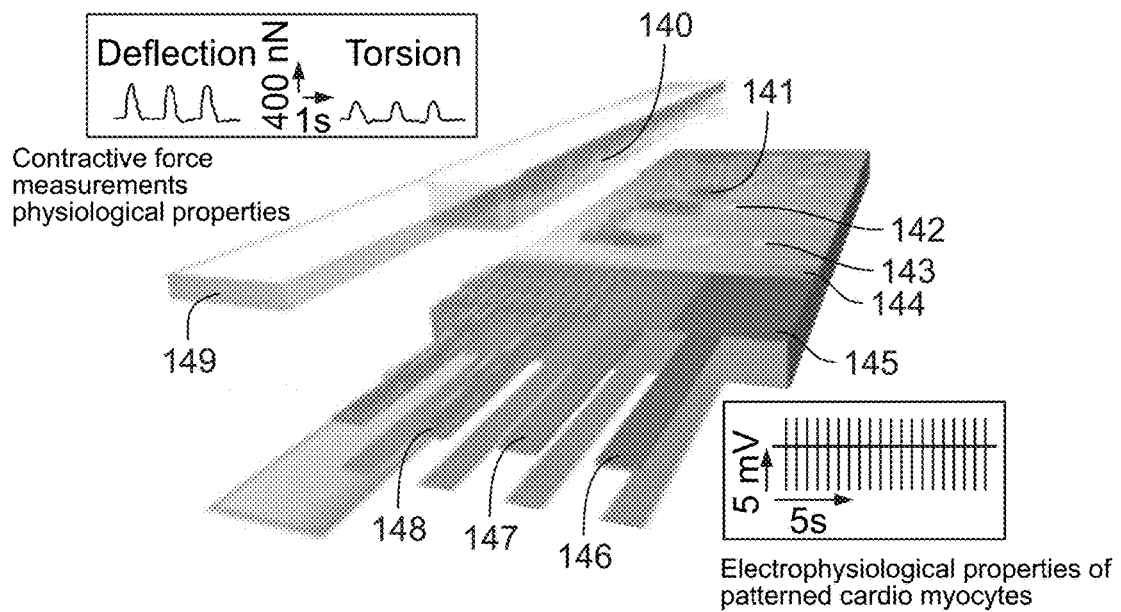
FIGS. 14A-14F show integrated microelectrode arrays and silicon cantilevers for measurement of cardiac function in vitro.
Figure 14B:
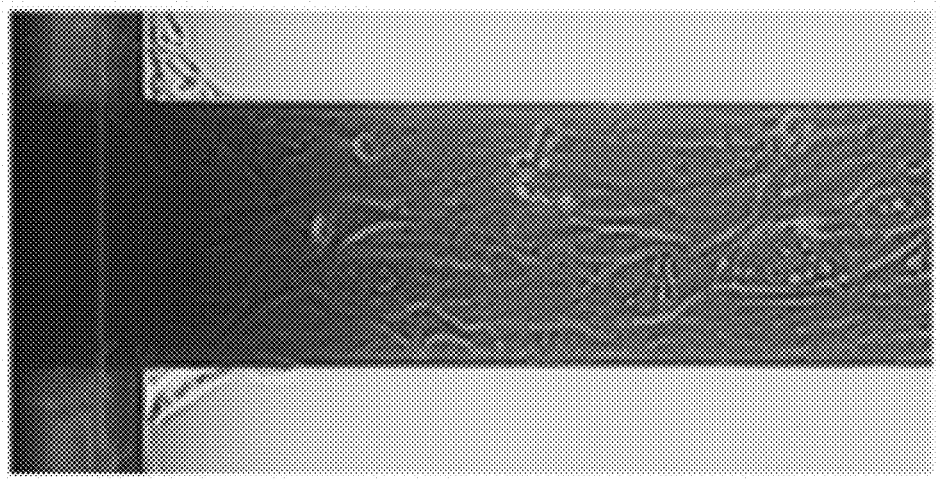
Figure 14C:
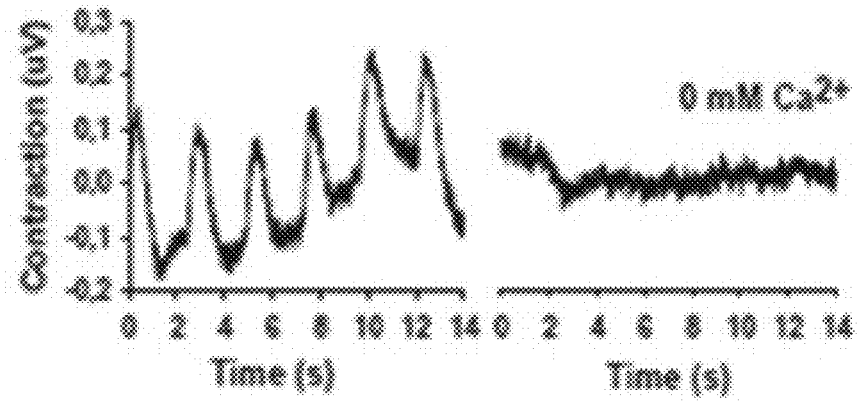
Figure 14D:
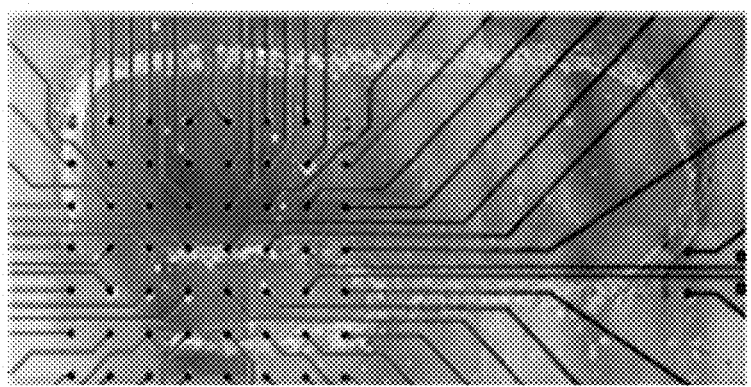
Figure 14E:
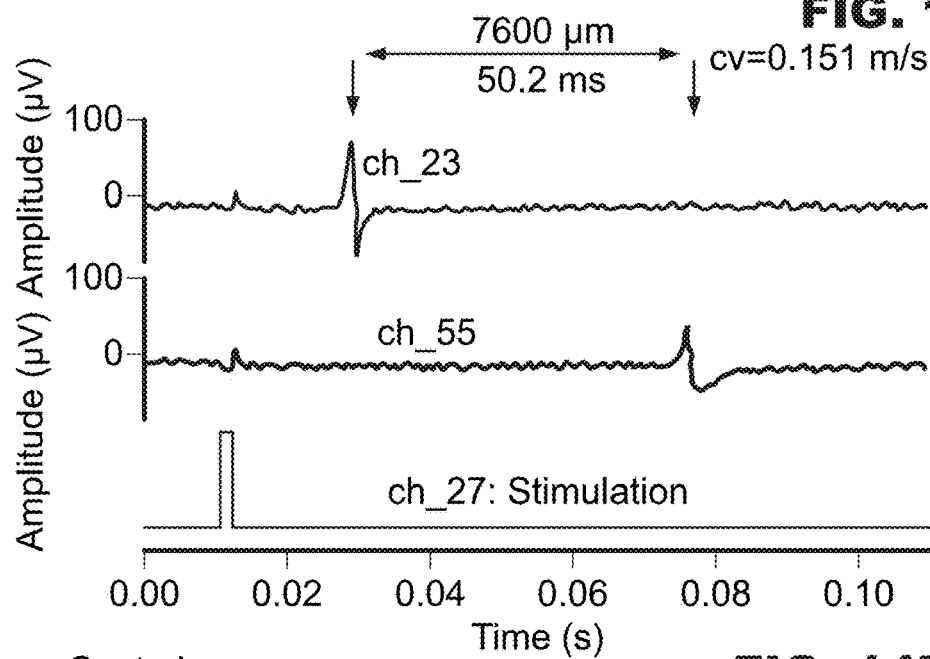
Figure 14F:
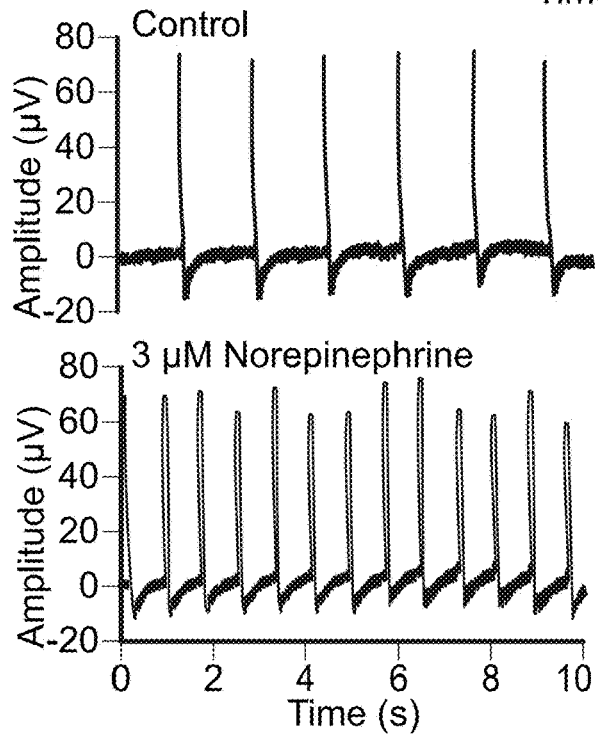

The disclosed systems are based on human cardiac myocytes. As described herein, the incorporation of a functional cardiac system based on patterned cardiac cells integrated with microelectrode assays enabled the measurement of several cardiac parameters including conduction velocity, peak amplitude and spontaneous frequency, QT interval, and relative refractory period (which is related to triangulation). In doing so, the disclosed systems demonstrated high predictive value for cardiac side effects, electrical conduction, and cardiac muscle force generation. As shown in FIGS. 14A-F, cardiac function can be mimicked or simulated using a component comprising a microcantilever detection system (14A) or a patterned MEA (microelectrode array), FIG. 14D. In FIG. 14A, the following apply: hydrogel containing vascular networks is 140, cardiac cells are 141, patterning is 142, substrate-integrated gold-electrode is 143, insulation is 144, silicon wafer is 145, cantilever is 146, patterning is 147, cardiac cells are 148, and upside down glass with vascular networks is 149.

ii) Materials and Devices

Preparation of Cell Culture Medium

In a cardiac component, the human-derived cardiac myocytes were cultured in a serum-free medium. The medium was optimized to enhance human cardiac myocyte growth and differentiation. Specifically, the medium was supplemented with specific growth factor such as epidermal growth factor (EGF) or hormones such as hydrocortizone and L-thyroxin. In an aspect, the serum-free medium can comprise 100 mL Ultraculture medium (Bio Whittaker Cambrex) supplemented with 10 mL B27, 1 mL L-glutamine (Gibco/Invitrogen), 1 mL Penicillin Streptomycin, 0.375 g dextrose (Fisher Scientific) in 800 µL water, 1 mL nonessential amino acids and 1 mL of Hepes buffer (Gibco/invitrogen) (Sathaye et al., 2006). Additional growth factors can also added to improve cell survival in the serum-free conditions including 0.1 µg/mL of L-thyroxine, 10 ng/mL of epidermal growth factor (Sigma-Aldrich), and 0.5 µg/mL of hydrocortisone (BD biosciences).

Fabrication of Cantilever

The layout for the cantilevers was generated using AutoCAD 2004. The patterns were written to chrome coated 5-inch sodalime glass masks for front and backside photolithography. Cantilevers were fabricated from 6-inch double-sided polished silicon-on-insulator (SOI) wafers with a 5 µm crystalline silicon layer (front side) and a 500 µm silicon dioxide layer (back side). The front side was primed with a 10 nm layer of hexamethyldisilazane (HMDS) to promote resist adhesion. A 5 µm layer of the photoresist AZ 5214 E (Clariant, Muttenz, Switzerland) was spun onto the device layer followed by softbake, alignment, exposure, and development. The device layer was etched using the deep reactive ion etch (DRIE) process at a rate of 2 µm/min. Resist was stripped and a 0.5 µm thick layer of silicon dioxide was deposited via Plasma Enhanced Chemical Vapor Deposition (PECVD) to protect the device layer during subsequent processing. The wafer was then flipped over and was primed with a 10 nm layer of HMDS and spun with 4.15 µm layer of AZ 9245 photoresist (Clariant, Muttenz, Switzerland). Coating was followed by softbake, front-back alignment, development, and DRIE etch at 4 µm/min until the bulk of the back side had been etched through leaving only the buried native oxide layer. The devices were then subjected to a buffered HF dip to remove the buried native oxide layer as well as the silicon dioxide that had been deposited onto the device layer. Individual devices were separated by breaking connecting tabs that were incorporated into the device design. Cantilever dimensions were measured using a JEOL 6400 scanning electron microscope (SEM) at a take-off angle of 50° off normal.

The silicon cantilevers were coated with the amine-terminated alkylsilane, (3-Trimethoxysilyl propyl) diethylenetriamine (DETA) (United Chemical Technologies, Bristol, PA) to promote cell adhesion and differentiation (Ravenscroft et al., 1998). Cantilevers were cleaned in serial acid baths of concentrated HCl in methanol (1:1 dilution) for 30 minutes and concentrated $H_2SO_4$ for 1 hour, followed by 30 minutes in boiling de-ionized water. Cleaned cantilevers were dried overnight in an 80° C. oven. Surface modification was performed according to a previously published protocol (Das et al., 2008). Briefly, the cantilevers were incubated in 0.1% solution of DETA in toluene for 30 minutes under gentle heating (approximately 70° C.), followed by 3× wash in fresh toluene. The coated cantilevers were then heated in fresh toluene for 30 minutes followed by drying overnight in an 80° C. oven. Coated samples were stored in a desiccator until use. X-ray photoelectron spectroscopy (XPS) and contact angle measurements were used to characterize the surface coating.

Fabrication of Piezoelectric Elements for Cantilevers

The skilled person in the art is familiar with piezoelectric microcantilever fabrication and function (see, e.g., Choudhury et al., 2007 and Datar et al., 2009). Piezoelectric Devices Piezoelectricity is the ability of certain materials (crystals and certain ceramics) to generate an electric potential in response to applied mechanical stress (Holler et al., 2007). The piezoelectric effect is used in various sensors to measure stresses or geometrical deformations in various mechanical devices. The reverse piezoelectric effect turns piezoelectric material into actuators, when an external voltage is applied to the crystal (King et al., 2000). Piezoelectric materials are known to the art and include, but are not limited to, the following: quartz, bone, sodium tungstate, zinc oxide, or lead zirconate titanate (PZT) (Lou 2009). A similar effect is the piezoresistive phenomenon. When subjected to mechanical stress, these materials change resistivity (Mutyala et al., 2009).

Silicon wafers with silicon on insulator can serve as base material in the fabrication of piezoelectric cantilevers. An additional layer of 100-200 nm $SiO_2$ can be deposited onto the base material to insulate conductive materials from the semiconductive silicon. Metal layers can be fabricated to connect the piezoelectric components with microelectronics. Layers of piezoelectric materials, such as ZnO and PTZ sol-gel, can be deposited exactly in those areas where microcantilevers remain after the etching process. Another conductive layer contacts the piezoelectric components from top to apply voltages for actuation or current read out during sensor mode. An insulation layer of silicon-ONO-stacks (oxide-nitride-oxide) can protect conductive elements from aqueous solutions during cell culture. Alternatively, piezoelectric elements can be replaced by piezoresistive materials. This alternative approach can offer a higher sensitivity during readout; however, piezoresistive materials do not provide the usage of the cantilevers as actuators and a field stimulator would be needed.

Fabrication of Microelectrode Array

Generally, the amount of information that could be obtained using traditional MEAs was limited. Not only contact interaction with the surface, but also the shape of the attachment area determines the physiology of cardiac myocytes. Pattern geometries determine the extent of the alignment of the long axis of cardiac myocytes, alignment determines CV and other physiological and pharmacological properties of cardiac tissues (Parker et al., 2008; Bourgeious et al., 2009; Badie et al., 2009). Therefore, in the experiments described herein, the cardiac myocytes were patterned on the top of the microelectrodes. In doing so, the measurement of conduction velocity along a well-defined path became possible, which extended the capability of MEA measurements by including field potential (AP) length. Consequently, the amount of information that could be obtained using MEAs increased. As described herein, the incorporation of a functional cardiac system based on patterned cardiac cells integrated with MEAs enabled the measurement of conduction velocity, peak amplitude and spontaneous frequency. QT interval and relative refractory period (which is related to triangulation).

Cardiac myocytes cultured on microelectrode arrays (MEA) have several benefits compared to either traditional patch clamp electrophysiology or isolated organ methods. The use of MEAs in the investigation of cardiac side effects is more cost effective when compared to standard patch-clamp electrophysiology. Furthermore, cardiac myocytes can be maintained over longer periods of time on MEAs, thus chronic experiments can be feasible. Furthermore, in the system disclosed herein, the serum-free medium used in to culture the cardiac myocytes increases the reproducibility of the disclosed system.

Cardiac myocytes can be patterned on glass using photolithography following surface modification with self-assembled monolayers (SAMs) for myocytes (Dhir et al., 2009, Molnar et al., 2007). The benefit of this method is the compatibility of the technique with cheap automated silicon manufacturing steps and the ability of the cells to self-assemble after random plating. Self-assembled monolayers or SAMs are one molecule thick monolayers attached to a surface composed of organic molecules. Surface modification with SAMs is also compatible with advanced photolithography methods (Ravesncroft et al., 1998; Corey et al., 1991). Cells survive on patterned surfaces for extended periods of time (Das et al., 2008; Das et al., 2010), do not migrate off the patterned areas (Corey et al., 1991) and exhibit the typical morphology and physiology of the specific cell type (Das et al., 2004 Lochter et al., 1995).

MEA's containing 60, 10 µm diameter electrodes (Multichannel Systems, Germany) were cleaned by soaking the arrays in a detergent solution for 2 hours followed by sonication for 10 minutes. The arrays were then oxygen plasma cleaned for 20 minutes. Surface modification was completed by incubation of the MEAs in a 3 mM PEG silane, 2-[Methoxypoly(ethyleneoxy)propyl]trimethoxysilane (MW=460-590, Gelest), solution in toluene, with 37% concentrated HCl added to achieve a final value of 0.08% (0.8 ml HCL/L), for 45 minutes at room temperature. The arrays were then rinsed once in toluene, twice in ethanol, twice in water and sonicated in water for 2 minutes to remove the non-covalently linked material (Popat et al., 2004). The arrays were air dried with nitrogen and stored in a dessicator overnight.

The MEAs were patterned using a deep UV (193 nm) excimer laser (Lambda Physik) at a pulse power of 230 mW and a frequency of 10 Hz for 45 seconds through a quartz photomask (Bandwidth foundry, Eveleigh, Australia). The arrays were sterilized using 70% isopropanol and then incubated with 5 µg/mL of fibronectin in a phosphate buffered solution (Invitrogen) for 20 minutes at room temperature. The solution was removed and the surface was first rinsed with PBS, followed by the plating medium, and then dried before the cells were plated.

SAM-modified surfaces are characterized using XPS to demonstrate formation of the SAM and contact angle measurements to quantify wettability. Contact angle measurements are a rapid and simple measure of wettability. Contact angles are measured by application of static, sessile drops (5-30 µL) of deionized water to substrate surfaces with a micropipetter. The measurements are made visually on both sides of the drops using a Rame-Hart type goniometer. XPS is a technique for the elemental analysis and characterization of surfaces (Briggs 1992). Since the electrons of each element possess characteristic binding energies, the energy pattern of emitted photoelectrons arising from a given element serves to unambiguously identify that element, while the precise peak positions, or chemical shifts, reflect the chemical environment (i.e., oxidation state) in which the element is found. XPS measurements are obtained on a FISONS 220i XL spectrometer with imaging capability to 2 11 m resolution. For each sample examined by XPS, a survey spectrum and high-resolution spectra for the elements Si. C, N, and any other element that is unique to the SAM was obtained (F for 13F). These measurements serve as (a) baseline quantities against which to contrast properties of the surface after cell culture, and (b) baseline quantities against which to contrast cell growth and survival from experiment to experiment for multivariate analysis.

Detection System Setup

Spontaneous or electrical stimulation-evoked force generation of cardiac myocytes was measured based on optical or electrical detection of cantilever-bending. Optical detection of displacement of the end of the cantilever was based on the principle routinely used in atomic force microscopes (AFM) in which a laser beam was reflected from the cantilever to a sensor. The sensor detected the displacement of the laser beam caused by changes in the position of the cantilever. In this optical detection method, an automated electrical shutter was placed in the beam path. This placement minimized the exposure of the cells to the reflected laser light. Electrical detection of the displacement was based on piezoelectric principle that requires special design and materials for the fabrication of the cantilevers. Both detection methods enabled automation and high-throughput screening on myocyte contraction force. Peak contraction force and force-contraction velocity relationships were calculated based on the geometry of the cantilevers and the thickness of cultured cardiac myocytes (determined from immunostaining data). Compounds (such as norepinephrine, verapamil, and sotalol) were applied using traditional methods to the medium and possible changes in force or force-velocity relationship were detected and analyzed using standard statistical methods.

A detection system similar to those used in atomic force microscope (AFM) system was designed for measuring deflection of the cantilevers during contraction. The entire system was assembled around an upright Olympus BX51WI electrophysiology microscope (Olympus Inc., Center Valley, PA). The detection system consisted of a class 2 red photodiode laser (Newport, Irvine, CA), a stimulation chamber, a 4-quadrant photodetector (Noah Industries, Melbourne, FL), and a computer with pClamp 10.0 data acquisition software (Molecular Devices, Union City, CA). The laser and photodetector (PD) were mounted on x-y-z-h translators (Newport, Irvine, CA), which were mounted on the underside of the microscope stage. The stimulation chamber was fabricated from 5 mm thick polycarbonate sheet. An approximately 15 mm×15 mm square chamber was milled out of the sheet and fitted with silver wires (0.015 inch diameter) for field stimulation. The silver wires were mounted parallel to each other with a separation of 15 mm. The bottom of the chamber was sealed using a 22 mm×22 mm glass coverslip. This created a transparent base through which the laser beam could easily pass. The silver wires were connected to an external pulse generator (A-M systems, Sequim, WA) capable of producing field stimulation pulses of varying intensity, frequency, and waveform. Both the pulse generator and PD were connected to an Axon Instruments series 1440 digitizer (Molecular Devices, Union City, CA) which was interfaced with the computer.

The AFM system was calibrated using a modified version of the optical lever method. A bare microcantilever die, without cells, was placed in the stimulation chamber. The laser was focused on one of the microcantilevers and the PD was adjusted so that the laser fell on the diode surface. Using a digital volt meter to monitor the output voltage, the PD was adjusted so that the voltage being read was less than −7 volts. The PD was then moved vertically in 5 mm increments and the voltage recorded at each position. The results were plotted in Excel and a linear regression line was fitted to the linear region of the calibration curve, which was the region between −5 and 5 volts. The slope of this region was the detector sensitivity (y detector). This value was used to calculate the angle, 0, of the deflection at the end of the microcantilever using the equation (Equation 1):

$$\theta = \frac{y_{measured}}{2\cos(\varphi) l \times y_{detector}} \quad (1)$$

where, y measured is the voltage measured from the PD, φ, is the angle of the detector to normal, and 1, is the path length of the reflected laser beam.

Because of the large variability in the spring constants, cantilevers have to be further calibrated on an individual basis when used for precision force measurements. This variability is most likely caused by variations in thickness of the cantilever. Variability in the length and width is often quite small because typical lateral resolution in photolithography is on the submicrometer scale. For nominal spring constants greater than 0.1 N/m, the calibrated load displacement transducer of a nanoindenter can be used to measure the spring constant of each cantilever in an array. Measuring the resonance frequency of individual cantilevers and applying it to Sader's equation can provide detailed spring constants.

Multielectrode Extracellular Recordings

The cardiac myocytes were cultured on patterned metal MEAs (Planar 10 μm electrodes, 200 μm separation. Multichannel-systems). A 60 channel amplifier (MEA1040, Multichannel-systems) was used to record electrical activity from the spontaneously beating cardiac cells. The same electrodes were also used for stimulation utilizing a stimulus generator (STG 1002, Multichannel systems). The cells were stimulated utilizing 500 mV, 1 ms wide bipolar pulses at 2 Hz. The recording medium was the same as the plating medium with the pH adjusted to 7.3 using HEPES buffer. After a 30 minute incubation period, APs were detected and recorded using built in functions of the Multichannel System software. For drug experiments, 50 μM 1-Heptanol (Gibco/Invitrogen) was added to the bathing medium and recordings were performed before and 15 minutes after drug administration with additional recordings done at 15 minute intervals. For Sparfloxacin (Sigma-aldrich), 2 μM of the drug was added to the recording medium and recordings were taken in 15 minute intervals before and after drug administration. The data was further analyzed using software written using Matlab and Clampfit (Axon instruments).

Cell Culture

The serum-free medium comprised 100 mL Ultraculture medium (Bio Whittaker Cambrex) supplemented with 10 mL B27, 1 mL L-glutamine (Gibco/Invitrogen), 1 mL Penicillin Streptomycin, 0.375 g dextrose (Fisher Scientific) in 800 μL water, 1 mL non-essential amino acids and 1 mL of Hepes buffer (Gibco/Invitrogen) (Sathaye et al., 2006). Additional growth factors were also added to improve cell survival in the serum-free conditions. They included 0.1 μg/mL of L-thyroxine, 10 ng/mL of epidermal growth factor (Sigma-Aldrich) and 0.5 μg/mL of hydrocortisone (BD biosciences). Cells were plated at a density of 1000 cells/mm$^2$ on the MEAs. The medium was changed 24 hours after plating. Subsequent changing of the medium was performed every third day.

Human embryonic stem cell derived cell types including cardiomyocytes have been generated for pharmacology testing and toxicology screening. For example, GE markets cardiac myocytes. Before product release, each lot is highly characterized by flow cytometry, subcellular imaging, and electrophysiology. Each lot is demonstrated to express Gata4. Nkx2.5, MYH6/7, troponin I, aMHC and a-actinin, and negative for Oct4, TRA-1-81 and TRA-1-60. The cardiomyocyte population comprises ventricular, atrial, and nodal subtypes and have been documented to have an adult phenotype.

Immunostaining

Patterned cardiac myocytes can be immunostained. In a set of experiments, the patterned cardiac myocytes were immunostained for F-Actin with Rhodamine Phalloidin (Invitrogen, R415) using a protocol provided by the company. Briefly, the cells were washed with PBS and fixed using 3% Formaldehyde. The coverslips were extracted with 0.1 mL Triton X®. The staining solution (with 1% Bovine Serum Albumin to prevent background staining) was added at a dilution of 1:40 in PBS and coverslips were incubated for 30 minutes. Imaging was done using confocal microscopy.

Figure 15:
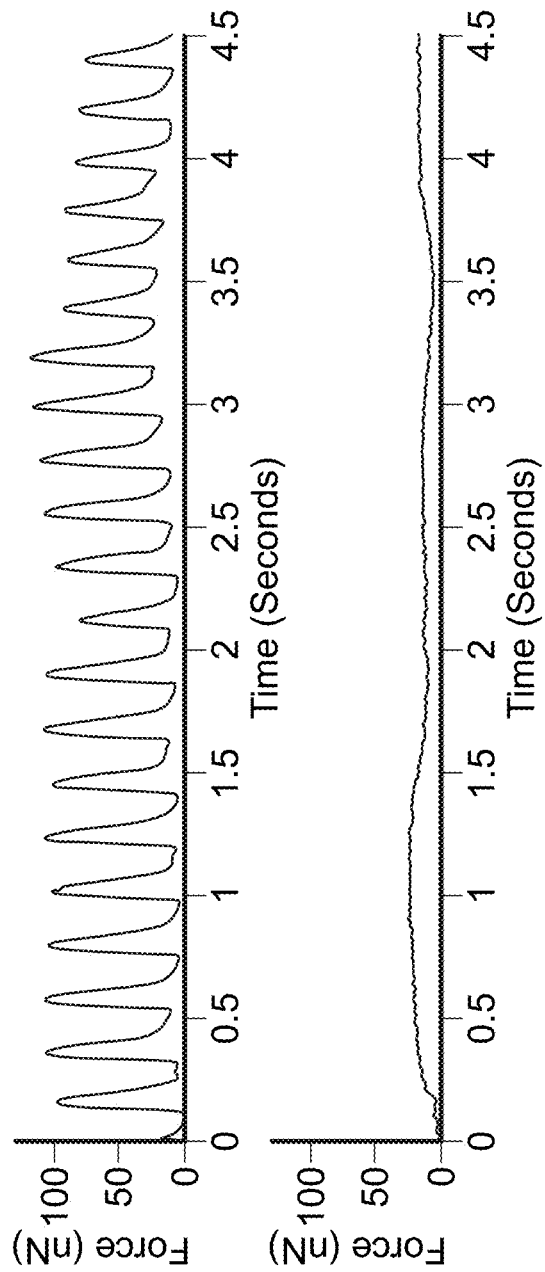
FIG. 15 shows characterization of myotube-motoneuron functional scanning system. Addition of motoneurons to this assay system facilitates assessment of neuromuscular synapse formation in vitro using neuronal stimulated, such as glutamate, and neuromuscular junction inhibitors, such as D-tubocurarine. Functional contractile recordings made in response to treatment of co-culture system with glutamate (top trace) and treatment with glutamate and D-tubocurarine (bottom trace).
Figure 16A:
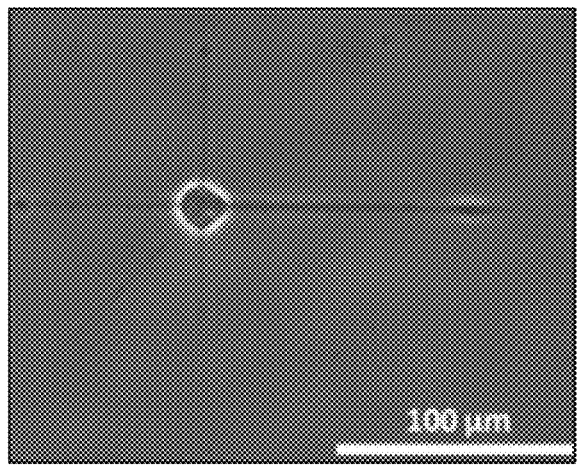
FIGS. 16A-16D show demonstration of chemical patterning of culture surfaces to control neuronal development in vitro. Treatment of surfaces with cytophilic and cytophobic surface modifications allows for a high degree of control over cellular location within in vitro culture systems. Such patterning also facilitates dictation of cellular outgrowth direction, allowing investigators to influence when and how different cell population interact in culture.
Figure 16B:
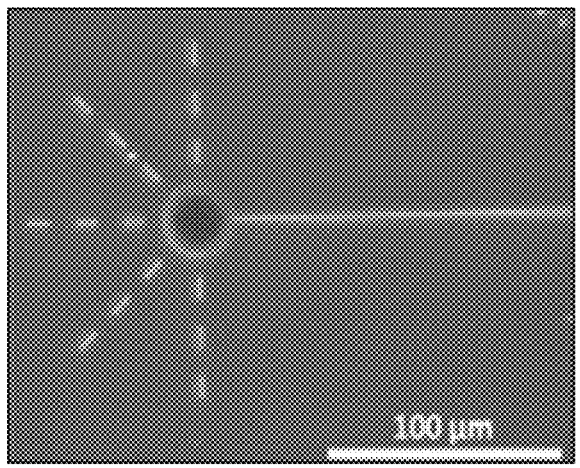
Figure 16C:
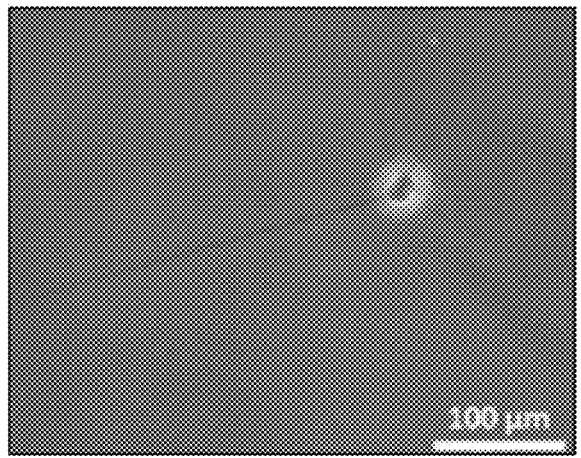
Figure 16D:
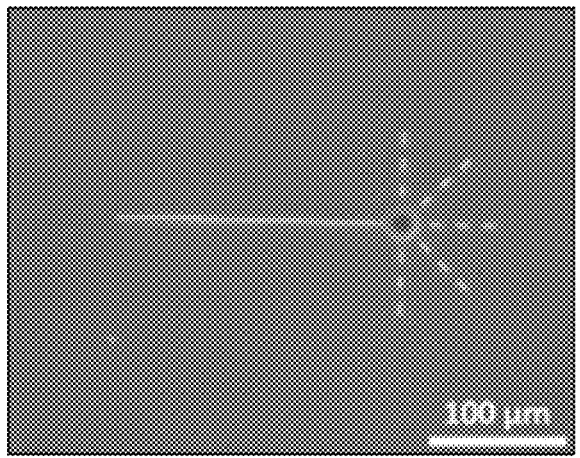

Example 4—Data for FIG. 15

Using the cantilevers and muscle cell culturing conditions of Example 2, motoneuron and muscle cells (myotubes) were co-cultured. Spinal cords were dissected from E15 fetuses and the dorsal horn carefully removed using a fine surgical blade (Fine Science Tools, Foster City, CA). The isolated cords were transferred to a 0.25% trypsin solution and incubated for 12 minutes. The tissue was then carefully triturated to dissociate it into a single cell suspension using a P1000 pipette tip. The resulting cell suspension was layered onto a 4 mL step gradient (Optiprep (Sigma-Aldrich. St. Louis, MO) diluted 0.505:0.495 (v/v) with Hibernate E (Brain Bits)+GlutaMAX™ (Life Technologies)+AB/AM+B27 (Life Technologies) and then made up to 15%, 20%, 25% and 35% solutions (v/v) in Hibernate E+AB/AM+B27 and spun at 200 g for 15 minutes at 4° C. Motoneurons, with large somas, formed the upper-most band and were collected using a P1000 pipette before being spun again at 200 g for 5 minutes. The resulting cell pellet was then re-suspended in a co-culture medium described in Table 2. This co-culture medium has been used to generate ventral horn cultures, enriched for motoneurons (Das et al., 2010).

TABLE 2

Components of Co-Culture Medium

| Component | Concentration | Company (Catalog No.) |
| --- | --- | --- |
| Neurobasal medium | N/A | Life Technologies (21103-049) |
| B27 (50x) | 1x | Life Technologies (17504044) |
| Glutamax (100x) | 1x | (35050061) |
| Glial-Derived Neurotrophic Factor | 10 ng/ml | Cell sciences (CRG400B) |
| Brain-Derived Neurotrophic Factor | 20 ng/mL | Cell sciences (CRB600B) |
| Ciliary neurotrophic factor | 5 ng/mL | Cell sciences (CRC400A) |
| Insulin-like growth factor-1 | 25 ng/mL | Sigma (I2656) |
| Neurotrophin-3 | 20 ng/mL | Cell sciences (CRN500B) |
| Neurotrophin-4 | 20 ng/mL | Cell sciences (CRN501B) |
| Mouse laminin | 1 µg/mL | Life Technologies (23017-015) |
| cAMP | 1 µM | Sigma (A9501) |

Muscle cultures, maintained for 3 days in vitro in muscle differentiation medium, were aspirated and were fed with co-culture medium. Isolated ventral horn cells were then plated directly on top of the cultured muscle cells at a density of 250 cells/mm$^2$. Co-cultures were maintained in the co-culture medium for another 7 days in vitro, with half the medium replaced every 2-3 days. Following 7 days in co-culture, the growth factors in the medium were slowly diluted out by replacing half the medium every 2 days with NBActiv4+1% AB/AM. Co-cultures were analyzed for evidence of neuromuscular transmission following 13-14 days in vitro (i.e., a total culture time of 20-21 days in vitro).

Muscle-only control cultures were established in parallel to all co-cultures examined. These cultures were subjected to identical culture parameters minus the plating of ventral horn cells after 7 days in vitro.

Electrophysiological Recordings

After 11-13 days in vitro, electrophysiological properties of ventral horn motoneurons were investigated using whole-cell patch-clamp recording techniques. Glass coverslips with cultured ventral horn cells were transferred to a recording chamber located on the stage of a Zeiss Axioscope 2FS Plus upright microscope. Motoneurons were identified visually under an infrared differential interference contrast (DIC) video-microscope. The largest multipolar cells (15-20 µm diameters) with bright somas were identified as motoneurons. Borosilicate glass patch pipettes (BF 150-86-10; Sutter Instrument Company) with a resistance of 6-10 MΩ were made using a Sutter P97 pipette puller (Sutter Instrument Company). Current-clamp and voltage-clamp recordings were made using a Multiclamp 700A amplifier (Axon instruments). The pipette (intracellular) solution contained 1 mM EGTA, 140 mM K-gluconate, 2 mM MgCl$_2$, 2 mM Na$_2$ATP and 10 mM HEPES (pH 7.2). NBActiv4 medium plus 10 mM HEPES (pH 7.2) was used as the extracellular solution.

After the formation of a giga-ohm seal and membrane puncture, the cell capacitance was compensated. Signals were filtered at 3 kHz and sampled at 20 kHz using a Digidata 1322A interface (Axon Instruments). Data recording and analysis were performed with pClamp8 software (Axon Instruments). Membrane potentials were corrected by subtraction of a 15 mV tip potential, which was calculated using Axon's pClamp8 program. Depolarization-evoked inward and outward currents were examined in voltage-clamp mode. Depolarization-evoked action potentials were examined in current-clamp mode and induced using 1 second depolarizing current injections from a −70 mV holding potential. Action potentials elicited in response to 200 µM glutamate (an excitatory neurotransmitter) (Sigma-Aldrich) injection into the extracellular solution were likewise measured in current-clamp mode from a −70 mV holding potential.

Measurement of Myotube Contraction in Response to Neuronal Stimulation

Broad field electrical stimulation was first used to verify the contractile ability of the cultured myotubes. Cultures were subjected to a 3 V, 40 ms pulse at a frequency of 1 Hz, and the cantilevers were scanned for 5 seconds each to identify those with active myotubes. Across all experimental conditions, a successful contractile response was taken as any peak equal to or larger than 0.1 V.

The electrical stimulus was then switched off and the active cantilevers were individually scanned again in order to observe the rate of spontaneous contraction. This condition was followed by bath application of 200 µM glutamate to stimulate motoneuron firing, and the cantilevers were again scanned for evidence of contractile activity. A second application of glutamate was made following addition of 12.5 µM D-tubocurarine (Sigma-Aldrich) to block neuromuscular transmission. The cantilevers were again scanned for contractile activity following this treatment. Finally, cantilevers were subjected to the same broad-field electrical stimulation as was used initially and scanned for contractile activity to verify that the treatments had not destroyed the contractile capability of the myotube or caused the cells to detach.

An immunocytochemical stain of a co-culture cantilever illustrated close association of pre-synaptic structures where cells stained green for Synaptic Vesicle Protein 2 and post-synaptic structures stained red for acetylcholine receptors. The path of the infiltrating neurite was also illustrated via staining for P-III-Tubulin (blue).

Example 5—Chemical Patterning of Culture Surfaces to Control Neuronal Development In Vitro (FIG. 16)

Surfaces that resist cell adhesion generally are non-polar and either strongly hydrophobic, such as hydrocarbon or perfluorinated surfaces, or strongly hydrophilic, such as polyethylene glycol (PEG). Surfaces that tend to pro-mote cell adhesion usually consist of polar, hydrophilic molecules. Aminated molecules, for example, alkylsilane (3-trimethoxysilyl propyl) diethylenetriamine (DETA) and aminopropyl triethoxysilane, are considered to be strongly cytophilic and promote the growth and differentiation of cells. Alkylsilane self-assembled monolayers (SAMs) are a class of compounds that are used extensively for modifying the surface properties of silica substrates (silicon, glass, etc.). These compounds come in a variety of chemistries that are used for many applications and are often utilized to modulate the biological interactions of silica substrates with biological materials. Work has shown that it is possible to pattern the aminated alkylsilane DETA using deep-ultraviolet (DUV) photolithography. Using DUV, SAMs were exposed to intense ultraviolet light from an ArF excimer laser (emission wavelength 193 nm). Upon exposure the SAM underwent a photochemical reaction that cleaved the carbon-nitrogen bonds within the molecule, thereby removing the cytophilic surface coating. The ablated regions were then rederivitized with a perfluorinated silane to create a surface that resisted cell adhesion.

Silica substrates, such as glass and/or silicon wafers, were cleaned using serial acid baths and then were coated with a PEG-terminated silane by a modified protocol from Papra et al. The PEG silane used for these experiments 2-[methoxy-poly(ethyleneoxy)propyl]trimethoxysilane (PEGSi) (Gelest, Tullytown, PA) was added to toluene to a final concentration of 0.1% by volume. The PEGSi-toluene solution was removed from the glovebox and brought into a chemical fume hood. Concentrated HCl was added to a final volume of 0.08% (0.8 ml HCl/L) and the solution briefly stirred. The cleaned silica substrates were removed from the oven and allowed to cool to room temperature before incubation in the PEGSi-toluene solution for 1 h at room temperature. The reaction vessel was loosely covered to prevent excessive exposure. After 1 h the samples were removed and rinsed in serial washes of toluene (one time), ethanol (two times), and diH2O (one time). The washed samples were blown dry under a stream of ultrapure nitrogen and were used immediately or stored in a desiccator until needed.

PEGSi modified silica substrates were patterned using DUV photolithography. Samples were placed on the stage of the mask aligner under a 5×5 in.2 chrome plated photomask, which contained the pattern to be ablated. The masks were written in dark-field polarity such that the areas corresponding to the ablated pattern were transparent and the remaining areas were opaque. The substrates were then exposed to 193 nm ultraviolet laser light for 15-120 s with a pulse intensity of 200 mJ/pulse and a frequency of 10 Hz. After ablation the samples were removed from the aligner stage and stored for subsequent processing. After ablation, the patterned PEGSi substrates were back-filled with DETA. Fresh distilled toluene was transferred into a Pyrex bottle that had been dried in an 80° C. oven to re-move excess surface water. Dry nitrogen was used to replace the air in the remaining volume of the bottle to minimize free oxygen. The bottle was sealed and transferred into an MBraun glovebox. DETA was added to the toluene to a final concentration of 0.1% (vol:vol). The DETA-toluene solution was removed from the glovebox and transferred to a Pyrex beaker, and the samples were immersed in the solution. To drive the reaction forward the solution was gently heated to no more than 65° C. Optimal reaction time was analyzed for these conditions by incubating the samples for 10, 20, and 30 min (n=3). After reaction with DETA the samples were allowed to cool to room temperature, washed three times with dry toluene, and heated to 65° C. for additional 30 min in fresh toluene. The resulting samples were analyzed by XPS and contact angle goniometry.

Embryonic Motoneuron

Spinal motoneurons were purified from ventral cords of embryonic day 14 (El 4) rat pups. Briefly, rats were euthanized by $CO_2$ asphyxiation. Ventral spinal cells from the embryo were collected in cold Hibernate E (BrainBits, Springfield, IL, SA)/GutaMAX/antibiotic-antimycotic/B27 (Invitrogen, Carlsbad, CA). The cells were dissociated with 0.05% trypsin-EDTA (Invitrogen, Carlsbad, CA) treatment. The dissociated cells were layered over a 4 mL step gradient (Optipep diluted 1:1 (vol/vol) with Hibernate E/GlutaMAX/antibiotic-antimycotic/B27 and then made to 15%, 20%, 25%, and 35% (vol:vol) in Hibernate E/GlutaMAX/antibiotic-antimycotic/B27 followed by centrifugation for 15 min, using 800 g, at 4° C. This was a modification from the previously described protocols due to nonavailability of metrizamide. After centrifugation, four bands of cells were obtained, the topmost of which contained the motoneurons. These cells were further purified by immunopanning. The motoneurons were selected using the immune interaction between the motoneurons and the MAB192 antibody (1:2 dilution, ICN Biomedicals, Akron, OH) coated on the dishes. The antibody recognized the low affinity nerve growth factor (NGF) receptor that is only expressed by ventral motoneurons at this age.

Embryonic Hippocampal Neuron

Rat pups, at embryonic day 18, were dissected from timed pregnant rats that were euthanized using $CO_2$ asphyxiation. Embryos were collected in ice cold Hibernate E/B27/Glutamax™/antibiotic-antimycotic. The hippocampi were isolated from the embryonic brain and collected in a tube containing 1 mL of Hibernate E/B27/Glutamax™/antibiotic-antimycotic. The embryonic hippocampal neurons were obtained by triturating the tissue using a Pasteur pipette. The 1 mL cell suspension was layered over a 4 ml step gradient (Optipep diluted 1:1 (vol:vol) with Hibernate E/GlutaMAX/antibiotic-antimycotic/B27 and then made to 15%, 20%, 25% and 35% (v/v) in Hibernate E/GlutaMAX™/antibiotic-antimycotic/B27) followed by centrifugation for 15 min, using 800 g, at 4° C. This additional step enabled the removal of debris that arises during dissection from the damaged cells. After centrifugation, one strong band of cells was obtained at the top. The pyramidal hippocampal neurons constituted this band and were identified due to their large somas. The cells were resuspended in culture medium (neurobasal/B27/Glutamax/antibiotic-antimycotic) and plated at a density of 75 cells/mm. Half of the medium was changed after every 3-4 days.

As shown in FIG. 16, the cells were confined to the DETA regions of the patterns and adhered to the patterns for the duration of the culture. Embryonic motoneurons were cultured on the patterned PEGSi-DETA surfaces. Primarily the cell bodies that adhered to the DETA region, while processes were seen to extend across the PEGSi regions to contact cells on other DETA regions. It was common to see cells extend processes onto the PEGSi while the motoneuron cell bodies remained attached to the DETA regions. This indicates that while the PEG repels adhesion of the cell soma, it is not completely repulsive to the attachment of neuronal processes. Embryonic hippocampal neurons were cultured on PEGSi-DETA patterns shown in FIGS. 16A and 16C. FIGS. 16B and 16D show results from metallizing the patterned surface. Cells adhered to the pattern and cell bodies were confined to the circular somal adhesion sites and axonal processes extended outwardly from there. For more detail, see patent applications incorporated by reference herein, and "Direct Patterning of coplanar polyethylene glycol alkylsilane monolayers by deep-ultraviolet photolithography as a general method for high fidelity, long-term cell patterning and culture, Wilson et al., 2011 (J. Vac. Sci. Technol.) 29(2):021020-2 to 021020-10.

Figure 17A:
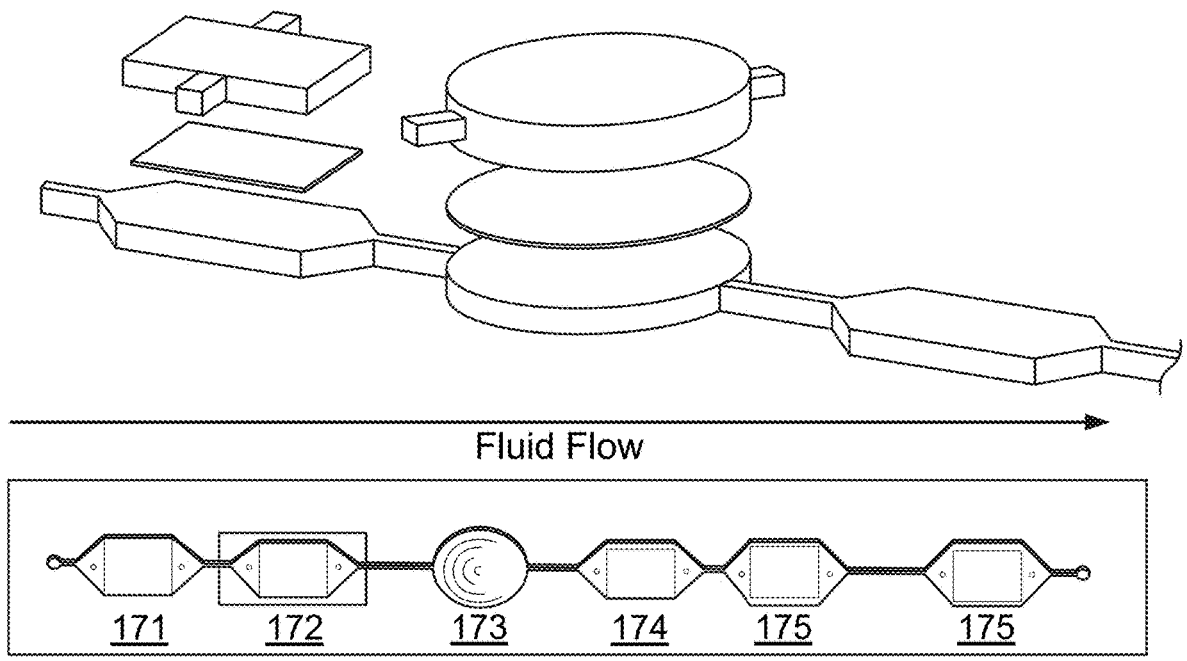
FIGS. 17A-17B show functional layouts and measurements of gas transfer using a lung-on-a-chip functional system.
Figure 17B:
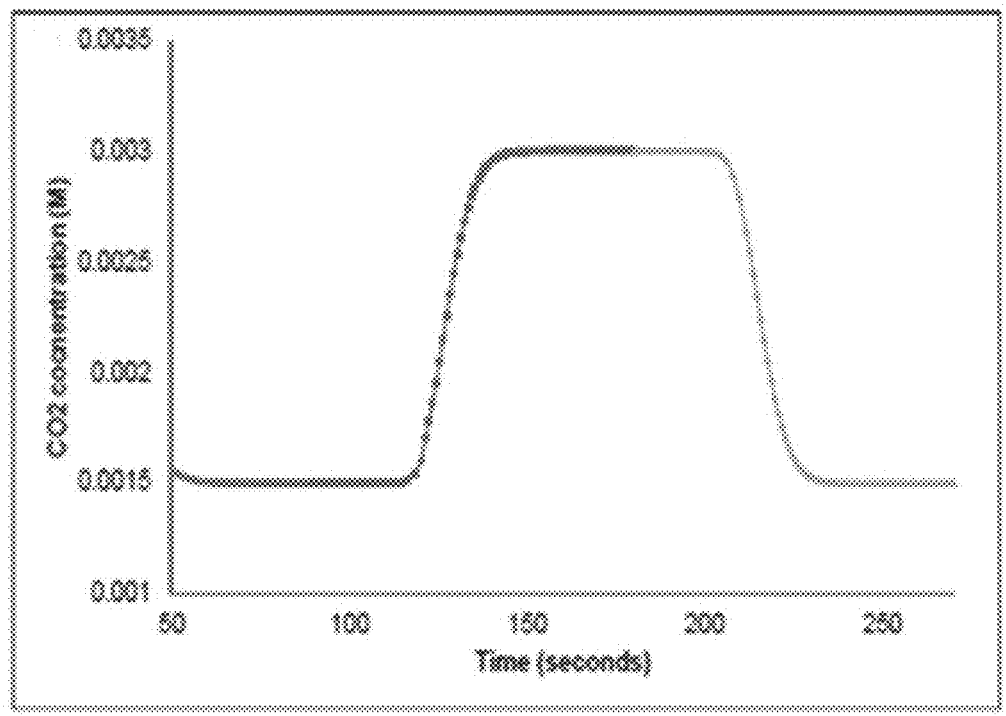

Example 6—Lung on a Chip (FIG. 17)

The design shown in FIG. 17 produces the liquid side of a lung-on-a chip device with plug flow, which provides a function component capable of creating a physiological environment for cells at the air-liquid interface on commercially available membrane supports and enables measurement of changes in gas transport through cell layers. Such a lung component may be one of a plurality of components of a cell culture analog system of the present invention.

Silicon-based microfluidic technology was used to create a bioreactor in which liquid that enters the model alveolus with a gas composition similar to the gas composition of venous blood exits the chamber with a gas composition similar to that of arterial blood. The alveolar chamber is designed so that the gas composition of the liquid reaches arterial values just before the liquid exits the chamber. The chamber is designed so that liquid flowing through different parts of the chamber experiences similar residence time within the chambers and the gas concentration changes in measurable values. This approximates plug flow. Details for construction of a lung component as provided in "Design Optimization of Liquid-Phase Flow Patterns for Microfabricated Lung on a Chip," Long et al., Annals of Biomedical Engineering, 40(6): 1255-67 (2012), which is herein incorporated in its entirety.

Example 7—Investigation of a Functional 4-Organ Body-on-a-Chip System with Common Serum-Free Medium This example demonstrates a function four component system in a human-based system composed of key organs affected by toxic agents for 14 days in a serum-free, defined culture system under circulation. The four human organ systems on one chip are liver, cardiac, motoneurons and muscle. These four components each comprising one of the four cell types are co-cultured in the same, serum free defined media in a single functional unit. Circulation is modeled in silico and achieved experimentally using the cell analog system comprising four components as described. Functional readouts for electrical activity (cardiac and motoneuron) and force generation (cardiac and skeletal muscle) are made. Liver cells are monitored for P450 enzymatic activity, albumin and urea. Three to nine compounds are tested for organ specific, dose related toxicity.

The co-culture of four primary human cell types in microfluidic components in a system which mimics physiological conditions calculated by in silico modeling. Cell constructs should all be viable for 7 days and functional (force generation, electrical activity and enzymatic activity). Dose response curves for three to nine compounds show effects on the various functional readouts described above as well as 14 day survival Shuler has previously constructed platform systems with up to 5 chambers that support multiple organ system constructs based on single cells. Integration of the four components of the present system requires a common blood surrogate (media) that can sustain activity of all biological modules (components) for at least 14 days. Optical and electrophysiological measurements will be done on the chip. Biomarkers will be measured with microanalytical techniques using small amounts of fluid (e.g., 50 µL). In silico models of the system will be used to translate results into a form that predicts human response. Key liver markers (cytochrome P450s) for metabolism will be maintained for at least 14 days under a flow system.

Organ Components: Cardiac: The heart primary functions, electrical and force generation are measured and then reconstruct the data to give an accurate representation of organ function. Incorporation of a functional cardiac system enables the measurement of rhythm generation conduction and QT interval in an in vitro system based on patterned cardiac myocytes. The in vitro electrophysiological measurement parameters are analogous to the parameters used in the SCREENIT scoring system. According to recent literature, these parameters have high predictive value for cardiac side effects. Cardiac contraction force generation is measured by cardiac myocyte integration on a microcantilever system, similar to the cantilevers described herein for measuring force dynamics of muscle fibers. Parameters to be monitored will be contractile force, speed of contraction and time to relaxation, muscle fatigue and muscle recovery. The mechanical device and the read out electronics are implemented in the same integrated circuit. CDI iPSC derived cardiomyocytes are used in the project.

PNS component: Motoneuron (MN) electrical activity and muscle force determination are monitored separately in the system with MEA technology and cantilever bending for muscle contraction using laser based readouts, respectively. In addition, human-based functional neuromuscular junctions (NMJ) are used that can be monitored by controlled stimulation of MN. Contracting myotubes that can be blocked by curare are considered functional NMJs. All necessary techniques are well developed and described herein and include optically transparent MEA system (surface patterning, cell culture, recording and analysis), microcantilever force determination (cell culture, recording) and human NMJ formation.

Liver: A tissue engineered models of the liver using primary and progenitor cells from human livers are used, but iPSC derived hepatocytes are also utilized. The resulting construct has been shown to be active for many weeks of sustained liver function. This component can be readily integrated on the platform in a liver compartment allowing the development of models of oral drug absorption and first pass metabolism.

Blood Surrogate: Medium will be recirculated that is compatible with all cell types and mimics the ability of blood to transport chemicals. A defined common serum-free medium that supports a liver cell line, primary cardiomyocytes, neurons and muscle, with survival and function maintained for over two weeks. It may be optimized from the chemically defined medium to mimic the transport properties of blood for more hydrophobic compounds, if necessary.

Compound Testing: toxicity of compounds is assessed for the components and compared to data generated from pre-clinical and clinical trials. Compound concentration in the medium will be monitored by taking aliquots that are then analyzed by HPLC-MSMS technology Materials and Methods. The MEA and cantilever systems are fabricated from silicon substrates and may be monolithic, on separate chips or a combination thereof. The liver chamber will be fabricated from PDMS or similar polymer, in addition, the housing and interconnects will be fabricated using polymer-based materials. Cell culture techniques are used.

REFERENCES

Agarwal A, et al. Microfluidic heart on a chip for higher throughput pharmacological studies. Lab on a chip, d (2013).
Bellas E. et al. In vitro 3D full-thickness skin-equivalent tissue model using silk and collagen biomaterials. Macromolecular bioscience 12, 1627-1636 (2012).
Bers D M. Cardiac excitation-contraction coupling. Nature 2002; 415(6868): 198-205.
Carlsson L. In vitro and in vivo models for testing arrhythmogenesis in drugs. Journal of Internal Medicine 2006; 259(1): 70-80.
Dakhel Y. et al. Erythomycin potentiates pr interval prolonging effect of verapamil in the rat: A pharmacodynamic drug interaction. Toxicol Appl Phamacol 2006; 214: 24-29.
Das M, et al. A defined long-term in vitro tissue engineered model of neuromuscular junctions. Biomaterials 2010; 31: 4880-4888.
Das M, et al. Differentiation of skeletal muscle and integration of myotubes with silicon microstructures using serum-free medium and a synthetic silane substrate. Nature Protocols 2007; 2(7): 1795-1801.
Das M. et al. Embryonic motor neuron-skeletal muscle co-culture in a defined system. Neuroscience 2007; 146: 481-488
Das M, et al. Long-term culture of embryonic rat cardiomyocytes on an organosilane surface in a serum free medium. Biomaterials 2004; 25(25): 5643-5647.
Das M, et al. Skeletal muscle tissue engineering: A maturation model promoting long-term survival of myotubes, structural development of the excitation-contraction coupling apparatus and neonatal myosin heavy chain expression. Biomaterials 30, 5392-5402 (2009).
Das M, et al. Skeletal muscle tissue engineering: An improved model promoting long term survival of myotubes, structural development of e-c coupling apparatus and neonatal myosin heavy chain (mhc) expression. Biomaterials 2009; 30: 5392-5402.
Das M, et al. Temporal neurotransmitter conditioning restores the functional activity of adult spinal cord neurons in long-term culture. Experimental Neurology 2008; 209: 171-180
Das M, et al. A defined long-term in vitro tissue engineered model of neuromuscular junctions. Biomaterials 31, 4880-4888 (2010).
Das, M. et al. A defined system to allow skeletal muscle differentiation and subsequent integration with silicon microstructures. Biomaterials 27, 4374-4380 (2006).
Das M. et al. Electrophysiological and morphological characterization of rat embryonic motoneurons in a defined system. Biotechnology progress 19, 1756-1761, (2003).
Davis, H. et al. Rat Cortical Oligodendrocyte-Embryonic Motoneuron Co-Culture: An Axon-Oligodendrocyte Interaction Model. Journal biomaterials tissue engine 2, 206-214 (2012).
Dhir V, et al. Patterning of diverse mammalian cell types in serum free medium with photoablation. Biotechnol Prog 2009; 25(2): 594-603.
Edwards D, et al. Addition of glutamate to serum-free culture promotes recovery of electrical activity in adult hippocampal neurons in vitro. J Neuroscience meth 190, 155-163 (2010).
Guo X F, et al. Characterization of a human fetal spinal cord stem cell line nsi-566rsc and its induction to functional motoneurons. Tissue Engineering and Regenerative Medicine 2010; 4: 181-193.
Guo X F, et al. Nmj formation between human stem cell derived motoneurons and rat skeletal muscle in a defined system. Tissue Engineering: Part C 2010; 16(6): 1347-1355.
Guo X, et al. Neuromuscular junction formation between human stem cell-derived motoneurons and human skeletal muscle in a defined system. Biomaterials 32, 9602-9611 (2011).
Guo X, et al. Characterization of a human fetal spinal cord stem cell line, NSI-566RSC, and its induction to functional motoneurons. Journal of Tissue Engineering and Regenerative Medicine 4, 181-193 (2010).
Guo X, et al. Derivation of sensory neurons and neural crest stem cells from human neural progenitor hNP 1. Biomaterials 34, 4418-4427 (2013).
Hughes B. 2007 fda drug approvals: A year of flux specialty products dominate innovative drug approvals—a trend that looks set to continue. Nature Reviews Drug Discovery 2008; 7: 107-109.
Huh, D. et al. Reconstituting organ-level lung functions on a chip. Science 328, 1662-1668 (2010).
Jung D R. et al. Cell-based sensor microelectrode array characterized by imaging x-ray photoelectron spectroscopy, scanning electron microscopy, impedance measurements, and extracellular recordings. J Vac Sci Technol A 1998; 16(3): 1183-1188.
Kang J H, et al. In vitro 3D model for human vascularized adipose tissue. Tissue Eng Part A 15, 2227-2236 (2009).
Kim C, et al. Non-cardiomyocytes influence the electrophysiological maturation of human embryonic stem cell-derived cardiomyocytes during differentiation. Stem cells and development 2010; 19(6): 783-795.
Kita-Matsuo H, et al. Lentiviral vectors and protocols for creation of stable hesc lines for fluorescent tracking and drug resistance selection of cardiomyocytes. PLoS ONE 2009; 4(4): e5046.
Lawrence C L, et al. Nonclinical proarrhythmia models: Predicting torsades de pointes. Journal of Pharmacological and Toxicological Methods 2005; 52(1): 46-59.
Lipsett M A, et al. Acinar plasticity: development of a novel in vitro model to study human acinar-to-duct-to-islet differentiation. Pancreas 34, 452-457 (2007).
Liu W P, et al. Enantioselectivity in environmental safety of current chiral insecticides. Proc Natl Acad Sci USA 2005; 102(3): 701-706.
Lund A E. et al. Dose-dependent interaction of the pyrethroid isomers with sodium-channels of squid axon-membranes. Neurotoxicology 1982; 3(1): 11-24.
Maduell F. Hemodiafiltration. Hemodial Int 2005; 9(1): 47-55.

Mahler G J, et al. Characterization of a gastrointestinal tract microscale cell culture analog used to predict drug toxicity. Biotechnol Bioeng 2009; 104(1): 193-205.

Mahler G J, et al. Characterization of caco-2 and ht29-mtx co-cultures in an in vitro digestion/cell culture model used to predict iron bioavailability. J Nutr Biochem 2009; 20(7): 494-502.

Marona H R N, et al. Determination of sparfloxcin and its degradation products by hplc-pda. J Antimicrob Chemother 1999; 44: 301-302.

McAuliffe G J, et al. Development of a gastrointestinal tract microscale cell culture analog to predict drug transport. Mol Cell Bioengr 2008; 5(2): 119-132.

Meyer T. et al. Qt-screen: High-throughput cardiac safety pharmacology by extracellular electrophysiology on primary cardiac myocytes. Assay and Drug Development Technologies 2004; 2(5): 507-514.

Mohan D K, et al. Toxin detection based on action potential shape analysis using a realistic mathematical model of differentiated ng108-15 cells. BiosensBioelectron 2006; 21: 1804-1811.

Molnar P. et al. Photolithographic patterning of c2c12 myotubes using vitronectin as growth substrate in serum-free medium. Biotechnol Prog 2007; 23(1): 265-268.

Molnar P, et al. Synaptic connectivity in engineered neuronal networks, in Patch-clamp methods and protocols. Molnar P and Hickman J J, Editors. 2007, Humana Press: New York.

Mufti N A. et al. Different in vitro systems affect cyp1a1 activity in response to 2,3,7,8-tetrachlorodibenzo-p-dioxin. Toxicol in vitro 1998; 12: 259-272.

Nakamura Y. et al. The in vitro metabolism of a pyrethroid insecticide, permethrin, and its hydrolysis products in rats. Toxicol Appl Pharmacol 2007; 235: 176-184.

Natarajan A, et al. Engineered In vitro Feed-Forward Networks. J Biotechnol Biomater 3, 2(2013).

Natarajan A. et al. Multielectrode recordings of cardiac action potentials as a high throughput method to evaluate pesticide toxicity. Toxicol In vitro 2006; 20(3): 375-381.

Natarajan A, et al. Patterned cardiomyocytes on microelectrode arrays as a functional, high information content drug screening platform. Biomaterials 2011; in press.

Natarajan, A. et al. Patterned cardiomyocytes on microelectrode arrays as a functional, high information content drug screening platform. Biomaterials 32, 4267-4274 (2011).

Oh T-i, et al. Real-time fluorescence detection of multiple microscale cell culture analog devices in situ. Cytometry Part A 2007; 71 A: 857-865.

Pointer C, P et al. Ht29-mtx and caco-2ltc7 monolayers as predictive models for human intestinal absorption: Role of mucus layer. J PharmSci 2001; 90: 1608-1619.

Rumsey J W, et al. Node of ranvier formation on motoneurons in vitro. Biomaterials 2009; 30: 3567-3572.

Rumsey J W, et al. Tissue engineering the mechanosensory circuit of the stretch reflex arc: Sensory neuron innervation of intrafusal muscle fibers. Biomaterials 31, 8218-8227 (2010).

Schaffner A E, et al. Investigation of the factors necessary for growth of hippocampal neurons in a defined system. J Neurosci Methods 1995; 62(1-2): 111-9.

Schaffner A E. et al. Investigation of the factors necessary for growth of hippocampal neurons in a defined system. Journal of neuroscience methods 62, 111-119 (1995).

Scollon E J, et al. In vitro metabolism of pyrethroid pesticides by rat and human hepatic microsomes and cytochrome p450 isoforms. Drug Metabolism and Disposition 2009; 37(1): 221-228.

Selivanova O M, et al. Compact globular structure of thermos thermophilus ribosomal protein si in solution. J BiolChem 2003; 278(38): 36311-36314.

Sin A, et al. The design and fabrication of three-chamber microscale cell culture analog devices with integrated dissolved oxygen sensors. Biotechnol Prog 2004; 20: 338-345.

Subramanian, B. et al. Tissue-engineered three-dimensional in vitro models for normal and diseased kidney. Tissue Eng Part A 16, 2821-2831 (2010).

Sung J H, et al. A micro cell culture analog with 3-d hydrogel culture of multiple cell lines to assess metabolism-dependent cytotoxicity of anti-cancer drugs. Lab Chip 2009; 9(10): 1385-1394.

Sung J H, et al. A microfluidic device for a pharmacokinetic-pharmacodynamic (pk-pd) model on a chip. Lab Chip 2010; 10: 446-455.

Sung J H. et al. Fluorescence optical detection in situ for real time monitoring of enzymatic activity of liver cells in multiple microfluidic devices. Biotechnol Bioeng 2009; 104: 516-525.

Sung J H, et al. Prevention of air bubble formation in a microfluidic perfusion cell culture system using a microscale bubble trap. Biomed Microdevices 2009; 11: 731-738.

Sung J H, et al. Microfabricated mammalian organ systems and their integration into models of whole animals and humans. Lab on a chip 13, 1201-1212 (2013).

Suter W. Predictive value of in vitro safety studies. Current Opinion in Chemical Biology 2006; 10(4): 362-366.

Sutton N M, et al Clinical effects and outcome of feline permethrin spot-on poisonings reported to the veterinary poisons information service (vpis), london. J Feline Med & Surgery 2007; 9: 335-339.

Swynghedauw B. Molecular mechanisms of myocardial remodeling. Physiol Rev 1999; 79(1): 215-262.

Takagishi Y, et al. Species-specific difference in distribution of voltage-gated 1-type ca2+ channels of cardiac myocytes. Am J Physiol Cell Physiol 2000; 279(6): C1963-1969.

Tatosian D A, et al. A novel system for evaluation of drug mixtures for potential efficacy in treating multidrug resistant cancers. Biotechnol Bioeng 2009; 103(1): 187-198.

van der Valk J, et al. Optimization of chemically defined cell culture media-replacing fetal bovine serum in mammalian in vitro methods. Toxicology in vitro: an international journal published in association with BIBRA 24, 1053-1063 (2010).

Varghese K, et al. A new target for amyloid beta toxicity validated by standard and high-throughput electrophysiology. PLoS One 2010: 5(1): e8643.

Varghese K, et al. Regeneration and characterization of adult mouse hippocampal neurons in a defined in vitro system. J Neurosci Methods 2009; 177: 51-59.

Viravaidya K, et al. Incorporation of 33-11 cells to mimic bioaccumulation in a microscale cell culture analog device for toxicity studies. Biotechnol Prog 2004; 20: 590-597.

Wagner I, et al. A dynamic multi-organ-chip for long-term cultivation and substance testing proven by 3D human liver and skin tissue co-culture. Lab on a chip (2013).

Wilson K, et al. Direct patterning of coplanar polyethylene glycol alkylsilane monolayers by deep-ultraviolet photolithography as a general method for high fidelity, long-term cell patterning and culture. JVST B 2011; in press.

Wilson K. et al. Integration of functional myotubes with a bio-mems device for non-invasive interrogation. Lab Chip 2007; 7: 920-922.

Wilson K, et al. Measurement of contractile stress generated by cultured muscle on silicon cantilevers. PLoS One 2010; 5(6): e1 1042.

Xu H, et al. Development of a stable dual cell-line gfp expression system to study estrogenic endocrine disrupters. Biotechnol Bioeng 2008; 101(6): 1276-1287.

Zimmermann W H, et al. Tissue engineering of a differentiated cardiac muscle construct.

TABLE 1

Medium Composition 1

| No. | Component | Amount | | Catalogue# | Source |
|---|---|---|---|---|---|
| 1 | Neurobasal | 500 | mL | 10888 | Gibco/Invitrogen |
| 2 | Antibiotic-Antimycotic | 5 | mL | 15240-062 | Gibco/Invitrogen |
| 3 | G5 Supplement (100X) | 5 | mL | 17503-012 | Gibco/Invitrogen |
| 4 | VEGF 165 r Human | 10 | µg | P2654 | Gibco/Invitrogen |
| 5 | Acidic FGF | 12.5 | µg | 13241-013 | Gibco/Invitrogen |
| 6 | Heparin Sulfate | 50 | µg | 9809 | Sigma |
| 7 | LIF | 10 | µg | L5158 | Sigma |
| 8 | Vitronectin (Rat Plasma) | 50 | µg | V0132 | Sigma |
| 9 | CNTF | 20 | µg | CRC 401B | Cell Sciences |
| 10 | NT-3 | 10 | µg | CRN 500B | Cell Sciences |
| 11 | NT-4 | 10 | µg | CRN 501B | Cell Sciences |
| 12 | GDNF | 10 | µg | CRG 400B | Cell Sciences |
| 13 | BDNF | 10 | µg | CRB 600B | Cell Sciences |
| 14 | CT-1 | 10 | µg | CRC 700B | Cell Sciences |

TABLE 2

Medium Composition 2

| No | Component(s) | Amount | | Catalog | Source |
|---|---|---|---|---|---|
| 1 | Neurobasal | 500 | mL | 10888 | Invitrogen/Gibco |
| 2 | Antibiotic-antimycotic | 5 | mL | 15240-062 | Invitrogen/Gibco |
| 3 | Cholesterol (250X) | 5 | mL | 12531 | Invitrogen/Gibco |
| 4 | TNF-alpha, human | 10 | µg | T6674 | Sigma-Aldrich |
| 5 | PDGF BB | 50 | µg | P4056 | Sigma-Aldrich |
| 6 | Vasoactive intestinal peptide (VIP) | 250 | µg | V6130 | Sigma-Aldrich |
| 7 | Insulin-like growth factor 1 | 25 | µg | 12656 | Sigma-Aldrich |
| 8 | NAP | 1 | mg | 61170 | AnaSpec, Inc. |
| 9 | r-Apolipoprotein E2 | 50 | µg | P2002 | Panvera, Madison, WI |
| 10 | Laminin, mouse purified | 2 | mg | 08-125 | Millipore |
| 11 | Beta amyloid (1-40) | 1 | mg | AG966 | Millipore |
| 12 | Human Tenascin-C protein | 100 | µg | CC065 | Millipore |
| 13 | rr-Sonic hedgehog, Shh N-terminal | 50 | µg | 1314-SH | R&D Systems |
| 14 | rr-Agrin (C terminal) | 50 | µg | 550-AG-100 | R&D Systems |

TABLE 3

Serum-Free Culture Medium

| Component | Amount/Concentration | Company | Catalog Number |
|---|---|---|---|
| Neurobasal E | 500 mL | Gibco | 10888 |
| B27 | 10 mL | Gibco | 17504-044 |
| G5 (100x) | 1 mL | Invitrogen | 17503-012 |
| aFGF | 10 micro gm | Invitrogen | 13241-013 |
| VEGF 165 | 10 micro gm | Invitrogen | P2654 |
| Human BDNF | 10 micro gm | Cell Sciences | CRB 600B |
| Human GDNF | 10 micro gm | Cell Sciences | CRG4 00B |
| Rat CNTF | 25 micro gm | Cell Sciences | CRC 401B |
| Human CT-1 | 10 micro gm | Cell Sciences | CRC 700B |

TABLE 3-continued

Serum-Free Culture Medium

| Component | Amount/Concentration | Company | Catalog Number |
|---|---|---|---|
| NT-3 | 10 micro gm | Cell Sciences | CRN 500B |
| NT-4 | 10 micro gm | Cell Sciences | CRN 501B |
| De-N-sulphated N-acetylated heparin sulphate | 40 micro gm | Sigma | D9809 |
| Vitronectin | 50 micro gm | Sigma | V0132 |
| Glutamax (100x) | 5 mL | Invitrogen | 35050-061 |
| Antibiotic-Antimycotic 100x | 5 mL | Invitrogen | 15240-062 |

The invention claimed is:

1. A method of assessing one or more effects of varying an input variable or a cell culture characteristic on a microfluidic cell culture analog system, the method comprising:
   varying an input variable or a cell culture characteristic to which a microfluidic cell culture analog system is exposed, the microfluidic cell culture analog system comprising one or more organ components, each organ component configured to simulate an organ and comprising (i) one or more chambers, (ii) cell cultured on a surface, and (iii) if the microfluidic cell culture analog system comprises more than one organ component, microfluidic couplings between organ components;
   recording, over a duration of time, changes in measured electrophysiological properties, changes in measured contractile properties, or both in response to the varying input variable or cell culture characteristic;
   in which the electrophysiological properties, if recorded, are measured from a first population of cells cultured on a surface comprising a microelectrode array housed in a first chamber; and
   in which the contractile properties, if recorded, are measured from a second population of cells cultured on a surface comprising a cantilever array housed in a second chamber;
   the recorded changes providing an assessment of the one or more effects of varying an input variable or a cell culture characteristic; and
   mechanically actuating the second population of cells using the cantilever array.

2. The method of claim 1, wherein the duration of time is a time period of days.

3. The method of claim 1, further comprising multiple microfluidically coupled organ components, wherein the multiple microfluidically coupled organ components include a cardiac component, and the method further comprises measuring at least one electrophysiological property from cardiomyocyte cells cultured on a microelectrode array of the cardiac component and simultaneously measuring at least one contractile property from cardiomyocyte cells cultures on a cantilever array of the cardiac component.

4. The method of claim 3, wherein the multiple microfluidically coupled organ components further include a hepatic component.

5. The method of claim 1, further comprising multiple microfluidically coupled organ components, wherein the multiple microfluidically coupled organ components include a neural component and a skeletal muscle component, and the method further comprises measuring at least one electrophysiological property from neurons cultured on a microelectrode array of the neural component and simultaneously measuring at least one contractile property from skeletal muscles cultured on a cantilever array of the skeletal muscle component.

6. The method of claim 5, wherein the multiple microfluidically coupled organ components further include a hepatic component.

7. The method of claim 1, further comprising measuring changes in the input variable or the cell culture characteristic over the duration of time.

8. The method of claim 1, wherein changes in electrophysiological and contractile properties in response to the varying input variable or cell culture characteristic are measured simultaneously.

9. A method of assessing one or more effects of a metabolism of an input variable using a microfluidic cell culture analog system, the method comprising:
providing the microfluidic cell culture analog system, wherein the microfluidic cell culture analog system comprises a hepatic organ component and at least a first and second other organ component, each organ component configured to simulate an organ and comprising (i) one or more chambers, (ii) cell cultured on a surface, and (iii) microfluidic couplings between organ components;
contacting liver cells of the hepatic organ component with an input variable under conditions in which the liver cells at least partially metabolize the input variable into one or more hepatic metabolites;
allowing the input variable and the one or more hepatic metabolites to flow through the microfluidic cell culture analog system;
recording, over a duration of time, changes in simultaneously measured electrophysiological and contractile properties in response to the input variable and the one or more hepatic metabolites;
in which the electrophysiological properties are measured from a first population of cells cultured on a microelectrode array of the first organ component and the contractile properties are measured from a second population of cells cultured on a cantilever array of the second organ component;
the recorded changes providing an assessment of the one or more effects of the metabolism of the input variable.

10. The method of claim 9, further comprising comparing the changes in the simultaneously measured electrophysiological and contractile properties to information about the behavior of cells that have not been exposed to the one or more hepatic metabolites.

11. The method of claim 10, further comprising gathering information about behavior of cells that have not been exposed to the one or more hepatic metabolites using a microfluidic cell culture analog system without liver cells.

12. The method of claim 9, wherein the duration of time is a time period of days.

13. The method of claim 9, wherein the at least a first and second other organ components include a cardiac component, and the method further comprises measuring at least one electrophysiological property from cardiomyocyte cells cultured on a microelectrode array of the cardiac component and simultaneously measuring at least one contractile property from cardiomyocyte cells cultured on a cantilever array of the cardiac component.

14. The method of claim 9, wherein the at least a first and second other organ components include a neural component and a skeletal muscle component, and the method further comprises measuring at least one electrophysiological property from neurons cultured on a microelectrode array of the neural component and simultaneously measuring at least one contractile property from skeletal muscles cultured on a cantilever array of the skeletal muscle component.

15. The method of claim 9, further comprising mechanically stimulating the second population of cells using the cantilever array.

16. The method of claim 1, wherein the cantilever array comprises piezoresistive materials.

17. The method of claim 9, wherein the cantilever array comprises piezoresistive materials.

18. The method of claim 1, wherein the cantilever array is formed of silicon.

19. The method of claim 9, wherein the cantilever array is formed of silicon.

* * * * *